United States Patent
Montminy et al.

(10) Patent No.: US 10,258,639 B2
(45) Date of Patent: Apr. 16, 2019

(54) METHODS FOR TREATING INSULIN RESISTANCE AND FOR SENSITIZING PATIENTS TO GLP1 AGONIST THERAPY

(71) Applicant: Research Development Foundation, Carson City, NV (US)

(72) Inventors: Marc Montminy, La Jolla, CA (US); Sam Van De Velde, La Jolla, CA (US); Emilie Blanchet, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 15/308,652

(22) PCT Filed: May 6, 2015

(86) PCT No.: PCT/US2015/029411
§ 371 (c)(1),
(2) Date: Nov. 3, 2016

(87) PCT Pub. No.: WO2015/171723
PCT Pub. Date: Nov. 12, 2015

(65) Prior Publication Data
US 2017/0189440 A1    Jul. 6, 2017

Related U.S. Application Data

(60) Provisional application No. 61/989,108, filed on May 6, 2014, provisional application No. 62/113,670, filed on Feb. 9, 2015.

(51) Int. Cl.
| *A61K 31/70* | (2006.01) |
| *A61K 31/713* | (2006.01) |
| *A61K 38/26* | (2006.01) |
| *A61K 31/436* | (2006.01) |
| *A61K 31/565* | (2006.01) |
| *C12N 5/00* | (2006.01) |

(52) U.S. Cl.
CPC .......... *A61K 31/713* (2013.01); *A61K 31/436* (2013.01); *A61K 31/565* (2013.01); *A61K 38/26* (2013.01)

(58) Field of Classification Search
None
See application file for complete search history.

(56) References Cited

U.S. PATENT DOCUMENTS

| 2009/0029904 A1 | 1/2009 | Oldham |
| 2013/0143800 A1 | 6/2013 | Montminy et al. |
| 2015/0110862 A1* | 4/2015 | Liu .................. A61K 36/185 424/450 |
| 2015/0166477 A1* | 6/2015 | Pourgholami ........ C07C 317/44 514/522 |
| 2016/0303100 A1* | 10/2016 | Boss .................... C12N 5/0667 |
| 2016/0339019 A1* | 11/2016 | Laberge .............. A61K 31/428 |

FOREIGN PATENT DOCUMENTS

| WO | WO 2012/074676 | 6/2012 |
| WO | WO 2012/107476 | 8/2012 |

OTHER PUBLICATIONS

Blagosklonny, "TOR-centric view on insulin resistance and diabetic complications: perspective for endocrinologists and gerontologists," *Cell Death and Disease*, 4:e964, 2013.
Blanchet et al., "Feedback Inhibition of CREB Signaling Promotes Beta Cell Dysfunction in Insulin Resistance", *Cell Reports*, 10:7(1149-1157), 2015.
Buysschaert et al., "Glycemic control and weight changes in patients with type 2 diabetes intensified to three insulin regimens after therapeutic failure to exenatide.",*Acta Clinica Belgica*, 67:4(250-254), 2012.
Buysschaert et al., "One-year metabolic outcomes in patients with type 2 diabetes treated with exenatide in routine practice", *Diabetes & Metabolism*, 36:5(381-388), 2010.
Cho et al., "Deregulation of CREB signaling pathway induced by chronic hyperglycemia downregulates NeuroD transcription," *PLoS ONE*, 7(4):e34860, 2012.
Chung et al., "Overexpressing PKIB in prostate cancer promotes its aggressiveness by linking between PKA and AKT pathways", *Oncogene*, 28:32(2849-2859), 2009.
Kwon et al, "Signaling elements involved in the metabolic regulation of mTOR by nutrients, incretins, and growth factors in islets," *Diabetes*, 53:S225-S232, 2004.
PCT International Preliminary Report on Patentability issued in an International Application No. PCT/US2015/029411, dated Nov. 17, 2016.
PCT International Search Report and Written Opinion issued in an International Application No. PCT/US2015/029411, dated Jul. 22, 2015.
Van de Velde et al. "mTOR links incretin signaling to HIF induction in pancreatic beta cells," *PNAS*, 108(41):16876-16882, 2011.

* cited by examiner

*Primary Examiner* — Sean McGarry
(74) *Attorney, Agent, or Firm* — Parker Highlander PLLC

(57) ABSTRACT

Methods for treatment of insulin resistance and type II diabetes by administration of inhibitors of the PKI pathway are provided. In some aspects, inhibitors of the PKI pathway, such as inhibitors of PIKB, HIF1 and/or mTOR, can be used to treat subject having insulin resistance who are refractory to GLP1 agonist therapy.

15 Claims, 10 Drawing Sheets
Specification includes a Sequence Listing.

METHODS FOR TREATING INSULIN RESISTANCE AND FOR SENSITIZING PATIENTS TO GLP1 AGONIST THERAPY

This application is a national phase application under 35 U.S.C. § 371 of International Application No. PCT/US2015/029411, filed May 6, 2015, which claims the benefit of U.S. Provisional Patent Application Nos. 61/989,108, filed May 6, 2014, and 62/113,670, filed Feb. 9, 2015, each of which are incorporated herein by reference.

The invention was made with government support under Grant Nos. R01-DK049777, R01-DK083834, and R01-DK091618 awarded by the National Institutes of Health. The government has certain rights in the invention.

INCORPORATION OF SEQUENCE LISTING

The sequence listing that is contained in the file named "CLFR_P0422WO_ST25.txt", which is 49 KB (as measured in Microsoft Windows®) and was created on May 5, 2015, is filed herewith by electronic submission and is incorporated by reference herein.

BACKGROUND OF THE INVENTION

1. Field of the Invention

The present invention relates generally to the field of molecular biology and endocrinology. More particularly, it concerns methods for the treatment of elevated serum glucose, insulin resistance and diabetes mellitus.

2. Description of Related Art

Regulation of glucose homoeostasis in the bloodstream must be tightly controlled to maintain healthy metabolic function. Low serum glucose levels (hypoglycemia) can lead to weakness, headaches, confusion, and if unchecked, ultimately convulsions, coma, and death. On the other hand, hyperglycemia causes excess urine production, thirst, weight loss, fatigue, and in severe cases can also result in coma and death. Chronically high blood sugar also causes long term tissue damage that may contribute to diabetic complications, such as blindness, kidney failure, impotence, atherosclerosis, and increased vulnerability to infection.

In a healthy subject, pancreatic tissue is responsible for secretion of hormones that regulate serum glucose homeostasis. After a meal, when blood glucose levels rise, secretion of insulin lowers blood sugar by stimulating tissue glucose uptake (the primary tissue responsible being skeletal muscle). Conversely, when serum glucose levels fall, secretion of glucagon stimulates the liver to release stored glucose into the blood stream.

Diabetes mellitus is an increasingly common disorder around the world, characterized by chronically elevated serum glucose levels. Classically, diabetes segregates into two distinct groups that require alternative therapeutic approaches. Type 1 diabetes, is primarily caused by an inability of the subject to produce sufficient insulin to regulate blood sugar. On the other hand, type 2 diabetes is characterized by a reduced ability to respond to serum insulin, a state know as insulin resistance. Treatment of both types of diabetes can involve the administration of insulin, however, frequent insulin injections are both expensive and burdensome, involving the need for constant blood sugar assessment to regulate and time insulin dosing.

SUMMARY OF THE INVENTION

Embodiments of the instant invention as based on the finding that log-term activation of beta cells results in a feedback response mediated by the Protein Kinase Inhibitor (PKI) pathway, which prevents further activation of the beta cells. Without being bound by any particular mechanism, it is proposed that the prolonged activation of beta cells results in an effective de-differentiation of the cells thereby rendering them significantly less effective regulating glucose homeostasis. Methods provided herein may allow for "reactivation" (or prevention of deactivation) of beta cells by the use to inhibitors of the PKI pathway. Thus, in some aspects, inhibitors of the PKI pathway may be used to sensitize a subject to treatment with a conventional therapeutic for insulin resistance such as GLP1 agonists.

In a first embodiment there is provided a method of treating a subject having insulin resistance comprising administering an effective amount of an inhibitor of the PKI pathway to the subject having insulin resistance. For instance, in some aspects, the inhibitor of the PKI pathway is an inhibitor of the PKIA, PKIB or PKIG pathway. In certain aspects the inhibitor of the PKIB pathway is an inhibitor of PIKB (e.g., an inhibitor nucleic acid, which reduced expression of PKIB), a HIF1 inhibitor or a mTOR inhibitor. In still further aspects, a subject for treatment according the embodiments is a subject who has been diagnosed with type 2 diabetes, such as a subject with type 2 diabetes who is resistant to the a Glucagon-like peptide-1 (GLP1) agonist therapy.

Thus, in a further embodiment, there is provided method for treating a subject having insulin resistance comprising administering an effective amount of a PKI pathway inhibitor to a subject who has been determined to be resistant to a GLP1 agonist therapy. For instance, in some aspects, the inhibitor of the PKI pathway is an inhibitor of the PKIA, PKIB, or PKIG pathway. In further aspects, the PKI pathway inhibitor is a PKIB pathway inhibitor selected from the group consisting of an inhibitor of PKIB, a mTOR inhibitor and a HIF1 inhibitor.

In still further aspects, a method of the embodiments comprises administering a GLP1 agonist to the patient in conjunction with the PKI pathway inhibitor (e.g., a PKIA, PKIB or PKIG pathway inhibitor). For example, a PKI pathway inhibitor may be administered before, after or essentially simultaneously with the GLP1 agonist. A skilled artisan will recognize that, in some aspects, certain PKI pathways inhibitors (e.g., HIF1 inhibitors and mTOR inhibitors) operate in opposition to the acute effects of GLP1 agonists. Accordingly, in preferred aspects, PKI pathway inhibitors are administered prior to treatment with a GLP1 agonist. For example, in a subject identified as resistant to GLP1 agonist therapy, the subject may be administered one, two, three or more doses of a PKI pathways inhibitor (e.g., over a period of 1, 2, 3, 4, 5, or more days) prior administering (or resuming administration) of a GLP1 agonist therapy. Thus, in some aspects, a subject resistant to GLP1 agonist therapy is alternatively administered a PKI pathway inhibitor of the embodiments and a GLP1 agonist. For example, a subject may be administered a GLP1 agonist over a period of 1, 2, 3, 4, weeks or more and then the therapy replaced with a period of treatment with a PKI pathway inhibitor for a period of 1, 2, 3, 4, 5 days or more before resuming GLP1 agonist therapy. For course, in some aspects, a subject undergoing treatment according to the embodiments may be administered one or more secondary treatment along with a GLP1 agonist and/or PKI pathways inhibitor therapy (e.g., the subject may be treated with a insulin, such as along-acting insulin (insulin glargine; Lantus®).

Certain aspects of the embodiments concern treatment of subject who are resistant to a GLP1 agonist therapy. As used herein a "GLP1 agonist therapy" refers both treatment with a GLP1 agonist per se (e.g., Exenatide (Byetta®), Liraglutide, Taspoglutide, Albiglutide or Lixisenatide) and to treatments that induce production of endogenous GLP1 agonists such as dipeptidyl peptidase 4 (DPP-4) inhibitors (e.g., Sitagliptin (Januvia), Vildagliptin (Galvus), Saxagliptin (Onglyza), Linagliptin, Anagliptin, Teneligliptin, Alogliptin, Gemigliptin or Dutogliptin). Thus, as used herein, a subject who is "resistant to a GLP1 agonist therapy" refers to a subject who exhibits insignificant reductions in blood glucose (or reductions in blood glucose that not sufficient to control disease) in response to a GLP1 agonist therapy. In some aspects, a subject who is resistant to GLP1 agonist therapy is a subject who has developed GLP1 agonist resistance, such as a subject who is being treated with a GLP1 agonist therapy, but who exhibits decreasing response to the therapy over time.

As further detailed herein, some aspects of the embodiments concern administering a PKI pathway inhibitor to a subject in conjunction with a GLP1 agonist (or a DPP-4 inhibitor). Again as used here a "GLP1 agonist" refers both to agonist molecules per se (including molecules having combined GLP1 and GIP agonist activity) as well as molecules that increase endogenous incretin, such as DPP-4 inhibitors. Thus, in some aspects, a GLP1 agonist for use according to the embodiments can comprise exenatide, bydureon, liraglutide, albiglutide, taspoglutide or lixisenatide. In some aspects, the GLP1 agonist is exenatide. In further aspects, a PKI pathway inhibitor is administered in conjunction with a DPP-4 inhibitor such as sitagliptin (MK-0431), vildagliptin (LAF237), saxagliptin, linagliptin, dutogliptin, gemigliptin, berberine, and alogliptin. Further GLP1 agonists and DPP-4 inhibitors for use according to the embodiments are detailed herein below.

Further aspects of the embodiments concern administration of PKI inhibitors to a subject. For example, in some aspects, the PKI inhibitor is an inhibitor of PKIB. In some aspects, an inhibitor of PKIB can be an inhibitory nucleic acid, such as a nucleic acid that is complimentary to all of part of a PKIB mRNA (e.g., as provided in SEQ ID NO: 2, SEQ ID NO: 4, SEQ ID NO: 5, SEQ ID NO: 6, SEQ ID NO: 7 or SEQ ID NO: 8). In certain preferred aspects the inhibitory nucleic acid is an RNA such as a dsRNA, siRNA, miRNA or shRNA. In still further aspects, a PKI inhibitor for use according to the embodiments is an inhibitor of PKIA. For example, an inhibitor of PKIA can be an inhibitory nucleic acid, such as a nucleic acid that is complimentary to all of part of a PKIA mRNA (e.g., as provided in SEQ ID NO: 10 and SEQ ID NO: 11). In certain preferred aspects the inhibitory nucleic acid is an RNA such as a dsRNA, siRNA, miRNA or shRNA. In yet further aspects, a PKI inhibitor for use according to the embodiments is an inhibitor of PKIG. For example, an inhibitor of PKIG can be an inhibitory nucleic acid, such as a nucleic acid that is complimentary to all of part of a PKIG mRNA (e.g., as provided in SEQ ID NO: 12, SEQ ID NO: 13, SEQ ID NO: 14, SEQ ID NO: 15 and SEQ ID NO: 16). In certain preferred aspects the inhibitory nucleic acid is an RNA such as a dsRNA, siRNA, miRNA or shRNA.

Yet further aspects of the embodiments concern PKI pathway inhibitors such as mTOR inhibitors. For example, in preferended aspects, the mTOR inhibitor is a small molecule mTOR inhibitor such as sirolimus, everolimus, temsirolimus, zotarolimus, tacrolimus, SAR543, ascomycin, deferolimus, AP23841, KU-0063794, INK-128, EX2044, EX3855, EX7518, AZD08055, OSI-027, WYE-125132, XL765, NV-128, WYE-125132 or EM101/LY303511. In further preferred aspects the mTOR inhibitor is a rapamycin or rapamycin derivative, in particular sirolimus or everolimus rapamycin. Further mTOR inhibitors for use according to the embodiments are detailed herein below.

Still further aspects of the embodiments concern PKI pathway inhibitors, which are HIF1 inhibitors. For example, in some aspects the HIF1 inhibitor comprises FG-4592, IOX2, 2-Methoxyestradiol (2-MeOE2), CL67, CAY10585 (CAS 934593-90-5), sc-205346 (CAS 934593-90-5), Chetomin (CAS 1403-36-7) or Chrysin (CAS 480-40-0). Further HIF1 inhibitors for use according to the embodiments are detailed herein below.

In preferred aspects, a subject of the embodiments is a human subject. In some aspects, a subject having insulin resistance according to the embodiments is subject diagnosed with a metabolic disease selected from the group consisting of type 2 diabetes; metabolic syndrome; nonalcoholic fatty liver disease; and/or polycystic ovarian syndrome.

In a further embodiment there is provided a method for treating a cancer, such as a cancer associated with diabetes, comprising administering an effective amount of an inhibitor of PKIB. For example, in some aspects the diabetes associated cancer is liver cancer, pancreatic cancer, colorectal cancer, kidney cancer, breast cancer, bladder cancer, endometrial cancer or non-Hodgkin's lymphoma. In some aspects, an inhibitor of PKIB can be an inhibitory nucleic acid, such as a nucleic acid that is complimentary to all of part of a PKIB mRNA (e.g., as provided in SEQ ID NO: 2, SEQ ID NO: 4, SEQ ID NO: 5, SEQ ID NO: 6, SEQ ID NO: 7 or SEQ ID NO: 8). In certain preferred aspects, the inhibitory nucleic acid is an RNA such as a dsRNA, siRNA, miRNA or shRNA.

It will also be understood that, in some embodiments, methods are provided for treating mammalian diseases that that involve insulin resistance and/or chronic elevation of serum insulin levels. Thus, in some aspects methods are provided to treat and/or prevent the pathologic onset of type 2 diabetes, metabolic syndrome, nonalcoholic fatty liver disease and/or polycystic ovarian syndrome in a subject. These methods may involve increasing insulin-sensitivity in the subject. As described above methods of the embodiments involve administering a PKIB pathway inhibitor to a subject, such as a subject that is resistant to a GLP1 agonist therapy. In certain embodiments, methods according the embodiments can be used to delaying the onset of a disease, such as type 2 diabetes, in a subject at risk for developing the disease or with a genetic predisposition for such a disease. As used here "at risk" subjects can include but is not limited to obese subjects or aged individuals. Furthermore, at risk subjects may have chronic elevated blood insulin, triglycerides or glucose levels and/or have high blood pressure.

Methods according to the embodiments may also be used in combination with other therapeutic strategies that are known to those of skill in the art. For example, in certain aspects, methods may be used in combination with insulin administration. In this case, such methods may reduce the amount of insulin that must administered and/or the frequency at which the insulin is administered. Other compounds that are known in the art to be effective for regulating glucose homeostasis include sulfonylureas, alpha-glucosidase inhibitors, thiazolidinediones, motformin and repaglinide. Thus, methods of the embodiments may additionally comprise, administering a sulfonylurea, an alpha-glucosidase inhibitor, a thiazolidinedione, motformin, or repaglinide to a subject. Combination treatment may be particularly preferred as they can reduce the effective concentrations of each therapeutic compound used and thus limit undesirable side effects of the compounds.

In still further embodiments of the present invention relate to a pharmaceutical preparation comprising a GLP1 agonist (DPP-4 inhibitor) and PKI pathway inhibitor. For example, such a pharmaceutical preparation may be formulated for oral, intravenous or subcutaneous administration, depending on the particular molecules comprised in the formulation.

In yet a further embodiment there is provided a composition comprising PKI pathway inhibitor (e.g., a PKIB pathway inhibitor) for use in treating a subject having insulin resistance and who has been determined to be resistant to GLP1 agonist therapy. In some specific aspects such a composition comprises an inhibitor of PKIB, a mTOR inhibitor and/or HIF1 inhibitor.

In still yet a further embodiment a composition is provided comprising an inhibitor of the PKIB for use in treating a subject having insulin resistance. For example, in some aspects the inhibitor of the PKIB is an inhibitory nucleic acid that is complimentary to all or part of the PKIB mRNA.

In still a further embodiment there is provided an assay method comprising (a) obtaining a sample from the subject suspected of having impaired islet function; and (b) measuring the level of PKIB mRNA or protein in the sample. In a further embodiment a method is provided for determining whether a subject has impaired islet function comprising (a) obtaining a sample from the subject; and (b) measuring the level of PKIB mRNA or protein in the sample, wherein an elevated level of PKIB indicates impaired islet function. In some aspects, a sample for use according to the embodiments may be a solid tissue sample or a biological fluid (e.g., a blood urine or saliva sample). In certain aspects, measuring a level of PKIB in the sample comprises measuring the level of mRNA (e.g., by RT-PCR). In still further aspects, measuring the level of PKIB can comprise measuring a level of PKIB protein in the sample (e.g., such as by use of a PKIB-binding antibody). Specific assay methods that may be used include, without limitation, an ELISA, an immunoassay, a radioimmunoassay (RIA), Immunohistochemistry, an immunoradiometric assay, a fluoroimmunoassay, a chemiluminescent assay, a bioluminescent assay, a gel electrophoresis or a Western blot analysis.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

Figure 1:
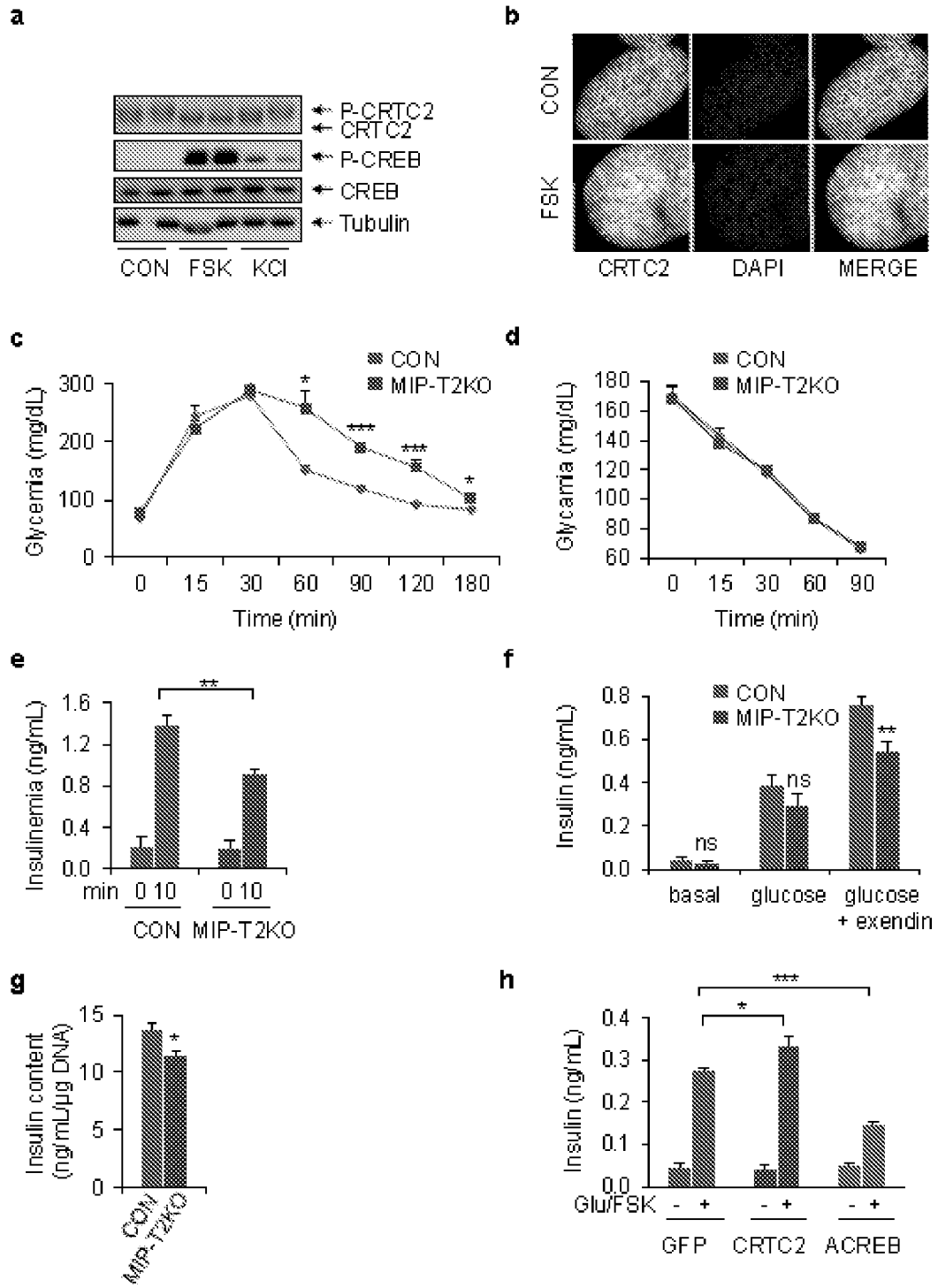
FIG. 1: Impaired glucose tolerance in mice with a beta cell specific knockout of CRTC2. a. and b. Dephosphorylation and nuclear translocation of CRTC2 in INS1 (a) and mouse pancreaitc islets (b) following exposure to cAMP agonist forskolin (FSK) or KCl. c. Oral glucose tolerance testing (OGTT) of mice with a knockout of CRTC2 in beta cells (MIP-T2KO; indicated by filled black squares) relative to control littermates (*$p<0.05$; $p<0.01$; *$p<0.001$; n=10). d. Insulin tolerance testing of control and MIP-T2KO mice. e. Circulating insulin concentrations in MIP-T2KO (indicated by filled black squares) and control littermates 10 minutes following administration of glucose ($p<0.01$: n=10). f. Effect of glucose alone (20 mM) or plus exendin (10 nM) on insulin secretion from primary cultured islets of MIP-T2KO and control littermates ($p<0.01$; n=6). g. Insulin content in pancreatic islets from CRTC2 mutant or control littermates (*$p<0.05$; n=6). h. Effect of CRTC2 or dominant negative A-CREB over-expression on insulin secretion from INS1 cells (*$p<0.05$, ***$p<0.001$; n=5). Data are shown as mean±s.e.m.

Relative body weight (b), fasting glucose concentrations (c) and insulin secretion from cultured pancreatic islets (d) of PKIB knockout and control littermates following 20 weeks of high fat diet (*p<0.05, *p<0.001. n=5). e. and f. Effect of HIF1 knockdown or over-expression on mRNA amounts for PKIB in INS1 cells exposed to FSK as indicated (p<0.01, *p<0.001. n=3). g. and h. PKIB mRNA (g) and protein (h) amounts in cells exposed to prolyl hydroxylase inhibitor DMOG, which upregulates HIF1 protein levels in INS1 cells. Treatment with FSK indicated (p<0.01. n=6).

DESCRIPTION OF ILLUSTRATIVE EMBODIMENTS

I. The Present Invention

Insulin resistance such as in type II diabetes mellitus is an increasingly common disorder around the world. However, despite extensive study the development of a wide range of therapeutics adequate control of the disease has proved to be challenging. GLP1 agonist based therapies such as Byetta® (exenatide), for example, while promising have provided to be ineffective in certain type II diabetes patients. Thus, there remains a significant need for new therapeutic approaches to treat insulin resistance.

Studies presented herein address an important and unrecognized underlying mechanism of beta cell dysfunction and insulin resistance. It was demonstrated that the induction of a compensatory growth pathway in response to nutrient stress impairs cell function by blocking the expression of a genetic program required for cellular maturation. In the short term, GLP1 and glucose promote the adaptive expansion of pancreatic islet mass through CREB mediated increases in mTORC1 activity that culminate in the induction of the HIF pathway (see, e.g., U.S. Pat. Publn. 20130143800, incorporated herein by reference). Importantly, however, when stimulation is prolonged HIF1 feeds back to inhibit CREB activity by stimulating the expression of PKIB and thereby blocking the activation of PKA in response to GLP1. Thus, while initially HIF1 and mTOR are involved in GLP1-mediated beta cell activation, after prolonged activation HIF1 and mTOR activity limit GLP1-mediated activation (i.e., via PKIB). Accordingly, by inhibiting the PKI pathway (e.g., with an inhibitor of HIF1, mTOR or PKIB) the activity of the GLP1 activation pathway can be restored.

The studies presented are of particular interest given that a sizable percentage of type II diabetic patients appear to be unresponsive to GLP1 agonist therapy (Hall et al., 2013; Preumont et al., 2012; Buysschaert et al., 2012). Such GLP1 agonist resistance is likely mediated, at least in part, by up-regulation of PKIs (e.g., PKIA and PKIB). Accordingly, inhibitors of PKI or PKI pathway components (such as inhibitors of HIF1 or mTOR) could be used to restore sensitivity to GLP1 agonist therapy or treat subject that have a resistance to GLP1 agonist therapies. Thus, the methodologies provided herein can provide avenues for treatment of insulin resistance also was significantly increasing the effectiveness of currently available therapies.

II. PKI Pathway Inhibitors mTOR Inhibitors

In some aspects, PKI inhibitors for use according to present embodiments comprise mTOR inhibitors. Such mTOR inhibitors include rapamycin which is an immunosuppressive lactam macrolide that is produced by *Streptomyces hygroscopicus*. For example, sirolimus or derivatives/analogs thereof such as everolimus (RAD001), temsirolimus (CCI-779), zotarolimus (ABT578), tacrolimus (FK-506), SAR543, ascomycin (an ethyl analog of FK506), deferolimus (AP23573/MK-8669), AP23841, KU-0063794, INK-128, EX2044, EX3855, EX7518, AZD08055, OSI-027, WYE-125132, XL765, NV-128, WYE-125132, and EM101/LY303511 may be used according to the embodiments.

Additional rapamycin derivative for use according to the embodiments include, without limitation a substituted rapamycin e.g., a 40-O-substituted rapamycin see e.g. those detailed in U.S. Pat. No. 5,258,389, WO 94/09010, WO 92/05179, U.S. Pat. Nos. 5,118,677, 5,118,678, 5,100,883, 5,151,413, 5,120,842, WO 93/11130, WO 94/02136, WO 94/02485 and WO 95/14023 (each of which is incorporated herein by reference); a 16-O-substituted rapamycin such as those disclosed in WO 94/02136, WO 95/16691 and WO 96/41807 (each incorporated herein by reference); a 32-hydrogenated rapamycin (e.g. as described in WO 96/41807 and U.S. Pat. No. 5,256,790, incorporated herein by reference). In certain aspects, a rapamycin derivative for use according to the embodiments has a formula such as (I):

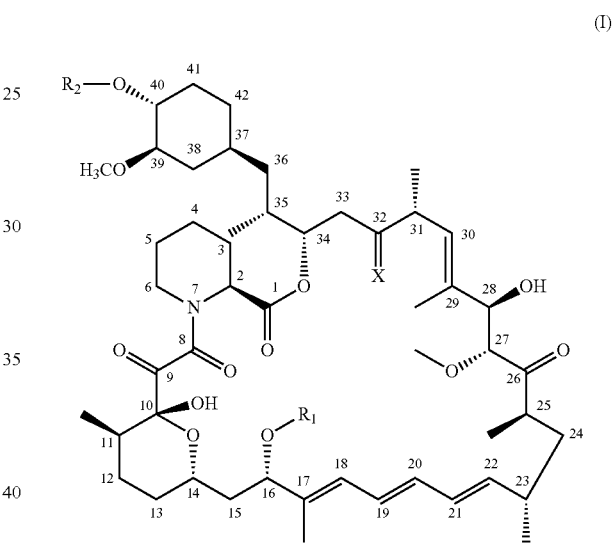

(I)

wherein $R_1$ is $CH_3$ or $C_{3-6}$alkynyl; $R_2$ is H or —$CH_2$—$CH_2$—OH, 3-hydroxy-2-(hydroxymethyl)-2-methyl-propanoyl or tetrazolyl, and X is =O, (H,H) or (H,OH), provided that $R_2$ is other than H when X is =O and $R_1$ is $CH_3$, or a prodrug thereof when $R_2$ is —$CH_2$—$CH_2$—OH, e.g. a physiologically hydrolysable ether thereof. Compounds such as those of (I) are disclosed e.g., in International PCT Applications WO94/09010, WO95/16691 or WO 96/41807, which are incorporated herein by reference.

Still further compounds for use according to the embodiments include, without limitation, are 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-O-(2-hydroxyethyl)-rapamycin and, more preferably, 40-O-(2-hydroxyethyl)-rapamycin (see, e.g., WO94/09010, incorporated herein by reference).

In some aspects, rapamycin derivatives of formula (I) are 40-O-(2-hydroxyethyl)-rapamycin, 40-[3-hydroxy-2-(hydroxymethyl)-2-methylpropanoate]-rapamycin (also called CCI779), 40-epi-(tetrazolyl)-rapamycin (also called ABT578), 32-deoxorapamycin, 16-pent-2-ynyloxy-32(S)-dihydro rapamycin, or TAFA-93.

Rapamycin derivatives may also include so-called rapalogs, e.g. as disclosed in International PCT Applications WO98/02441 and WO01/14387, e.g. AP23573, AP23464, or AP23841. Further derivatives for use according to the embodiments include FK-506 binding protein or FKBP-12), e.g. as described in International PCT Applications WO94/09010, WO95/16691 or WO96/41807, been found to be useful e.g. as immunosuppressant, e.g. in the treatment of acute allograft rejection.

In further aspects, the mTOR inhibitor can be a compound such as AZD08055 (AstraZeneca) or OSI-027 (OSI Pharmaceuticals), which inhibit the kinase activity of mTOR by directly binding to the ATP-binding cleft of the enzyme.

PKI Inhibitors

In certain aspects methods involve the use of an inhibitor of PKI such as and inhibitor of PKIA or PKIB. In certain aspects this can be accomplished by administration of an inhibitory nucleic acid that reduced expression of PKIA and/or PKIB. Examples of inhibitory nucleic acids include, without limitation, antisense nucleic acids, small interfering RNAs (siRNAs), double-stranded RNAs (dsRNAs), micro-RNAs (miRNA) and short hairpin RNAs (shRNA) that are complimentary to all or part of PKI mRNA. An inhibitory nucleic acid can, for example, inhibit the transcription of a gene in a cell, mediate degradation of an mRNA in a cell and/or inhibit the translation of a polypeptide from a mRNA. Typically an inhibitory nucleic acid may be from 16 to 1000 or more nucleotides long, and in certain embodiments from 18 to 100 nucleotides long. In certain embodiments, the inhibitory nucleic acid may be 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some aspects an inhibitory nucleic acid may comprise one or more modified nucleotide or nucleic acid analog. Typically, an inhibitory nucleic acid will inhibit the expression of a single gene within a cell; however, in certain embodiments, the inhibitory nucleic acid will inhibit the expression of more than one gene within a cell.

In some aspects an inhibitory nucleic acid can form a double-stranded structure. For example, the double-stranded structure may result from two separate nucleic acid molecules that are partially or completely complementary. In certain embodiments, the inhibitory nucleic acid may comprise only a single nucleic acid or nucleic acid analog and form a double-stranded structure by complementing with itself (e.g., forming a hairpin loop). The double-stranded structure of the inhibitory nucleic acid may comprise 16 to 500 or more contiguous nucleobases. For example, the inhibitory nucleic acid may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that are complementary to a PKIA or PKIB mRNA. Methods for using such siRNA or double-stranded RNA molecules have been described in U.S. Pat. Nos. 6,506,559 and 6,573,099, as well as in U.S. Applications 2003/0051263, 2003/0055020, 2004/0265839, 2002/0168707, 2003/0159161, 2004/0064842, each of which are herein incorporated by reference in their entirety.

Some specific aspects, inhibitory nucleic acid molecules contemplated for use according to the embodiments include but are not limited to molecules that comprise 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides that are complementary to the nucleotide sequence encoding a human PKIB isoform 1 mRNA (e.g., PKIB isoform 1, variant 1, 2, 3 or 4 provided as SEQ ID NO: 6, "variant 1"; SEQ ID NO: 7, "variant 2"; SEQ ID NO: 8, "variant 3"; and SEQ ID NO: 2 "variant 4", NCBI Accession Nos. NM_181795, NM_181794, NM_032471, and NM_001270393, respectively) or human PKIB isoform 2 mRNA (e.g., PKIB isoform 2, variant 5 or 6 provided as SEQ ID NO: 4 "variant 5"; and SEQ ID NO: 5, "variant 6", NCBI Accession No. NM_001270394, and NM_001270395, respectively). In still a further aspect a inhibitory nucleic acid molecule is complementary to all or part of a human PKIA mRNA (e.g., provided as SEQ ID NO: 10, "variant 1"; and SEQ ID NO: 11, "variant 2", NCBI Accession Nos. NM_006823 and NM_181839, respectively). In yet a further aspect a inhibitory nucleic acid molecule is complementary to all or part of a human PKIG mRNA (e.g., provided as SEQ ID NO: 12, "variant 1"; SEQ ID NO: 13, "variant 2", SEQ ID NO: 14, "variant 3"; SEQ ID NO: 15, "variant 4"; or SEQ ID NO: 16, "variant 5", NCBI Accession Nos. NM_181805.2, NM_007066.4, NM_181804.2, NM_001281444.1 and NM_001281445.1, respectively).

Methods for preparing and using inhibitory nucleic acid molecules in accordance with the embodiments are well known in the art. Likewise methods for delivering inhibitory nucleic acid molecule molecules into cells are also well known in the art. For example inhibitory nucleic acid (or inhibitory nucleic acid expression vectors) may be delivered in nanoparticles or liposomes such as 1,2-bis(oleoyloxy)-3-(trimethyl ammonio)propane (DOTAP) and cholesterol liposomes or cationic liposomes, see U.S. Pat. No. 6,806,084. Additionally, in the case of expression vector systems delivery may be accomplished in viral vectors. Some non-limiting examples of viruses contemplated herein for nucleic acid delivery include herpesviaral vectors; adenoviral vectors, retroviral and lentiviral vectors, such as those described in U.S. Patent App. 20050014166; and adeno-associated viral vectors, for example as described in U.S. Pat. Nos. 5,139,941 and 4,797,368.

In certain aspects of the embodiments inhibitory nucleic acid molecules may also be expressed in cells from an expression vector. For example expression can be under the transcriptional control of a RNA Polymerase III promoter, such as the U6 promoter. Such promoters are preferred for the expression of short RNA sequences, such as siRNA molecules. In certain aspects tissue specific promoters may also be employed, for example promoter that express nucleic acids in pancreatic islet cells. Specific vectors to express inhibitory nucleic acids are well known in the art. For example the commercially available pSUPER RNAi System™ available from OilgoEngine® and the pSilencer™ siRNA expression vectors available from Life Technologies™.

In still a further embodiment an inhibitor of PKI (e.g., an inhibitor of PKIA or PKIB) is molecule that binds to and inhibits PKI. For example, the inhibitor of PKI may be a small molecule, an aptamer or antibody (or fragment thereof) that binds to PKIA and/or PKIB. In some aspects, an aptamer or antibody of the embodiments specifically binds to a human PKIB isoform 1 (SEQ ID NO: 1), PKIB isoform 2 (SEQ ID NO: 3) and/or human (SEQ ID NO: 9). Methods for making and using antibodies are well known in the art and are detailed for example in U.S. Pat. No. 4,816,567, incorporated herein by reference. Likewise, methods for making aptamers, such as by SELEX, are well know and detailed in U.S. Pat. Nos. 6,569,620 and 6,716,580, incorporated herein by reference.

HIF1 Inhibitors

In some aspects, a PKI pathway inhibitor for use according to the embodiments is a HI1 inhibitor. For instance a HIF1 inhibitor can be a an inhibitor of HIF1 mRNA expression, an inhibitor of HIF1 protein translation, an inhibitor of HIF1 DNA binding and inhibitor of HIF 1 DNA binding or a molecule that increased HIF1 protein degradation (see, e.g., Onnis et al., 2009, incorporated herein by reference). In certain specific aspects a HIF 1 inhibitor for use according to the embodiments comprises YC-1 (3-(5'-hydroxymethyl-2'-furyl)-1-benzyl indazole), FG-4592, IOX2, 2-Methoxyestradiol (2-MeOE2), CL67, CAY10585 (CAS 934593-90-5), sc-205346 (CAS 934593-90-5), Chetomin (CAS 1403-36-7) or Chrysin (CAS 480-40-0) or PX-478.

Thus, in a some aspects, a HIF1 inhibitor that HIF1 mRNA expression is a inhibitor nucleic acid that binds to all or part of the human HIF1 mRNA. For example, inhibitory nucleic acid molecules contemplated for use according to the embodiments include but are not limited to molecules that comprise 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more nucleotides that are complementary to the nucleotide sequence encoding a human HIF1 mRNA. In some aspects the inhibitory nucleic acid is a RNA, such as a siRNA, shRNA, dsRNA or miRNA. As specific example of such an inhibitory nucleic acid is ENZ-2968. In still further embodiments an inhibitor that reduces HIF1 mRNA expression is aminoflavone. Additional HIF1 inhibitors, which inhibit HIF1 protein translation include, without limitation, ENZ-2208 and PX-478.

III. GLP1 Agonists and Incretin-Inducing Agents

GLP1 is itself derived from the transcription product of the proglucagon gene. GLP1 is primarily produced by the intestinal L cells that secrete GLP1 as a gut hormone. The biologically active forms of GLP1 are: GLP1-(7-37) and GLP1-(7-36)NH$_2$, which result from selective cleavage of the proglucagon molecule. The incretin hormone GLP1 enhances islet cell survival through induction of the cAMP pathway in beta cells as further detailed herein (see, also Drucker, 2006; Drucker and Nauck, 2006).

Certain aspects of the embodiments concern administration of GLP1 agonists to a subject in conjunction with a PKI pathway inhibitor. Likewise, some aspects of the embodiments concern treatment of subjects who are resistant to a GLP1 agonist therapy (with a PKI pathway inhibitor). In various embodiments, the GLP1 agonist may be selected from the group consisting of exenatide, bydureon, liraglutide, albiglutide, taspoglutide, and lixisenatide.

Exenatide

Exenatide is a GLP1 agonist that may be used to maintain blood glucose levels and treat aspects of diabetes. Exenatide is marketed as Byetta® and manufactured by Amylin Pharmaceuticals and Eli Lilly and Company. Exenatide typically administered to a patient as a subcutaneous injection, e.g., of the abdomen, thigh, or arm. Exenatide is typically administered within about 1 hour before the first and last meal of the day.

Exenatide is typically supplied for subcutaneous injection as a sterile, preserved isotonic solution in a glass cartridge that has been assembled in a pen-injector (pen). Each milliliter (mL) may contain about 250 micrograms (mcg) of synthetic exenatide, about 2.2 mg metacresol as an antimicrobial preservative, mannitol as a tonicity-adjusting agent, and glacial acetic acid and sodium acetate trihydrate in water for injection as a buffering solution at pH 4.5. Prefilled pens may be used to deliver unit doses of 5 mcg or 10 mcg. Commercially available prefilled pens can typically deliver 60 doses to provide for 30 days of twice daily administration (BID). Although, in certain preferred embodiments, exenatide may be administered subcutaneously, it is nonetheless anticipated that exenatide may in certain embodiments be administered via another route, e.g., intravenous, intramuscular, etc. In some aspects, exenatide is administered in conjunction with a long-acting insulin.

Bydureon™ is an extended release version of exenatide that may be used in various embodiments of the present invention. Bydureon™ may be administered to a subject less frequently than Byetta™. For example, bydureon may be administered subcutaneously to a subject about once per week. Bydureon™ is commercially available from Amylin Pharmaceuticals, Inc. (San Diego, Calif.).

Liraglutide

Liraglutide (NN2211) is a long-acting GLP1 analog that may be administered to a subject for the treatment of type 2 diabetes. Liraglutide is a DPP-IV-resistant GLP1 analog that has been modified by 2 amino acid changes, i.e., one addition and one substitution, and by the addition of a fatty acid group that enables it to form a noncovalent bond with serum albumin following SC administration, thus reducing its renal clearance and increasing its PK profile. The half-life of liraglutide in humans is approximately 12 hours and may require only 1 injection per day. Liraglutide marketed under the brand name Victoza™ and is manufactured by Novo Nordisk. Liraglutide currently in use has the chemical formula: L-histidyl-L-alanyl-L-α-glutamylglycyl-L-threonyl-L-phenylalanyl-L-threonyl-L-seryl-L-α-aspartyl-L-valyl-L-seryl-L-seryl-L-tyrosyl-L-leucyl-L-α-glutamylglycyl-L-glutaminyl-L-alanyl-L-alanyl-N6-[N-(1-oxohexadecyl)-L-γ-glutamyl]-L-lysyl-L-α-glutamyl-L-phenylalanyl-L-isoleucyl-L-alanyl-L-tryptophyl-L-leucyl-L-valyl-L-arginylglycyl-L-arginyl-glycine.

Liraglutide typically has a half-life after subcutaneous injection of about 11-15 hours after subcutaneous injection, making it suitable for once-daily dosing (less frequent than the currently approved Byetta™ form of exenatide, which is twice daily, but considerably more frequent than the once weekly Bydureon™ form of exenatide). Although, in certain embodiments, liraglutide is administered subcutaneously, it is nonetheless anticipated that exenatide may in certain embodiments be administered via another route, e.g., intravenous, intramuscular, etc.

Ablugtide

In some embodiments, the GLP1 agonist may be albiglutide. The long-acting GLP1 receptor agonist albiglutide is a recombinant human serum albumin (HSA)-GLP1 hybrid protein, i.e., a dipeptidyl peptidase-4-resistant glucagon-like peptide-1 dimer fused to human albumin. As the GLP1 epitopes are fused to the larger HSA molecule, albiglutide exhibits a pharmacokinetic profile resembling that of albumin in the circulation. Albiglutide is currently being investigated by GlaxoSmithKline for treatment of type 2 diabetes. Albiglutide may have a half-life of about four to seven days after administration (Matthews et al. 2008).

Taspoglutide

A GLP1 agonist of the embodiments may be taspoglutide (R1583). Taspoglutide a glucagon-like peptide-1 analog that is the 8-(2-methylalanine)-35-(2-methylalanine)-36-L-argininamide derivative of the amino acid sequence 7-36 of human glucagon-like peptide I. Taspoglutide is a long-acting GLP1 analog in which amino acids 8 and 35 of the native GLP1 peptide are substituted with aminoisobutyric acid to prevent DPP-IV and protease-mediated cleavage at the N- and C-terminus, respectively. R1583 may be formulated as a zinc-based drug to prolong its PK activity. Various dosages of taspoglutide may be administered to a patient, e.g., 1-30 mg s.c. Taspoglutide is manufactured by Ipsen and Roche.

Taspoglutide is further described in Nauck et al. (2009), which is herein incorporated by reference in its entirety.

Lixisenatide

Lixisenatide (AVE0010) is a GLP1 agonist that may be used according to the present embodiments. Lixisenatide is an exendin-4-based GLP1 receptor agonist that exhibits approximately 4-fold greater affinity for the human GLP1 receptor compared with native GLP1. Lixisenatide may be administered to a subject, e.g., once or twice a day. In some embodiments, metformin and/or SU therapy may be administered in combination with a GLP1 agonist such as, e.g., Lixisenatide. Lixisenatide may be administered at a dosage of, e.g., about 5-20 micrograms (mcg)/injection. The half-life of AVE0010 may range from about 2.5 to 4 hours. Clinical trials have indicated that lixisenatide can significantly improve glycaemic control in mildly hyperglycaemic patients with Type 2 diabetes on metformin (Ratner et al. 2010).

DPP-4 Inhibitors

In some aspects embodiments a DPP-4 inhibitor is administered to a subject in conjunction with a PKI pathway inhibitor. Likewise, some aspects of the embodiments concern treatment of subjects who are resistant to a DPP-4 inhibitor therapy. In general DPP-4 inhibitors function by increasing incretin levels (GLP1 and GIP agonist levels), which inhibit glucagon release increase insulin secretion, decrease gastric emptying, and decrease blood glucose levels. Importantly, most DPP-4 inhibitors can be administered orally. Examples of DPP-4 inhibitors for use according to the embodiments include, without limitation, Sitagliptin (Januvia/MK-0431), Vildagliptin (Galvus), Saxagliptin (Onglyza), Linagliptin, Anagliptin, Teneligliptin, Alogliptin, Gemigliptin and Dutogliptin.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The Role of CREB Signaling in Beta Cell Dysfunction

The second messenger cAMP has been shown to mediate effects of incretin hormones, in part through induction of the Ser/Thr protein kinase PKA. Blocking cAMP signaling in beta cells through targeted disruption of the Gsa subunit of the heterotrimeric G protein leads to severe glucose intolerance and beta cell apoptosis (Xie et al., 2007). Conversely, mutations that increase PKA activity, either via disruption of the R1α regulatory subunit (Song et al., 2011) or via a gain of function mutation in the PKA catalytic subunit (Kaihara et al., 2013), enhances insulin secretion.

cAMP promotes cellular gene expression via the PKA-mediated phosphorylation of the CREB family of activators and via the de-phosphorylation of the cAMP Regulated Transcriptional Coactivators (CRTCs). Following its activation, CREB has been found to promote islet function in part by upregulating the insulin receptor substrate 2 (IRS2) in beta cells (Jhala et al., 2003) (Park et al., 2006). Although deletion of the single family member CREB1 alone has no effect on beta cell function under normal chow conditions (Shin et al., 2014), expression of a dominant negative CREB polypeptide A-CREB, which blocks all three family members (CREB1, ATF1, CREM), leads to severe hyperglycemia due in part to reductions in glucose stimulated insulin secretion (Jhala et al., 2003).

IRS2-dependent increases in insulin signaling are thought to promote islet growth through the activation of mTORC1 complexes and subsequent induction of the hypoxia inducible factor HIF1 (Van de Velde et al., 2011) (Gunton et al., 2005). Although the mTORC1-HIF pathway appears to be critical for adaptive expansion of pancreatic islet mass, beta cell function deteriorates in the setting of chronic insulin resistance (Zhao et al., 1998). Based on the ability for GLP1 agonists to improve beta cell function in this setting, the inventors examined the potential role of CREB and CRTC2 in mediating these effects.

Exposure of INS1 insulinoma cells to the cAMP agonist Forskolin (FSK) promoted the phosphorylation of CREB at Ser133 and the dephosphorylation of CRTC2 within 30 minutes (FIG. 1a). By contrast, exposure to depolarizing concentrations of KCl (40 mM) stimulated CREB phosphorylation to a lesser extent. Under basal conditions, CRTC2 was sequestered in the cytoplasm of beta cells from cultured islets; exposure to FSK triggered CRTC2 nuclear translocation (FIG. 1b).

Figure 6:
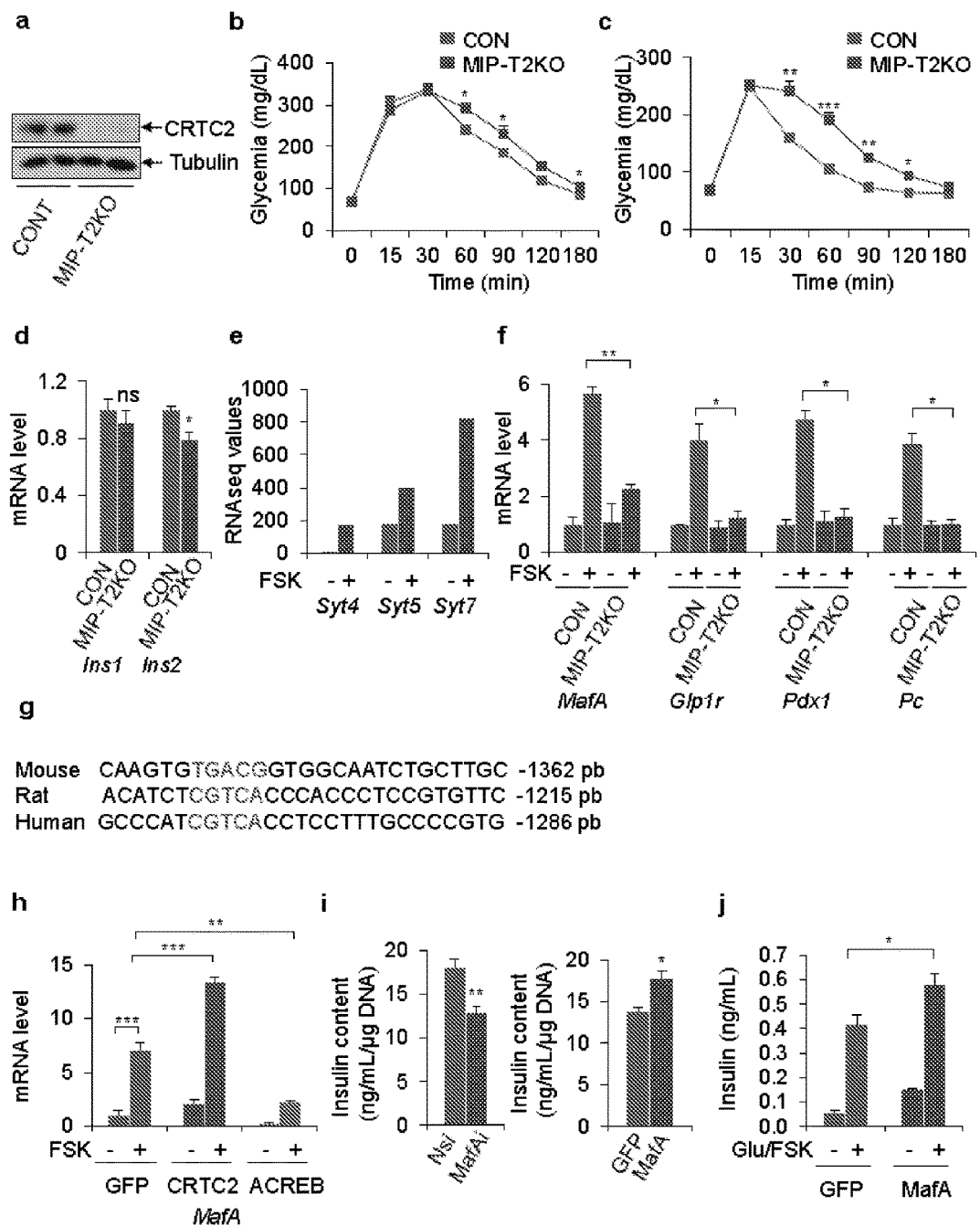
FIG. 6: The CREB Coactivator CRTC2 Stimulates MafA Expression. The CREB coactivator CRTC2 stimulates the expression of MafA and beta cell maturity genes in response to cAMP. a. CRTC2 expression in control versus MIP-T2KO (the higher plot, indicated by filled black squares) islets. b. Intra-peritoneal glucose tolerance testing (IPGTT) of mice with a knockout of CRTC2 in beta cells (MIP2-T2KO) relative to control littermates (*p<0.05; n=8). c. Effect of exendin-4 administration on IPGTT test in MIP-T2KO mice compared to control littermates (*p<0.05; p<0.01, *p<0.001. n=8). d. Quantitative-RT PCR analysis of Ins1 and Ins2 mRNA amounts in pancreatic islets from control and MIP-T2KO mice (*p<0.05, **p<0.01; n=5). e. RNAseq values showing Syt 4, 5 and 7 induction by FSK. f. Effect of FSK exposure on mRNA amounts for MafA and its target genes (G1p1r, Pdx1, Pc) in pancreatic islets from MIP-T2KO or control littermates (*p<0.05, p<0.01. n=6). g. Sequences of CREB binding sites in mouse (SEQ ID NO. 77), rat (SEQ ID NO. 78), and human (SEQ ID NO. 79) MafA gene promoters. h. Effect of CRTC2 or A-CREB over-expression on MafA mRNA amounts in INS1 cells (p<0.01, ***p<0.001. n=6). i. Effect of MafA knockdown (left) or over-expression (right) on insulin content in INS1 cells (*p<0.0, **p<0.01. n=6). j. Effect of MafA over-expression on insulin secretion in INS1 cells. Exposure to FSK indicated (*p<0.05. n=6).

GLP1 and other incretin hormones are released from intestinal cells only following nutrient ingestion (Hoist et al., 2011), so the inventors analysed effects of oral glucose tolerance testing (OGTT) in mice with a beta cell specific knockout of CRTC2 (MIP-T2KO; FIG. 6a). Although they were almost comparable to control littermates by intraperitoneal glucose tolerance test (IPGTT), MIP-T2KO mice showed impaired glucose tolerance by OGTT test (FIG. 1c; FIG. 6b). Indeed, similar differences between control and MIP-T2KO mice were observed following intra-peritoneal (IP) injection of exendin-4 in addition to glucose (FIG. 6c). Arguing against an increase in insulin resistance, circulating glucose concentrations decreased identically in MIP-T2KO mice and control littermates following insulin administration (FIG. 1d). Rather, MIP-T2KO mice secreted less insulin in response to oral glucose gavage, suggesting that beta cell function is disrupted in these animals (FIG. 1E).

The inventors evaluated effects of CRTC2 on insulin secretion from cultured islets in response to cAMP. Following 10 minutes exposure to exendin-4 plus high glucose (20 mM), insulin release from MIP-T2KO islets was reduced 30% (FIG. 1f) relative to control islets. Exposure to glucose alone stimulated insulin secretion comparably in cultured islets from wild-type and MIP-T2KO mice (FIG. 1f). Insulin (Ins1, Ins2) gene expression and protein content were also modestly decreased in MIP-T2KO islets (FIG. 1g; FIG. 6d). Conversely, over-expression of CRTC2 in INS1 insulinoma cells enhanced insulin secretion in response to GLU/FSK. These effects were blocked by expression of a dominant negative CREB polypeptide called A-CREB (FIG. 1h).

Transcriptome-wide studies were performed to identify CREB target genes that promote insulin expression and secretion. This analysis revealed a number of FSK-inducible genes that contain CREB binding sites and that are down-regulated following expression of A-CREB inhibitor. Amongst these, the inventors identified MafA, a beta cell restricted factor that regulates the expression of insulin and a number of genes associated with beta cell maturity and insulin exocytosis (Abdulahad et al., 2012; Lee et al., 2014;

Martin et al., 2012; Selmi, 2012; Tu et al., 2012) (FIG. 2a; Table 1). In addition, exposure to FSK also stimulated the expression of a subset of synaptotagmins (Syt4, Syt5, Syt7), proteins that function as major calcium sensors for synaptic vesicles (Iezzi et al., 2004; Iezzi et al., 2005) (FIG. 6e).

TABLE 1

RNAseq values and fold inductions in INS1 cells infected with ACREB compared to GFP and stimulated with FSK.

| Gene | GFP control | FSK | fold | ACREB control | FSK | fold |
|---|---|---|---|---|---|---|
| MafA | 54.2 | 474.4 | 8.7 | 24.4 | 90.2 | 3.7 |
| Nr4a2 | 1.9 | 106.5 | 56.6 | 0.9 | 5.5 | 6.3 |
| Diras2 | 45.2 | 519.7 | 11.5 | 64.1 | 109.5 | 1.7 |
| Irs2 | 50.3 | 289.9 | 5.6 | 16.5 | 38.8 | 2.3 |

Figure 2:
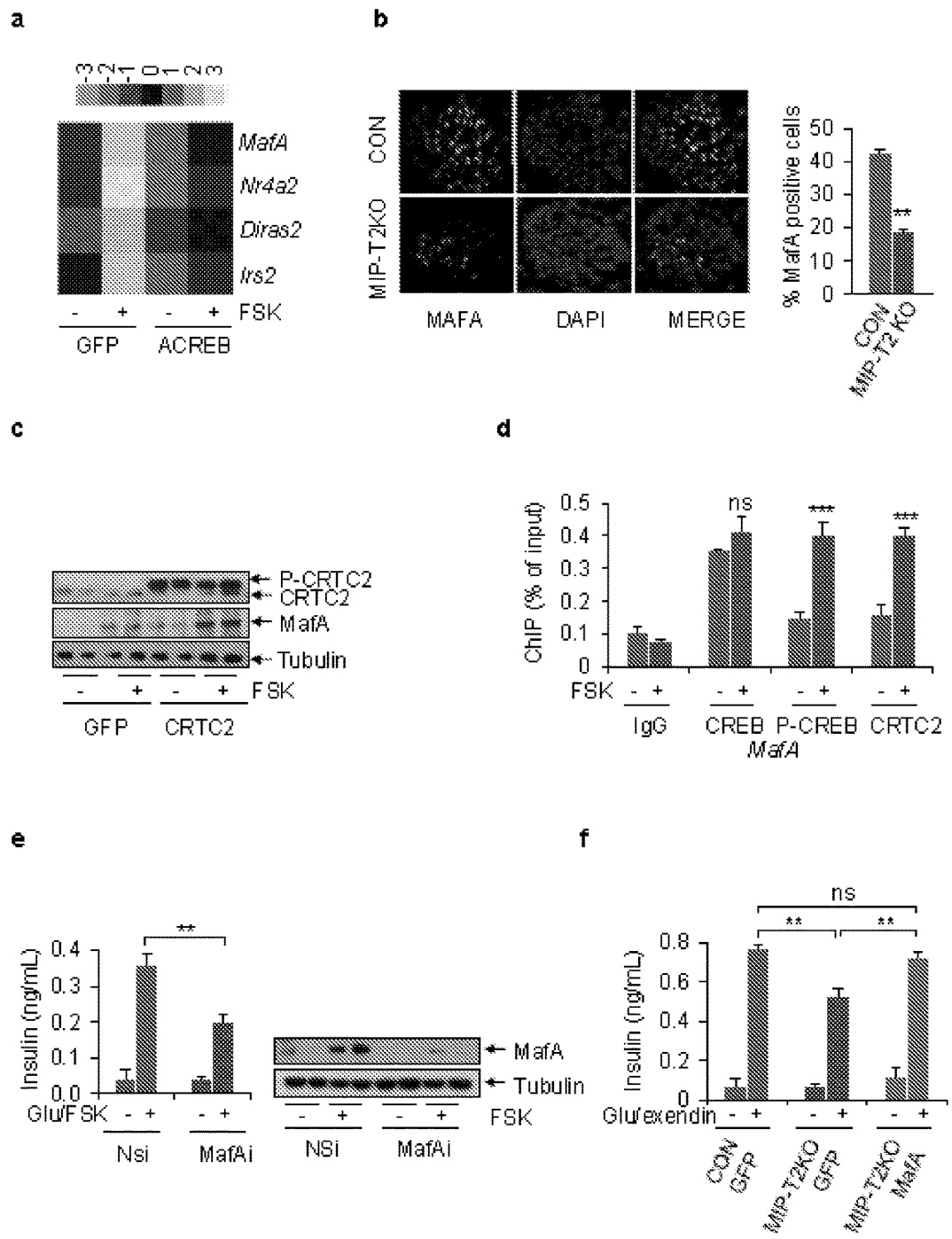
FIG. 2: CRTC2 Stimulates MafA Expression. a. RNAseq analysis of INS1 cells exposed to FSK. Top genes upregulated 2-fold or better indicated. Effect of dominant negative A-CREB expression shown. b Immunohistochemical assay of MafA staining in islets from pancreatic sections of control and MIP-T2KO mice. Right, relative number of MafA positive cells in control and MIP-T2KO sections shown ($p<0.01$; n=5). c. Effect of CRTC2 over-expression on MafA protein amounts in INS1 cells. Exposure to FSK indicated. d. Chromatin immunoprecipitation (ChIP) assay of INS1 cells showing amounts of CREB and CRTC2 recruited to the MafA promoter under basal conditions and following exposure to FSK (*$p<0.001$; n=6). e. Effect of MafA depletion on insulin secretion from INS1 cells (*$p<0.05$, $p<0.01$; n=6). f. Effect of adenoviral GFP control or MafA over-expression on insulin secretion from MIP-T2KO mice islets compared to control ($p<0.01$; n=6). Data are shown as mean±s.e.m.

Realizing the importance of MafA for insulin expression and secretion, the inventors addressed the potential role of this transcription factor in mediating effects of CREB on beta cell function. Exposure of isolated mouse islets to FSK increased the expression of MafA (FIG. 6f) which promote beta cell maturation. Indeed, islet MafA expression was reduced by two-thirds in pancreatic islets from MIP-T2KO mice relative to control animals by immunohistochemical analysis (FIG. 2b). As a result, beta cell maturity gene expression (Glp1r, Pc, Pdx1) was also down-regulated in CRTC2 mutant islets (FIG. 6f). Conversely, CRTC2 over-expression in INS1 cells increased MafA expression (FIG. 2c).

It was evaluated whether MafA is a direct target gene for CREB and CRTC2. Supporting this notion, the MafA promoter contains a consensus cAMP response element (CRE) that is constitutively occupied by CREB in INS1 cells (FIG. 2d, FIG. 6g). In line with its cytoplasmic sequestration in unstimulated cells (Screaton et al., 2004), amounts of CRTC2 over the MafA promoter were low under basal conditions but increased following FSK treatment, when CRTC2 is translocated to the nucleus. Inhibiting CREB occupancy, through A-CREB over-expression, down-regulated MafA gene in INS1 cells (FIG. 6h).

It was also tested whether MafA activity contributes to cAMP-dependent increases in insulin secretion. In line with this notion, RNAi-mediated depletion of MafA decreased insulin content and secretion from INS1 cells while MafA over-expression increased them (FIG. 2e; FIGS. 6i and 6j). Indeed, adenoviral expression of MafA restored insulin secretion to wild-type levels in CRTC2 mutant pancreatic islets exposed acutely to glucose plus exendin (FIG. 2f). Taken together, these results demonstrate that CRTC2 promotes beta cell function in part by upregulating MafA in response to cAMP.

Figure 7:
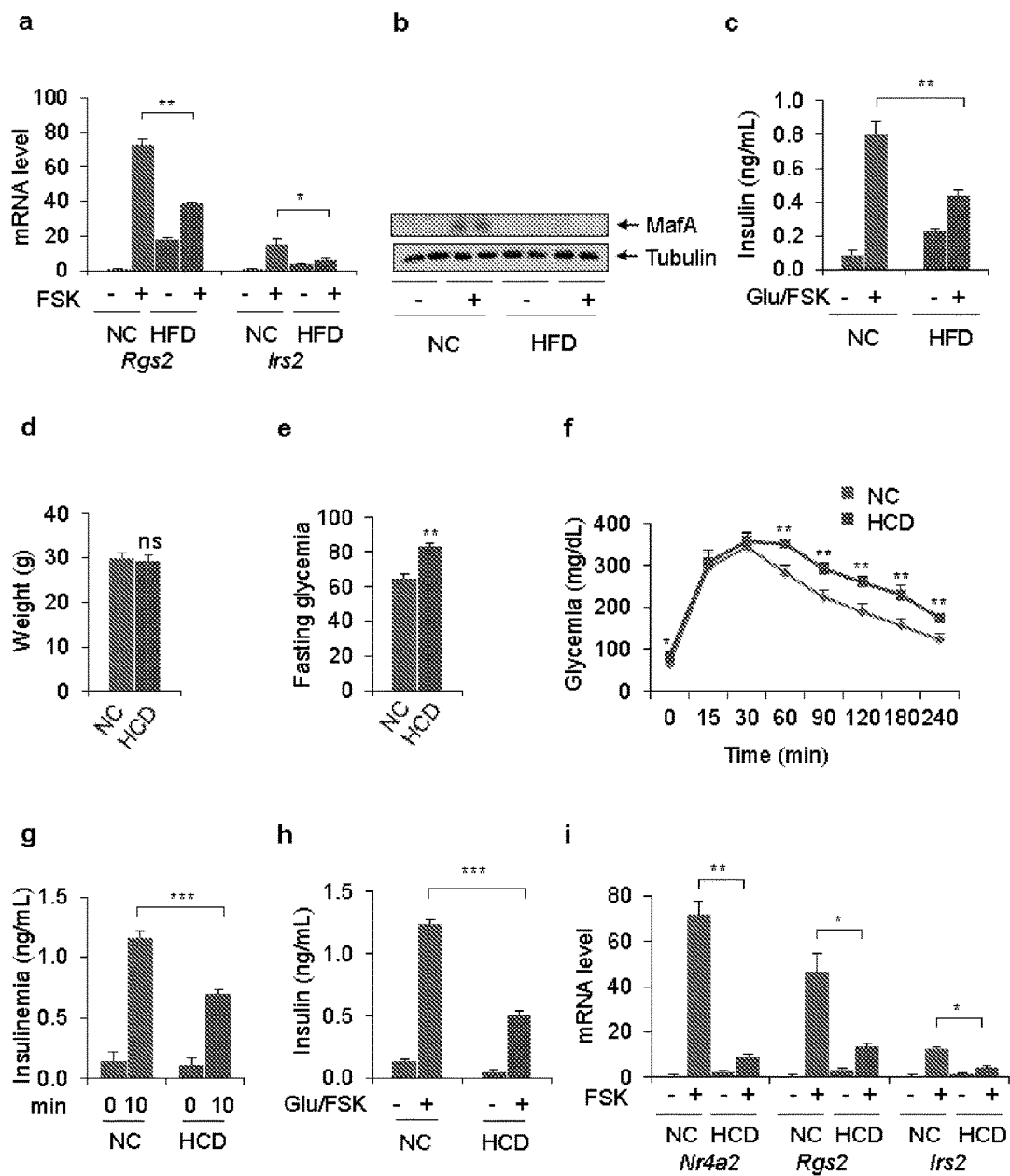
FIG. 7: High Fat and Carbohydrate Diets Disrupt CREB Activity in beta cells. High fat diet and high carbohydrate diets reduce CREB activity and insulin secretion in response to cAMP agonist by promoting PKIB expression in beta cells. a. Q-PCR analysis of mRNAs for CREB target genes (Rgs2, Irs2) in cultured pancreatic islets from NC or HFD fed mice (*p<0.05, p<0.01. n=4). b. Protein amounts for MafA in NC vs. HFD islets. c. Effect of GLU/FSK on insulin secretion from pancreatic islets of HFD compared to NC fed mice (p<0.01. n=4). Effect of HCD feeding on body weight (d), fasting glucose (e) and glucose tolerance (f) (p<0.01. n=5). HCD plot in FIG. 7f is the higher plot, indicated by filled black squares. g. Circulating concentrations of insulin 10 minutes following oral glucose administration (*p<0.001. n=5). h. Insulin secretion from cultured islets harvested from NC or HCD fed mice (***p<0.001. n=3). i. mRNA amounts for CREB target genes exposed to FSK as indicated (*p<0.05, **p<0.01. n=3).

Although initially compensated by an increase in pancreatic islet mass, prolonged insulin resistance causes an impairment in beta cell function that is thought to reflect the down-regulation of certain beta cell factors including MafA. Having seen that CREB and CRTC2 promote MafA expression in response to cAMP signals, the effects of insulin resistance on this pathway in pancreatic islets were tested. By contrast with the robust upregulation of MafA and other CREB target genes by FSK in pancreatic islets from lean mice, FSK had only modest effects on islets from high fat diet (HFD) mice (FIG. 3a; FIGS. 7a and 7b). Similarly, effects of FSK on insulin secretion were attenuated in HFD islets relative to control (FIG. 7c). In principle, the loss of CREB activity in HFD fed mice could reflect chronic increases in a number of nutrients including circulating glucose or free fatty acids. To test the role of hyperglycemia in this process, high carbohydrate diet (HCD) feeding studies were performed. Although it had no effect on body weight, HCD feeding impaired glucose tolerance and insulin secretion after only 8 weeks (FIGS. 7d-7g). Similar to islets from HFD mice, pancreatic islets from HCD animals showed only modest increases in insulin secretion and CREB target gene expression following exposure to FSK (FIGS. 7h and 7i).

Figure 3:
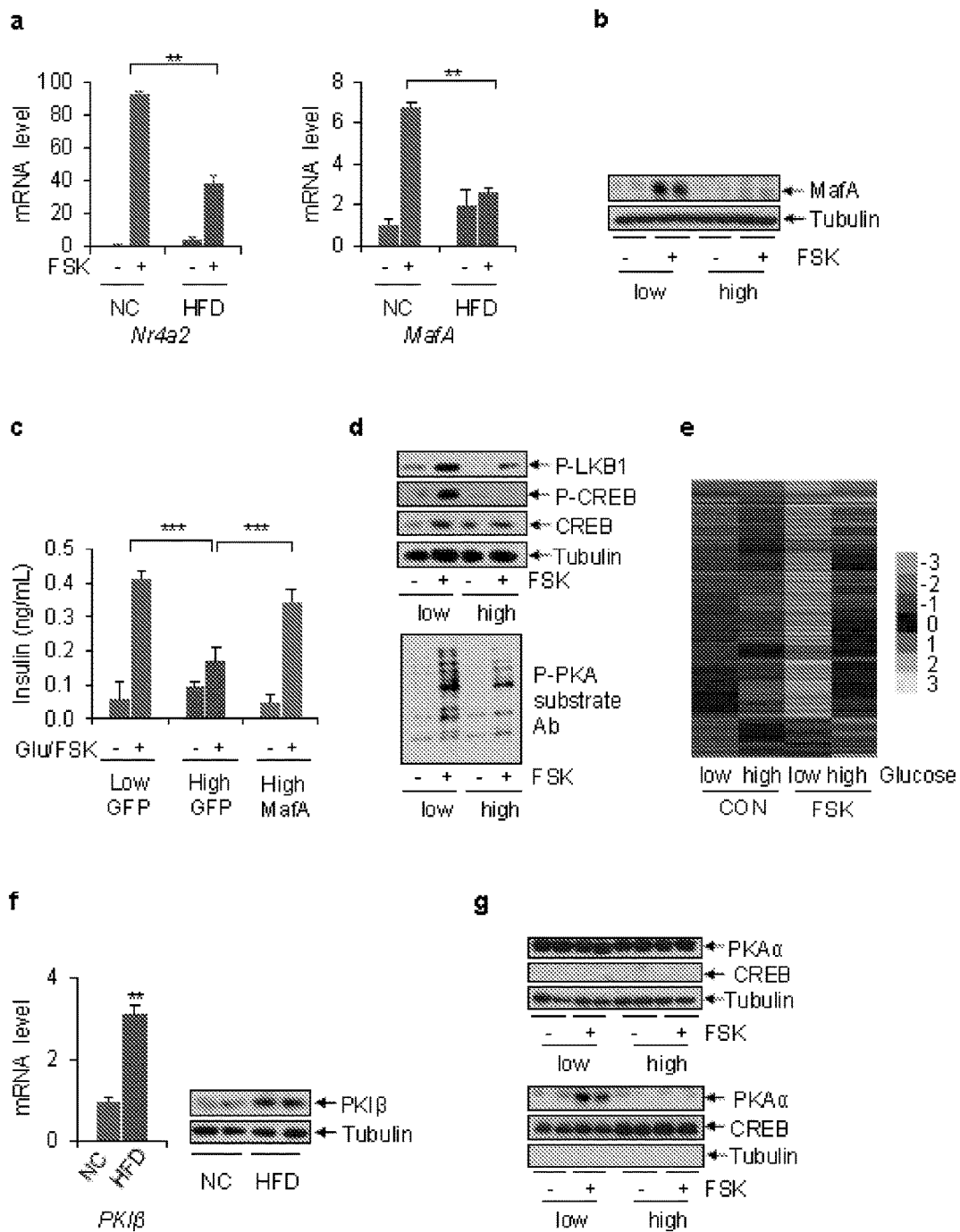
FIG. 3: Disruption of the Beta cell CREB Pathway in chronic hyperglycemia. a. Relative induction of CREB target genes by FSK in cultured pancreatic islets from normal chow (NC) or high fat diet (HFD) fed mice. mRNA amounts for NR4A2 and MafA shown ($p<0.01$; n=6). b. Effect of prolonged exposure to high glucose on FSK-induced increases in MafA protein amounts. c. Effect of chronic high glucose and adenoviral MafA expression on insulin secretion from INS1 cells (*$p<0.001$; n=6). d. Immunoblots showing effect of prolonged high glucose exposure on CREB phosphorylation (left) and on cellular PKA activity (right) in primary cultured mouse islets exposed to FSK. Effect of glucose on phosphorylation of LKB1 at a consensus PKA site (Ser431) also shown. e. RNAseq analysis of INS1 cells showing effect of prolonged exposure to high glucose on downregulation of cAMP inducible genes. Effect of FSK shown. f. Effect of high fat diet (HFD) feeding on PKIB mRNA (left) and protein expression (right) in mouse islets (**p<0.01; n=4). g. Effect of chronic high glucose treatment on nuclear shuttling of PKA catalytic subunit in INS1 cells exposed to FSK. Cytoplasmic (top) and nuclear (bottom) fractions shown. Data are shown as mean±s.e.m.
Figure 8:
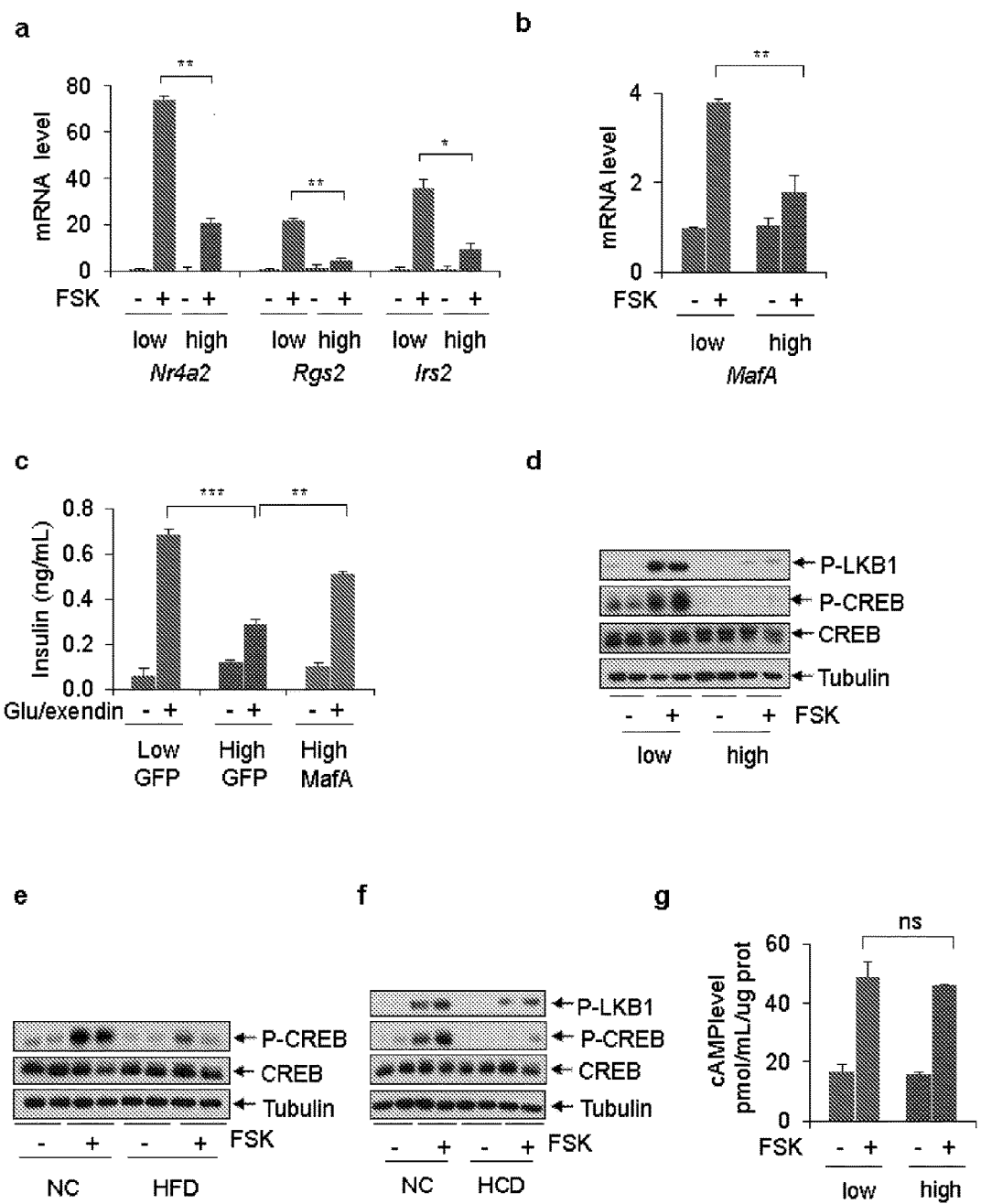
FIG. 8: Effects of prolonged exposure to high glucose on CREB Activity. Prolonged exposure to high glucose disrupts CREB activity. Effect of chronic incubation (72 hours) in low (2.8 mM) or high (20 mM) glucose on mRNA amounts for CREB target genes (a) and MafA (b) in cultured pancreatic islets. Exposure to FSK indicated (*p<0.05, p<0.01. n=6). c. Effect of chronic high glucose exposure and adenoviral MafA expression on insulin secretion from cultured pancreatic islets. Exposure to glucose/exendin indicated (p<0.01,***p<0.001. n=6) d.-f. Immunoblots of phospho-CREB showing effects of chronic exposure to high glucose (d) as well as HFD or HCD feeding (e and f) on phosphorylation of CREB in primary cultured islets exposed to FSK (n=4). g. Effect of chronic glucose exposure on cAMP accumulation in INS1 cells exposed to FSK (n=6).

It was considered whether exposure of cultured pancreatic islets to high concentrations of glucose mimics effects of hyperglycemia on the CREB pathway. Supporting this idea, prolonged exposure of either INS1 cells or cultured pancreatic islets to high glucose (20 mM, 72 hours) inhibited the expression of MafA and other CREB target genes in cells exposed to FSK (FIG. 3b; FIGS. 8a and 8b). Exposure to 10 mM glucose was not sufficient for PKIB induction in INS1 cells. Indeed, FSK-dependent increases in insulin secretion were substantially down-regulated in INS1 cells exposed to high-glucose and FSK (FIG. 3c). The impairment in insulin secretion under chronic high glucose conditions was partially rescued by MafA over-expression in both INS1 cells and primary islets (FIG. 3c; FIG. 8c).

The mechanism by which high glucose exposure attenuates CREB activity was addressed. Although total amounts of CREB were unchanged, high glucose treatment disrupted the FSK-induced phosphorylation of CREB in both INS1 cells and pancreatic islets (FIG. 3d; FIG. 8d). Moreover, phospho-CREB amounts were also down-regulated in cultured islets from HFD and HCD mice (FIGS. 8e and 8f) Arguing against an effect on adenyl cyclase or phosphodiesterase activities, exposure to FSK increased intracellular cAMP concentrations comparably in control and high glucose treated INS1 cells (FIG. 8g). Rather, cellular PKA activity was substantially reduced in islets chronically exposed chronic glucose, as visualized in immunoblot assays with phospho-PKA substrate antiserum (FIG. 3d). Consistent with its effects on CREB phosphorylation, prolonged exposure of INS1 cells to high glucose largely inhibited the induction of cAMP responsive genes (FIG. 3e, table 2 below).

TABLE 2

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Nr4a3 | 0.3 | 262.9 | 1027.3 | 2.0 | 143.1 | 70.9 |
| LOC100360880 | 0.4 | 161.1 | 457.6 | 0.3 | 68.0 | 252.0 |
| Fosl2 | 3.7 | 1544.0 | 422.9 | 31.0 | 728.4 | 23.5 |
| Gprc5a | 0.1 | 26.9 | 349.8 | 1.1 | 41.5 | 36.6 |
| Fam46b | 0.4 | 126.6 | 295.8 | 0.1 | 3.1 | 26.6 |
| Rgs2 | 0.9 | 226.2 | 255.8 | 1.5 | 38.8 | 25.1 |
| Rxfp3 | 0.3 | 70.6 | 202.4 | 2.5 | 143.5 | 57.0 |
| Actn2 | 1.2 | 225.6 | 183.9 | 4.2 | 45.1 | 10.8 |
| Ccnd1 | 0.5 | 86.5 | 174.5 | 2.5 | 57.6 | 23.4 |
| Kdr | 0.3 | 41.3 | 163.7 | 0.4 | 32.3 | 86.5 |
| Tac1 | 1.0 | 132.8 | 137.2 | 1.0 | 15.7 | 15.3 |
| Fos | 1.2 | 155.4 | 125.7 | 2.6 | 73.8 | 28.2 |
| Penk | 0.1 | 7.0 | 122.4 | 0.8 | 3.1 | 3.9 |
| Sik1 | 4.7 | 517.2 | 111.0 | 11.0 | 269.4 | 24.5 |
| Thbs1 | 0.2 | 25.1 | 107.3 | 0.3 | 6.2 | 24.3 |
| Sphk1 | 0.1 | 7.3 | 104.5 | 0.1 | 2.9 | 38.0 |
| Gpr135 | 0.1 | 12.5 | 102.2 | 0.1 | 1.8 | 18.5 |
| Crem | 7.7 | 738.5 | 95.5 | 23.0 | 375.1 | 16.3 |
| Mest | 30.6 | 2748.9 | 89.9 | 152.7 | 3255.2 | 21.3 |
| Klf4 | 1.7 | 146.2 | 86.8 | 2.1 | 55.3 | 26.2 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Sv2c | 0.5 | 43.4 | 86.3 | 1.0 | 22.5 | 21.6 |
| Ntsr1 | 0.1 | 7.7 | 75.1 | 0.0 | 0.2 | 5.9 |
| Dlx2 | 0.2 | 12.7 | 71.0 | 0.9 | 12.5 | 14.3 |
| Cartpt | 1.6 | 104.6 | 66.8 | 4.1 | 35.0 | 8.6 |
| Snai3 | 0.1 | 3.3 | 64.6 | 0.2 | 1.1 | 5.3 |
| Nr4a1 | 10.2 | 604.2 | 59.5 | 18.9 | 266.3 | 14.1 |
| Maff | 2.4 | 136.4 | 56.2 | 5.5 | 37.0 | 6.8 |
| Nr4a2 | 2.1 | 117.0 | 55.4 | 2.6 | 32.4 | 12.6 |
| Pdzrn3 | 0.7 | 36.7 | 55.3 | 0.6 | 20.5 | 33.0 |
| aicda | 0.0 | 1.6 | 52.6 | 0.0 | 0.0 | |
| Tgfb2 | 1.3 | 63.9 | 50.6 | 0.3 | 5.7 | 17.3 |
| Cyp1b1 | 0.0 | 1.7 | 48.6 | 0.1 | 0.9 | 14.8 |
| Prdm1 | 0.2 | 9.7 | 48.1 | 0.8 | 2.2 | 2.8 |
| Ppargc1a | 1.6 | 76.7 | 47.1 | 7.2 | 51.6 | 7.1 |
| Cebpd | 6.2 | 280.9 | 45.5 | 3.7 | 117.9 | 31.6 |
| Dennd2c | 0.1 | 2.5 | 40.9 | 2.0 | 3.7 | 1.8 |
| LRRTM1 | 0.2 | 8.4 | 39.8 | 0.3 | 1.3 | 4.0 |
| Sstr1 | 3.4 | 127.5 | 37.9 | 2.8 | 27.9 | 9.9 |
| Zhx2 | 1.2 | 45.9 | 37.0 | 1.2 | 7.4 | 6.4 |
| Pard6a | 4.6 | 161.4 | 35.4 | 6.5 | 32.1 | 4.9 |
| Cd83 | 4.2 | 144.5 | 34.6 | 3.8 | 9.9 | 2.6 |
| Atf3 | 1.8 | 62.1 | 34.1 | 4.6 | 23.2 | 5.0 |
| LOC689986 | 54.7 | 1723.5 | 31.5 | 71.1 | 475.1 | 6.7 |
| Hbegf | 4.0 | 124.3 | 31.2 | 56.1 | 193.7 | 3.5 |
| Tf | 0.0 | 1.1 | 31.0 | 0.1 | 0.4 | 3.3 |
| Gja4 | 0.5 | 15.9 | 30.8 | 0.8 | 2.2 | 2.6 |
| Mustn1 | 13.4 | 401.2 | 29.8 | 27.9 | 80.9 | 2.9 |
| Fosl1 | 0.7 | 21.3 | 29.1 | 0.7 | 14.9 | 21.9 |
| Diras2 | 40.1 | 1160.4 | 28.9 | 22.4 | 598.8 | 26.7 |
| Adamts4 | 0.0 | 1.3 | 28.4 | 0.0 | 0.2 | 10.3 |
| Cwc25 | 8.3 | 210.9 | 25.5 | 7.4 | 21.1 | 2.9 |
| Dgcr6 | 23.2 | 588.4 | 25.3 | 34.3 | 92.3 | 2.7 |
| Csrnp1 | 4.0 | 100.0 | 24.9 | 3.6 | 43.8 | 12.2 |
| Dio2 | 0.2 | 5.5 | 24.8 | 0.7 | 3.2 | 4.6 |
| Plk2 | 1.3 | 30.9 | 23.6 | 4.3 | 52.0 | 12.0 |
| Frmd6 | 0.0 | 1.1 | 23.4 | 0.1 | 1.7 | 14.1 |
| Id4 | 10.5 | 244.8 | 23.3 | 17.5 | 147.3 | 8.4 |
| Ahsg | 0.1 | 1.4 | 22.9 | 0.1 | 0.1 | 1.0 |
| Prr18 | 0.1 | 2.2 | 22.7 | 0.0 | 0.7 | |
| Nap1l5 | 12.1 | 271.0 | 22.4 | 10.9 | 88.7 | 8.2 |
| Bmp2 | 0.7 | 14.9 | 22.0 | 2.6 | 8.4 | 3.2 |
| Lfng | 0.4 | 8.4 | 21.4 | 2.0 | 10.1 | 5.0 |
| Calcr | 0.0 | 0.5 | 20.9 | 0.2 | 1.5 | 7.2 |
| Cck | 24.4 | 506.0 | 20.8 | 65.6 | 380.4 | 5.8 |
| Ypel4 | 19.6 | 402.7 | 20.5 | 8.4 | 58.6 | 7.0 |
| Ccdc85a | 0.1 | 1.9 | 20.2 | 0.4 | 1.2 | 3.1 |
| Rhbdf1 | 0.9 | 18.2 | 19.8 | 1.1 | 4.4 | 3.9 |
| Metrnl | 0.2 | 4.7 | 19.2 | 1.2 | 4.6 | 3.8 |
| Pappa | 0.2 | 4.0 | 19.0 | 0.3 | 4.7 | 18.0 |
| Grk1 | 0.1 | 1.4 | 18.9 | 0.0 | 0.0 | |
| Hpd | 0.1 | 1.2 | 18.8 | 0.2 | 0.1 | 0.7 |
| Hhip | 0.6 | 11.2 | 18.4 | 0.7 | 5.7 | 8.7 |
| Ankrd34c | 0.1 | 2.3 | 18.2 | 0.3 | 4.4 | 15.7 |
| Gem | 11.0 | 195.9 | 17.9 | 8.7 | 52.8 | 6.1 |
| Sipa1l2 | 3.2 | 56.4 | 17.8 | 2.3 | 9.2 | 4.0 |
| Junb | 17.5 | 307.6 | 17.6 | 31.7 | 155.6 | 4.9 |
| Vtcn1 | 0.0 | 0.5 | 17.5 | 0.0 | 0.7 | 28.0 |
| Fgl2 | 4.6 | 78.3 | 17.0 | 1.5 | 16.3 | 10.8 |
| Cry2 | 25.2 | 423.2 | 16.8 | 30.7 | 314.1 | 10.2 |
| Padi4 | 0.2 | 4.1 | 16.8 | 0.9 | 4.6 | 5.4 |
| RGD1564664 | 14.3 | 236.8 | 16.6 | 5.7 | 41.6 | 7.3 |
| Plk3 | 8.9 | 146.2 | 16.4 | 8.6 | 36.7 | 4.3 |
| Lrrtm2 | 0.8 | 13.0 | 16.4 | 0.2 | 1.3 | 7.3 |
| Nedd9 | 8.2 | 133.9 | 16.3 | 6.3 | 70.4 | 11.1 |
| Calca | 0.4 | 6.2 | 16.2 | 1.1 | 1.2 | 1.1 |
| Nfil3 | 16.5 | 261.9 | 15.8 | 16.6 | 82.6 | 5.0 |
| Nptx1 | 2.3 | 36.3 | 15.7 | 4.5 | 22.1 | 4.9 |
| Lrrc10b | 3.0 | 46.9 | 15.7 | 1.5 | 18.0 | 11.7 |
| Cldn23 | 0.7 | 10.0 | 15.2 | 1.7 | 6.9 | 4.1 |
| Rnf39 | 0.9 | 13.2 | 15.1 | 0.8 | 7.2 | 9.2 |
| C1s | 0.1 | 0.8 | 14.9 | 0.0 | 0.3 | |
| Rcan1 | 31.5 | 467.1 | 14.8 | 65.1 | 134.3 | 2.1 |
| Egr4 | 1.0 | 15.0 | 14.6 | 1.4 | 20.6 | 14.6 |
| Ecel1 | 0.2 | 3.5 | 14.3 | 0.1 | 0.5 | 4.3 |
| C3 | 0.0 | 0.4 | 14.2 | 0.0 | 0.1 | 2.5 |
| Amotl2 | 0.3 | 3.9 | 14.1 | 0.2 | 1.0 | 6.2 |
| Asb4 | 1.1 | 15.4 | 14.1 | 2.7 | 20.2 | 7.5 |
| Giot1 | 0.9 | 13.2 | 14.1 | 0.9 | 14.2 | 16.1 |
| Gpr88 | 0.2 | 2.3 | 14.0 | 2.4 | 14.2 | 5.8 |
| Lmo7 | 9.9 | 137.8 | 14.0 | 45.0 | 123.7 | 2.7 |
| Slc4a11 | 0.5 | 7.6 | 13.9 | 0.4 | 1.8 | 4.7 |
| St8sia1 | 3.1 | 42.3 | 13.5 | 0.9 | 5.3 | 5.7 |
| Syt4 | 13.1 | 176.3 | 13.5 | 25.6 | 105.0 | 4.1 |
| Gpr180 | 10.5 | 140.8 | 13.5 | 9.9 | 29.8 | 3.0 |
| Cxcr7 | 6.4 | 86.1 | 13.4 | 2.4 | 39.1 | 16.1 |
| Slc25a25 | 41.9 | 561.2 | 13.4 | 43.2 | 428.6 | 9.9 |
| Runx1 | 17.1 | 225.7 | 13.2 | 13.9 | 143.9 | 10.3 |
| Atoh7 | 1.1 | 14.9 | 13.1 | 1.6 | 5.1 | 3.2 |
| Cd7 | 2.2 | 28.9 | 13.1 | 0.5 | 2.7 | 5.1 |
| Klhl15 | 1.7 | 21.2 | 12.8 | 2.1 | 2.4 | 1.2 |
| Grb10 | 0.1 | 1.3 | 12.8 | 0.1 | 1.2 | 12.3 |
| Pde4a | 1.8 | 22.8 | 12.7 | 0.7 | 3.0 | 4.1 |
| Depdc7 | 0.9 | 10.7 | 12.5 | 0.7 | 4.4 | 6.7 |
| Slc7a11 | 0.3 | 3.9 | 12.4 | 1.0 | 4.6 | 4.6 |
| Sema3a | 0.6 | 7.1 | 12.4 | 1.7 | 8.1 | 4.7 |
| B3galt2 | 2.9 | 36.1 | 12.3 | 3.8 | 10.1 | 2.7 |
| Ttr | 0.6 | 7.0 | 12.3 | 0.3 | 0.9 | 3.0 |
| Dusp1 | 36.1 | 441.1 | 12.2 | 18.9 | 68.8 | 3.6 |
| Per1 | 19.1 | 232.4 | 12.2 | 20.4 | 94.1 | 4.6 |
| Apoa4 | 0.1 | 1.6 | 12.1 | 0.2 | 0.6 | 2.6 |
| Areg | 0.2 | 1.8 | 12.1 | 0.4 | 0.6 | 1.5 |
| Spry1 | 1.4 | 16.7 | 12.1 | 3.7 | 13.5 | 3.7 |
| Apoc3 | 0.2 | 2.5 | 11.9 | 0.3 | 0.3 | 0.7 |
| Pkp2 | 6.0 | 70.7 | 11.8 | 6.1 | 35.8 | 5.8 |
| Cxcl1 | 0.6 | 6.8 | 11.6 | 0.5 | 2.1 | 4.4 |
| Spata2L | 6.3 | 72.6 | 11.5 | 5.7 | 42.7 | 7.5 |
| Midn | 65.1 | 743.0 | 11.4 | 105.1 | 465.3 | 4.4 |
| Ppp1r17 | 1.4 | 16.0 | 11.4 | 2.1 | 5.0 | 2.3 |
| Cp | 0.0 | 0.2 | 10.8 | 0.2 | 0.4 | 2.3 |
| Apoa1 | 0.2 | 2.2 | 10.7 | 0.4 | 0.9 | 2.1 |
| Pak3 | 11.0 | 116.1 | 10.6 | 20.8 | 96.5 | 4.6 |
| Lrrk2 | 1.8 | 18.5 | 10.3 | 2.8 | 19.3 | 6.8 |
| Rps28 | 0.5 | 5.1 | 10.3 | 1.6 | 3.5 | 2.3 |
| Cpa4 | 0.2 | 2.3 | 10.3 | 0.1 | 0.4 | 3.6 |
| Btg1 | 67.5 | 686.8 | 10.2 | 72.5 | 527.1 | 7.3 |
| Dyrk3 | 5.4 | 55.2 | 10.2 | 4.9 | 16.1 | 3.3 |
| Cyp4a1 | 0.2 | 1.5 | 10.1 | 0.1 | 0.5 | 3.7 |
| Mapkapk2 | 100.8 | 1017.1 | 10.1 | 167.9 | 609.7 | 3.6 |
| Litaf | 62.7 | 631.4 | 10.1 | 115.2 | 359.3 | 3.1 |
| Lyar | 20.9 | 209.6 | 10.0 | 27.9 | 108.1 | 3.9 |
| Akap12 | 33.7 | 338.5 | 10.0 | 11.9 | 17.0 | 1.4 |
| Gadd45b | 12.6 | 126.0 | 10.0 | 19.3 | 61.8 | 3.2 |
| Slc26a2 | 15.9 | 156.2 | 9.8 | 32.5 | 200.4 | 6.2 |
| Inhba | 0.4 | 3.6 | 9.8 | 0.4 | 3.3 | 7.5 |
| Sertad2 | 8.1 | 79.0 | 9.8 | 12.8 | 18.6 | 1.5 |
| Coq10b | 12.5 | 121.9 | 9.7 | 9.3 | 49.3 | 5.3 |
| Zfp36 | 17.5 | 170.7 | 9.7 | 25.9 | 62.7 | 2.4 |
| Aldob | 0.3 | 3.0 | 9.6 | 0.7 | 1.0 | 1.4 |
| Nefl | 4.8 | 46.0 | 9.5 | 1.7 | 12.0 | 7.0 |
| Rasd1 | 27.0 | 256.8 | 9.5 | 11.5 | 14.2 | 1.2 |
| Dok7 | 0.1 | 0.6 | 9.4 | 0.1 | 0.0 | 0.0 |
| Slc23a1 | 0.0 | 0.3 | 9.4 | 0.1 | 0.1 | 0.9 |
| Apoa5 | 0.0 | 0.4 | 9.4 | 0.1 | 0.2 | 2.2 |
| RGD1310507 | 0.1 | 0.6 | 9.4 | 0.1 | 0.0 | 0.0 |
| Bdh2 | 0.1 | 0.7 | 9.4 | 0.5 | 0.5 | 1.0 |
| Epha2 | 0.7 | 6.6 | 9.3 | 2.6 | 17.1 | 6.5 |
| Ngfr | 2.0 | 18.6 | 9.3 | 2.6 | 16.1 | 6.2 |
| Bhlhe22 | 2.1 | 19.5 | 9.3 | 1.3 | 7.4 | 5.8 |
| Hps4 | 35.0 | 325.5 | 9.3 | 17.5 | 91.9 | 5.3 |
| Zfp703 | 9.9 | 91.8 | 9.3 | 5.4 | 52.4 | 9.7 |
| Clp1 | 7.7 | 71.5 | 9.3 | 8.8 | 15.2 | 1.7 |
| Pdxk | 44.3 | 410.6 | 9.3 | 34.9 | 107.2 | 3.1 |
| Mfsd2a | 25.6 | 236.6 | 9.2 | 10.0 | 71.4 | 7.2 |
| Akap3 | 0.2 | 1.5 | 9.2 | 0.4 | 1.1 | 2.6 |
| Gcnt3 | 0.8 | 7.1 | 9.2 | 4.9 | 11.1 | 2.3 |
| Insig1 | 8.5 | 77.3 | 9.0 | 10.3 | 31.8 | 3.1 |
| Fyb | 1.3 | 11.3 | 9.0 | 8.2 | 28.1 | 3.4 |
| Tat | 0.1 | 1.1 | 9.0 | 0.1 | 0.1 | 1.0 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Emd | 60.2 | 536.4 | 8.9 | 56.9 | 247.9 | 4.4 |
| Srxn1 | 31.2 | 277.4 | 8.9 | 23.2 | 154.7 | 6.7 |
| Trim66 | 6.8 | 59.0 | 8.7 | 2.1 | 8.0 | 3.8 |
| Fbn1 | 0.4 | 3.0 | 8.6 | 0.2 | 0.4 | 1.9 |
| Cxcr5 | 1.9 | 16.3 | 8.6 | 1.8 | 2.2 | 1.2 |
| Guca2a | 0.4 | 3.4 | 8.6 | 1.0 | 1.0 | 1.0 |
| Lmo1 | 18.6 | 158.9 | 8.5 | 15.8 | 62.4 | 4.0 |
| Aff4 | 25.3 | 214.6 | 8.5 | 25.2 | 45.1 | 1.8 |
| Hectd2 | 1.3 | 11.2 | 8.5 | 2.1 | 3.8 | 1.9 |
| Stc1 | 51.8 | 437.9 | 8.5 | 20.2 | 172.4 | 8.5 |
| Ncald | 30.6 | 258.1 | 8.4 | 10.9 | 36.3 | 3.3 |
| Lbh | 15.4 | 127.6 | 8.3 | 17.3 | 26.7 | 1.5 |
| Camk4 | 14.9 | 122.7 | 8.3 | 19.2 | 71.3 | 3.7 |
| Ppp1r15a | 28.4 | 233.8 | 8.2 | 31.9 | 116.8 | 3.7 |
| Barhl1 | 28.8 | 236.5 | 8.2 | 17.9 | 54.0 | 3.0 |
| Irs2 | 66.5 | 546.3 | 8.2 | 55.4 | 313.2 | 5.7 |
| Nfkb2 | 8.5 | 69.8 | 8.2 | 10.6 | 34.7 | 3.3 |
| Slc27a2 | 0.0 | 0.2 | 8.1 | 0.0 | 0.0 | |
| Klhl1 | 0.0 | 0.2 | 8.1 | 0.1 | 1.4 | 10.1 |
| Cyp4a2 | 0.0 | 0.3 | 8.1 | 0.0 | 0.0 | |
| Bin2 | 0.1 | 0.7 | 8.1 | 0.0 | 0.2 | |
| Hsd11b1 | 0.1 | 0.4 | 8.1 | 0.0 | 0.0 | |
| Rpl3l | 0.1 | 0.5 | 8.1 | 0.4 | 0.3 | 0.7 |
| Ptgdr2 | 0.1 | 0.5 | 8.1 | 0.5 | 0.2 | 0.3 |
| Slc1a4 | 24.6 | 197.6 | 8.0 | 7.3 | 25.5 | 3.5 |
| Ppp1r11 | 51.0 | 410.1 | 8.0 | 44.2 | 182.1 | 4.1 |
| Rbp4 | 0.8 | 6.5 | 8.0 | 1.2 | 2.0 | 1.6 |
| LOC690137 | 3.5 | 28.1 | 8.0 | 3.3 | 12.1 | 3.6 |
| Otud4 | 15.2 | 120.9 | 7.9 | 20.4 | 84.0 | 4.1 |
| Gprc5b | 32.7 | 258.5 | 7.9 | 14.6 | 71.5 | 4.9 |
| LOC683077 | 102.9 | 791.3 | 7.7 | 116.6 | 347.7 | 3.0 |
| Jag1 | 0.4 | 2.9 | 7.7 | 1.0 | 2.6 | 2.8 |
| Etnk2 | 0.9 | 6.8 | 7.7 | 2.2 | 3.8 | 1.7 |
| Smim3 | 1.1 | 8.3 | 7.6 | 3.6 | 23.2 | 6.4 |
| Cdo1 | 1.5 | 11.6 | 7.6 | 1.3 | 1.1 | 0.9 |
| Neurod2 | 31.0 | 233.7 | 7.5 | 51.9 | 95.7 | 1.8 |
| Gast | 8.1 | 60.8 | 7.5 | 4.8 | 17.6 | 3.6 |
| Hmgcs2 | 0.3 | 2.1 | 7.5 | 0.2 | 0.6 | 2.7 |
| RGD1562865 | 0.9 | 6.4 | 7.4 | 0.4 | 1.8 | 4.5 |
| Slc16a1 | 0.9 | 6.5 | 7.4 | 12.0 | 16.5 | 1.4 |
| Ctgf | 0.1 | 0.5 | 7.4 | 0.0 | 1.3 | |
| Gls2 | 2.2 | 16.1 | 7.4 | 1.4 | 1.9 | 1.4 |
| Gdf15 | 19.6 | 144.0 | 7.4 | 10.6 | 27.8 | 2.6 |
| Sgms2 | 5.9 | 42.9 | 7.3 | 10.2 | 26.9 | 2.7 |
| Jund | 79.1 | 575.1 | 7.3 | 69.3 | 302.9 | 4.4 |
| G0s2 | 19.2 | 139.2 | 7.3 | 150.3 | 147.9 | 1.0 |
| Dos | 42.4 | 306.7 | 7.2 | 26.0 | 110.7 | 4.3 |
| Tnfaip8 | 1.0 | 7.4 | 7.2 | 1.2 | 7.3 | 5.9 |
| Cebpb | 9.3 | 67.0 | 7.2 | 4.8 | 32.5 | 6.8 |
| Net1 | 38.0 | 273.3 | 7.2 | 25.3 | 31.9 | 1.3 |
| Hs3st3b1 | 0.6 | 4.4 | 7.2 | 0.3 | 2.2 | 6.7 |
| Plat | 0.5 | 3.5 | 7.0 | 1.0 | 11.7 | 12.1 |
| Rem2 | 24.4 | 170.3 | 7.0 | 22.7 | 80.9 | 3.6 |
| Errfi1 | 17.1 | 118.7 | 7.0 | 13.8 | 68.2 | 4.9 |
| Nfkbiz | 0.9 | 6.6 | 6.9 | 2.1 | 6.6 | 3.1 |
| Gareml | 0.2 | 1.6 | 6.9 | 0.6 | 2.3 | 3.8 |
| Phospho1 | 2.0 | 14.0 | 6.9 | 5.7 | 10.6 | 1.8 |
| Zfp612 | 6.8 | 46.9 | 6.9 | 4.4 | 9.6 | 2.2 |
| Tes | 17.5 | 119.7 | 6.8 | 29.9 | 84.5 | 2.8 |
| Paqr3 | 5.7 | 38.7 | 6.8 | 3.6 | 10.6 | 3.0 |
| Msantd1 | 1.2 | 8.4 | 6.8 | 0.7 | 3.7 | 5.7 |
| Tlr2 | 0.0 | 0.2 | 6.7 | 0.1 | 0.2 | 1.2 |
| Scn1b | 1.9 | 13.0 | 6.7 | 2.4 | 4.9 | 2.0 |
| Abcg2 | 0.0 | 0.2 | 6.7 | 0.1 | 0.1 | 2.2 |
| Omg | 0.0 | 0.3 | 6.7 | 0.1 | 0.1 | 0.5 |
| Calhm2 | 0.0 | 0.3 | 6.7 | 1.3 | 0.2 | 0.2 |
| Tubb2b | 0.0 | 0.3 | 6.7 | 0.2 | 0.1 | 0.5 |
| Fgg | 0.1 | 0.4 | 6.7 | 0.0 | 0.1 | |
| Chrna7 | 0.3 | 2.2 | 6.7 | 1.8 | 8.7 | 4.8 |
| Cpa6 | 0.1 | 0.4 | 6.7 | 0.0 | 0.0 | |
| Gda | 0.1 | 0.4 | 6.7 | 0.0 | 0.3 | |
| Micb | 0.1 | 1.0 | 6.7 | 0.4 | 0.9 | 2.3 |
| Nudt17 | 0.1 | 0.5 | 6.7 | 0.6 | 0.3 | 0.4 |
| RT1-M5 | 0.1 | 0.6 | 6.7 | 0.3 | 0.2 | 0.6 |
| Alb | 0.9 | 5.8 | 6.7 | 1.3 | 2.1 | 1.7 |
| Rln1 | 0.2 | 1.6 | 6.7 | 0.2 | 0.4 | 2.2 |
| Pak1 | 8.7 | 58.2 | 6.7 | 7.0 | 13.6 | 1.9 |
| Flrt3 | 0.3 | 1.8 | 6.6 | 1.2 | 1.5 | 1.2 |
| Egfr | 2.9 | 19.0 | 6.6 | 0.6 | 2.9 | 4.6 |
| Cycs | 0.9 | 6.1 | 6.6 | 2.3 | 2.5 | 1.1 |
| Iqsec3 | 6.1 | 39.8 | 6.6 | 3.9 | 12.7 | 3.2 |
| Ldhb | 33.5 | 218.5 | 6.5 | 60.3 | 271.3 | 4.5 |
| Rcan2 | 17.2 | 111.8 | 6.5 | 13.1 | 30.2 | 2.3 |
| Tuba4a | 168.7 | 1087.4 | 6.4 | 227.2 | 554.8 | 2.4 |
| Zfand2a | 72.1 | 463.6 | 6.4 | 83.1 | 337.2 | 4.1 |
| Zc3hav1 | 34.6 | 219.3 | 6.3 | 34.2 | 118.9 | 3.5 |
| Ctu2 | 6.6 | 41.3 | 6.3 | 12.3 | 14.2 | 1.1 |
| Homer1 | 2.2 | 13.9 | 6.3 | 2.4 | 4.4 | 1.9 |
| LOC100364769 | 0.2 | 1.2 | 6.3 | 0.8 | 0.9 | 1.0 |
| Gnat1 | 1.6 | 10.2 | 6.2 | 0.6 | 1.1 | 1.8 |
| Zrsr1 | 4.6 | 28.5 | 6.2 | 3.5 | 9.8 | 2.8 |
| Pmp22 | 4.6 | 28.3 | 6.2 | 4.5 | 11.4 | 2.6 |
| Map9 | 24.8 | 153.5 | 6.2 | 23.8 | 57.7 | 2.4 |
| Ahnak | 0.1 | 0.8 | 6.1 | 0.1 | 1.1 | 12.4 |
| Agap3 | 43.9 | 266.5 | 6.1 | 49.7 | 90.8 | 1.8 |
| Chst15 | 0.2 | 1.2 | 6.1 | 0.1 | 0.3 | 4.4 |
| Nr2f2 | 16.0 | 96.7 | 6.1 | 17.8 | 115.3 | 6.5 |
| Clstn3 | 38.4 | 232.6 | 6.1 | 17.8 | 40.1 | 2.3 |
| Cntn2 | 0.3 | 1.5 | 6.0 | 0.2 | 0.3 | 1.6 |
| Fbxo34 | 9.1 | 54.9 | 6.0 | 13.2 | 42.2 | 3.2 |
| Osbpl6 | 5.2 | 30.9 | 6.0 | 5.5 | 26.6 | 4.9 |
| Dusp4 | 18.5 | 110.7 | 6.0 | 16.1 | 105.3 | 6.5 |
| Arl4a | 2.1 | 12.2 | 5.9 | 4.7 | 9.7 | 2.1 |
| Apoe | 3.0 | 17.5 | 5.9 | 3.3 | 6.8 | 2.0 |
| Ube2z | 83.9 | 493.3 | 5.9 | 86.1 | 241.9 | 2.8 |
| Tp53rk | 1.4 | 8.2 | 5.9 | 1.7 | 3.0 | 1.8 |
| Prickle2 | 2.9 | 17.2 | 5.9 | 2.7 | 2.6 | 0.9 |
| Jun | 3.2 | 18.7 | 5.9 | 6.2 | 8.1 | 1.3 |
| Sfmbt2 | 0.1 | 0.5 | 5.8 | 0.7 | 0.6 | 0.9 |
| Tob1 | 30.6 | 177.8 | 5.8 | 24.9 | 85.1 | 3.4 |
| Oxtr | 1.3 | 7.7 | 5.8 | 3.1 | 14.9 | 4.8 |
| Cd274 | 11.3 | 65.3 | 5.8 | 9.7 | 48.6 | 5.0 |
| Pim3 | 50.1 | 289.4 | 5.8 | 52.8 | 134.7 | 2.5 |
| Kcnf1 | 3.0 | 17.3 | 5.8 | 1.0 | 4.1 | 4.1 |
| Ephx4 | 0.5 | 2.9 | 5.8 | 1.0 | 1.7 | 1.7 |
| Slc7a5 | 93.4 | 535.6 | 5.7 | 106.3 | 444.7 | 4.2 |
| Cln8 | 9.1 | 51.7 | 5.7 | 9.3 | 31.5 | 3.4 |
| Adra2b | 0.1 | 0.5 | 5.7 | 0.2 | 0.4 | 2.4 |
| Tmem158 | 4.2 | 23.9 | 5.7 | 2.6 | 10.8 | 4.1 |
| Cabp1 | 62.0 | 350.8 | 5.7 | 23.6 | 48.5 | 2.1 |
| Zbtb10 | 7.3 | 41.0 | 5.6 | 11.0 | 13.7 | 1.2 |
| Hr | 1.5 | 8.2 | 5.6 | 1.4 | 1.7 | 1.0 |
| Sat1 | 4.1 | 23.3 | 5.6 | 4.9 | 10.5 | 2.1 |
| Ninj1 | 106.6 | 596.4 | 5.6 | 162.0 | 407.8 | 2.5 |
| Ftl | 9.3 | 52.2 | 5.6 | 16.1 | 36.1 | 2.3 |
| Pqlc1 | 20.6 | 115.1 | 5.6 | 34.2 | 82.9 | 2.4 |
| Id1 | 155.0 | 863.5 | 5.6 | 196.4 | 576.5 | 2.9 |
| Fam204a | 5.7 | 31.7 | 5.6 | 10.0 | 16.8 | 1.7 |
| Cpeb4 | 46.7 | 256.9 | 5.5 | 32.9 | 137.6 | 4.2 |
| Etnk1 | 41.4 | 226.7 | 5.5 | 45.7 | 205.8 | 4.5 |
| Zc3h12a | 1.8 | 10.0 | 5.5 | 1.4 | 5.7 | 4.1 |
| Ntrk2 | 12.2 | 66.7 | 5.5 | 6.7 | 20.2 | 3.0 |
| Cps1 | 0.0 | 0.2 | 5.4 | 0.1 | 0.0 | 0.7 |
| Clca5 | 0.1 | 0.6 | 5.4 | 0.3 | 1.0 | 3.2 |
| Lgr5 | 0.1 | 0.4 | 5.4 | 0.3 | 0.2 | 0.4 |
| Trib3 | 7.7 | 41.8 | 5.4 | 4.1 | 17.1 | 4.2 |
| RGD1309139 | 0.0 | 0.2 | 5.4 | 0.0 | 0.0 | 1.5 |
| Hpn | 0.0 | 0.3 | 5.4 | 0.0 | 0.1 | |
| Cyp2d2 | 0.0 | 0.3 | 5.4 | 0.1 | 0.1 | 1.5 |
| E230034O05Rik | 0.1 | 0.3 | 5.4 | 0.1 | 0.2 | 1.5 |
| Prr15 | 0.1 | 0.3 | 5.4 | 0.4 | 0.5 | 1.2 |
| Mettl7b | 0.1 | 0.4 | 5.4 | 0.0 | 0.0 | |
| Asgr1 | 0.1 | 0.4 | 5.4 | 0.2 | 0.1 | 0.5 |
| Sgcz | 0.1 | 0.4 | 5.4 | 0.1 | 0.3 | 2.2 |
| Col4a4 | 0.1 | 0.4 | 5.4 | 0.6 | 0.4 | 0.6 |
| Adcy5 | 1.4 | 7.8 | 5.4 | 0.8 | 1.0 | 1.2 |
| Tmem229a | 1.7 | 8.8 | 5.3 | 1.1 | 2.2 | 1.9 |
| Sdc1 | 21.7 | 114.3 | 5.3 | 44.2 | 76.5 | 1.7 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Zfp395 | 19.4 | 102.1 | 5.3 | 30.0 | 81.7 | 2.7 |
| Tmem66 | 119.2 | 627.8 | 5.3 | 63.6 | 165.1 | 2.6 |
| Slc6a15 | 1.1 | 5.9 | 5.2 | 4.1 | 5.5 | 1.4 |
| Pcdh9 | 0.7 | 3.4 | 5.2 | 0.5 | 4.4 | 9.4 |
| Grm2 | 23.9 | 125.4 | 5.2 | 10.4 | 21.7 | 2.1 |
| Pcdh7 | 0.1 | 0.7 | 5.2 | 0.2 | 1.2 | 5.9 |
| Synm | 1.3 | 7.0 | 5.2 | 0.5 | 4.2 | 8.6 |
| Eif2c2 | 69.3 | 354.5 | 5.1 | 90.6 | 242.4 | 2.7 |
| Cyp2e1 | 0.3 | 1.3 | 5.1 | 0.2 | 0.3 | 1.2 |
| Gpt2 | 8.6 | 43.9 | 5.1 | 4.9 | 12.8 | 2.6 |
| Igfbp4 | 29.1 | 147.1 | 5.1 | 35.3 | 77.8 | 2.2 |
| Affl | 5.8 | 29.2 | 5.0 | 6.3 | 12.5 | 2.0 |
| Rsad2 | 0.2 | 1.2 | 5.0 | 0.1 | 1.0 | 19.2 |
| Slc7a8 | 23.5 | 118.2 | 5.0 | 20.6 | 82.9 | 4.0 |
| Arl5b | 2.3 | 11.7 | 5.0 | 3.5 | 16.6 | 4.7 |
| Stard4 | 7.3 | 36.5 | 5.0 | 14.8 | 74.2 | 5.0 |
| Cdkn1b | 42.4 | 213.0 | 5.0 | 55.7 | 227.3 | 4.1 |
| MGC114464 | 22.3 | 111.4 | 5.0 | 15.0 | 33.9 | 2.3 |
| Prosapip1 | 9.4 | 46.5 | 5.0 | 7.6 | 12.1 | 1.6 |
| Itpk1 | 47.1 | 232.3 | 4.9 | 57.4 | 98.4 | 1.7 |
| Sgk1 | 9.5 | 46.7 | 4.9 | 3.1 | 11.4 | 3.6 |
| Siah2 | 10.8 | 52.9 | 4.9 | 9.8 | 30.1 | 3.1 |
| Slc6a17 | 66.9 | 326.1 | 4.9 | 42.4 | 66.5 | 1.6 |
| Arl4d | 17.1 | 83.4 | 4.9 | 55.7 | 82.5 | 1.5 |
| Slc2a1 | 22.2 | 107.6 | 4.9 | 22.3 | 34.6 | 1.5 |
| Slc38a3 | 19.9 | 96.2 | 4.8 | 55.2 | 78.1 | 1.4 |
| Camk2d | 6.1 | 29.3 | 4.8 | 6.4 | 16.1 | 2.5 |
| Tpm4 | 248.9 | 1198.0 | 4.8 | 419.2 | 755.1 | 1.8 |
| Ifrd1 | 14.3 | 68.7 | 4.8 | 22.9 | 70.1 | 3.1 |
| Pwwp2b | 9.2 | 43.9 | 4.8 | 5.3 | 11.3 | 2.1 |
| Cldn11 | 0.4 | 1.9 | 4.8 | 0.1 | 0.4 | 3.4 |
| Zmynd15 | 1.5 | 7.3 | 4.8 | 7.8 | 10.3 | 1.3 |
| Gla | 24.3 | 115.4 | 4.8 | 27.4 | 48.8 | 1.8 |
| Ddi2 | 12.6 | 59.9 | 4.7 | 12.6 | 25.9 | 2.1 |
| Tnfrsf9 | 1.0 | 4.9 | 4.7 | 3.0 | 6.1 | 2.1 |
| Pfkfb3 | 3.1 | 14.8 | 4.7 | 22.1 | 25.5 | 1.2 |
| Usp42 | 18.8 | 89.2 | 4.7 | 17.1 | 52.4 | 3.1 |
| Luzp1 | 5.7 | 26.8 | 4.7 | 5.1 | 17.3 | 3.4 |
| Il6r | 15.0 | 70.9 | 4.7 | 21.5 | 19.1 | 0.9 |
| Krt80 | 0.5 | 2.3 | 4.7 | 0.1 | 0.0 | 0.0 |
| Rcn1 | 47.6 | 223.8 | 4.7 | 58.5 | 146.1 | 2.5 |
| Prox1 | 9.5 | 44.6 | 4.7 | 6.9 | 22.6 | 3.3 |
| Gpx1 | 0.8 | 3.9 | 4.7 | 0.6 | 0.8 | 1.3 |
| Lmna | 93.8 | 438.3 | 4.7 | 139.2 | 371.2 | 2.7 |
| Pdlim1 | 102.3 | 478.1 | 4.7 | 66.4 | 207.6 | 3.1 |
| Mgst2 | 0.3 | 1.3 | 4.7 | 1.4 | 0.7 | 0.5 |
| Zfp385b | 0.2 | 0.9 | 4.6 | 0.3 | 0.3 | 0.9 |
| Fam46a | 29.0 | 133.0 | 4.6 | 87.4 | 190.8 | 2.2 |
| Fga | 0.1 | 0.4 | 4.6 | 0.1 | 0.0 | 0.0 |
| Zfp707 | 0.4 | 2.0 | 4.6 | 1.2 | 1.6 | 1.3 |
| Kif26a | 14.7 | 67.3 | 4.6 | 17.3 | 35.8 | 2.1 |
| Cdc14a | 11.2 | 51.2 | 4.6 | 5.4 | 22.3 | 4.1 |
| Cdk11b | 8.0 | 36.8 | 4.6 | 12.7 | 13.9 | 1.1 |
| Cidec | 7.3 | 33.5 | 4.6 | 6.1 | 16.4 | 2.7 |
| Grin1 | 10.8 | 48.9 | 4.5 | 5.1 | 9.8 | 1.9 |
| Tmem163 | 25.5 | 115.5 | 4.5 | 16.9 | 71.4 | 4.2 |
| Map3k6 | 0.1 | 0.5 | 4.5 | 0.3 | 0.7 | 2.1 |
| Atp1a2 | 1.3 | 5.9 | 4.5 | 0.8 | 0.9 | 1.1 |
| Dab2 | 0.1 | 0.3 | 4.5 | 0.1 | 0.9 | 14.3 |
| RGD1305298 | 0.3 | 1.2 | 4.5 | 0.5 | 0.4 | 0.8 |
| Dusp8 | 69.5 | 308.6 | 4.4 | 76.2 | 145.7 | 1.9 |
| Cabyr | 0.3 | 1.2 | 4.4 | 0.7 | 0.7 | 1.1 |
| Tmem51 | 4.0 | 17.7 | 4.4 | 10.8 | 11.2 | 1.0 |
| Foxa2 | 51.8 | 228.3 | 4.4 | 86.3 | 159.3 | 1.8 |
| Yod1 | 6.8 | 30.0 | 4.4 | 6.9 | 22.5 | 3.2 |
| Ier3 | 14.2 | 62.0 | 4.4 | 7.7 | 36.7 | 4.8 |
| Ascl1 | 4.9 | 21.5 | 4.4 | 4.2 | 42.7 | 10.1 |
| Gadd45g | 306.6 | 1338.0 | 4.4 | 221.6 | 327.9 | 1.5 |
| Kcna2 | 1.5 | 6.4 | 4.4 | 8.7 | 7.1 | 0.8 |
| Vgf | 389.1 | 1693.3 | 4.4 | 421.2 | 1457.5 | 3.5 |
| Ddit3 | 44.4 | 192.9 | 4.3 | 32.5 | 46.5 | 1.4 |
| Ndel1 | 29.7 | 128.6 | 4.3 | 23.9 | 50.6 | 2.1 |
| Snx13 | 4.7 | 20.2 | 4.3 | 3.8 | 5.4 | 1.4 |
| P2rx2 | 1.0 | 4.1 | 4.3 | 0.6 | 2.4 | 3.8 |
| â€œeMafA" | 149.5 | 639.4 | 4.3 | 14.6 | 77.3 | 5.3 |
| Cntfr | 98.0 | 418.1 | 4.3 | 246.1 | 424.5 | 1.7 |
| Clcn5 | 15.3 | 65.2 | 4.3 | 10.6 | 28.0 | 2.6 |
| Ier2 | 5.0 | 21.2 | 4.3 | 5.1 | 23.6 | 4.6 |
| Gad1 | 7.5 | 31.7 | 4.2 | 13.7 | 15.3 | 1.1 |
| B3gnt2 | 9.1 | 38.7 | 4.2 | 4.6 | 12.9 | 2.8 |
| Neurod4 | 0.5 | 2.2 | 4.2 | 1.2 | 3.1 | 2.6 |
| Fam70b | 1.1 | 4.8 | 4.2 | 0.0 | 0.0 | |
| Cxcl16 | 10.2 | 42.9 | 4.2 | 58.0 | 77.6 | 1.3 |
| Hoxb13 | 9.8 | 41.1 | 4.2 | 8.8 | 25.6 | 2.9 |
| Rps15a | 11.8 | 49.3 | 4.2 | 28.0 | 51.9 | 1.9 |
| Ifngr1 | 23.3 | 97.5 | 4.2 | 28.6 | 74.7 | 2.6 |
| Ptpn4 | 5.0 | 20.9 | 4.2 | 4.9 | 12.3 | 2.5 |
| Phf15 | 54.9 | 228.1 | 4.2 | 49.4 | 76.8 | 1.6 |
| Mafk | 21.7 | 89.8 | 4.1 | 29.4 | 72.2 | 2.5 |
| Kti12 | 8.5 | 35.4 | 4.1 | 12.8 | 24.3 | 1.9 |
| Tesk2 | 2.2 | 9.2 | 4.1 | 1.7 | 3.8 | 2.2 |
| Zc3h12c | 8.4 | 34.6 | 4.1 | 8.5 | 26.4 | 3.1 |
| Scrt2 | 1.1 | 4.5 | 4.1 | 2.4 | 7.4 | 3.1 |
| Rhpn2 | 9.7 | 39.8 | 4.1 | 13.0 | 35.1 | 2.7 |
| Sos1 | 12.8 | 52.8 | 4.1 | 16.4 | 23.5 | 1.4 |
| Fam110a | 30.6 | 125.9 | 4.1 | 54.4 | 73.5 | 1.4 |
| Rasgrp2 | 0.8 | 3.2 | 4.1 | 8.3 | 5.3 | 0.6 |
| Usp6nl | 9.2 | 37.9 | 4.1 | 6.8 | 25.8 | 3.8 |
| Mertk | 35.9 | 146.8 | 4.1 | 2.2 | 8.8 | 4.0 |
| Fam222a | 53.4 | 217.8 | 4.1 | 39.2 | 104.7 | 2.7 |
| Ankrd61 | 1.6 | 6.5 | 4.1 | 1.1 | 2.4 | 2.2 |
| Gchfr | 4.8 | 19.6 | 4.1 | 3.5 | 4.2 | 1.2 |
| Bcl2l11 | 13.1 | 53.2 | 4.1 | 28.8 | 78.4 | 2.7 |
| Ndufa5 | 28.7 | 116.5 | 4.1 | 26.3 | 34.3 | 1.3 |
| Col4a1 | 0.0 | 0.0 | 4.1 | 0.0 | 0.1 | 10.3 |
| Ltbp1 | 0.0 | 0.1 | 4.1 | 0.1 | 0.2 | 1.4 |
| Frmpd4 | 0.0 | 0.1 | 4.1 | 0.0 | 0.1 | 1.5 |
| Ephb3 | 0.7 | 2.9 | 4.1 | 0.9 | 2.7 | 2.9 |
| Fam65b | 0.0 | 0.1 | 4.1 | 0.0 | 0.0 | |
| Csf1r | 0.0 | 0.1 | 4.1 | 0.1 | 0.0 | 0.3 |
| Clca1 | 0.0 | 0.2 | 4.1 | 0.0 | 0.0 | |
| Lrrc4 | 0.3 | 1.4 | 4.1 | 0.4 | 0.5 | 1.5 |
| Plag1 | 0.0 | 0.1 | 4.1 | 0.1 | 0.1 | 0.7 |
| Slco5a1 | 0.1 | 0.6 | 4.1 | 0.9 | 0.5 | 0.6 |
| Espnl | 0.0 | 0.1 | 4.1 | 0.0 | 0.1 | 1.5 |
| Mmp2 | 0.0 | 0.1 | 4.1 | 0.0 | 0.0 | 1.5 |
| Adra1d | 0.0 | 0.1 | 4.1 | 0.0 | 0.0 | 0.0 |
| Atcay | 0.1 | 0.2 | 4.0 | 0.1 | 0.1 | 1.1 |
| Papolb | 0.1 | 0.3 | 4.0 | 0.1 | 0.5 | 3.5 |
| Serpina3n | 0.1 | 0.3 | 4.0 | 0.1 | 0.3 | 2.2 |
| Sfrp5 | 0.0 | 0.2 | 4.0 | 0.2 | 0.4 | 2.0 |
| Plin5 | 0.1 | 0.3 | 4.0 | 0.0 | 0.0 | 0.0 |
| Dnajb9 | 10.3 | 41.7 | 4.0 | 3.9 | 6.6 | 1.7 |
| Prrg4 | 0.1 | 0.5 | 4.0 | 0.6 | 1.8 | 3.2 |
| Hspb8 | 0.0 | 0.2 | 4.0 | 0.0 | 0.0 | |
| Arntl2 | 0.1 | 0.4 | 4.0 | 0.0 | 0.0 | 0.0 |
| Tdo2 | 0.1 | 0.4 | 4.0 | 0.2 | 0.2 | 1.0 |
| LOC100910940 | 0.2 | 0.6 | 4.0 | 0.2 | 0.2 | 0.7 |
| Pgf | 0.1 | 0.2 | 4.0 | 0.4 | 0.2 | 0.5 |
| Proc | 0.1 | 0.2 | 4.0 | 0.1 | 0.1 | 0.7 |
| Tmem591 | 0.1 | 0.2 | 4.0 | 0.0 | 0.3 | 5.9 |
| Art3 | 0.1 | 0.5 | 4.0 | 0.1 | 0.2 | 1.5 |
| Ptger4 | 0.1 | 0.5 | 4.0 | 0.2 | 0.5 | 2.6 |
| Trim50 | 0.2 | 0.7 | 4.0 | 1.0 | 0.3 | 0.3 |
| Ush1g | 0.1 | 0.2 | 4.0 | 0.0 | 0.0 | |
| Slc7a1 | 42.9 | 173.0 | 4.0 | 34.2 | 72.0 | 2.1 |
| C1qtnf4 | 0.1 | 0.3 | 4.0 | 0.1 | 0.0 | 0.0 |
| Dnajb7 | 0.1 | 0.3 | 4.0 | 0.1 | 0.2 | 3.0 |
| Gpsm3 | 0.1 | 0.3 | 4.0 | 0.2 | 0.2 | 1.0 |
| Eaf2 | 0.2 | 0.6 | 4.0 | 0.4 | 1.1 | 2.5 |
| Upk3a | 0.1 | 0.3 | 4.0 | 5.5 | 5.5 | 1.0 |
| Olr418 | 0.1 | 0.4 | 4.0 | 0.3 | 0.0 | 0.0 |
| Lmbr1 | 9.9 | 39.3 | 4.0 | 10.2 | 15.6 | 1.5 |
| Cdkn1a | 8.3 | 33.0 | 4.0 | 35.4 | 104.4 | 3.0 |
| Bach1 | 3.1 | 12.3 | 4.0 | 6.3 | 10.8 | 1.7 |
| Cyp51 | 13.1 | 51.9 | 4.0 | 22.3 | 46.8 | 2.1 |
| Rnf185 | 14.6 | 57.8 | 4.0 | 23.8 | 38.3 | 1.6 |
| Fabp1 | 1.2 | 4.9 | 3.9 | 0.8 | 0.3 | 0.4 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Usp10 | 14.6 | 57.3 | 3.9 | 17.0 | 23.0 | 1.4 |
| Fdx1 | 6.0 | 23.4 | 3.9 | 5.9 | 14.5 | 2.4 |
| RGD1311188 | 2.5 | 9.9 | 3.9 | 2.4 | 4.8 | 2.0 |
| Ubash3b | 1.9 | 7.4 | 3.9 | 2.7 | 3.7 | 1.4 |
| Sorcs1 | 0.2 | 0.7 | 3.9 | 0.1 | 0.1 | 0.7 |
| Vstm5 | 0.8 | 3.2 | 3.9 | 0.8 | 3.3 | 4.0 |
| Pde4d | 14.2 | 55.4 | 3.9 | 12.3 | 45.7 | 3.7 |
| Slc9b2 | 1.4 | 5.6 | 3.9 | 10.8 | 12.1 | 1.1 |
| Tgds | 9.4 | 36.5 | 3.9 | 6.8 | 11.7 | 1.7 |
| Trpc4 | 4.3 | 16.9 | 3.9 | 11.6 | 41.9 | 3.6 |
| Rell2 | 6.5 | 25.2 | 3.9 | 4.8 | 6.9 | 1.4 |
| Stk32a | 5.0 | 19.5 | 3.9 | 1.2 | 3.6 | 3.1 |
| Tsga10 | 1.0 | 4.0 | 3.9 | 0.4 | 1.3 | 3.0 |
| Sertad1 | 4.5 | 17.4 | 3.9 | 7.0 | 34.8 | 4.9 |
| Arid5a | 1.9 | 7.2 | 3.9 | 1.4 | 7.5 | 5.5 |
| Aen | 22.4 | 86.6 | 3.9 | 35.9 | 56.5 | 1.6 |
| Tubb6 | 1.0 | 3.9 | 3.9 | 2.0 | 14.0 | 7.1 |
| Shisa8 | 0.6 | 2.3 | 3.8 | 0.3 | 0.8 | 2.8 |
| Inpp5a | 13.2 | 50.8 | 3.8 | 15.8 | 26.6 | 1.7 |
| Klhl21 | 13.4 | 51.3 | 3.8 | 10.7 | 36.7 | 3.4 |
| Btg2 | 83.6 | 320.3 | 3.8 | 65.5 | 187.7 | 2.9 |
| Usp36 | 16.3 | 62.6 | 3.8 | 14.0 | 30.1 | 2.1 |
| Cbx8 | 18.0 | 69.0 | 3.8 | 15.9 | 29.8 | 1.9 |
| Baalc | 0.2 | 0.8 | 3.8 | 0.1 | 0.4 | 4.4 |
| Kpna1 | 14.4 | 54.9 | 3.8 | 20.3 | 35.2 | 1.7 |
| Map3k8 | 0.5 | 1.8 | 3.8 | 0.4 | 0.9 | 2.3 |
| Crb3 | 45.9 | 174.2 | 3.8 | 42.8 | 100.6 | 2.4 |
| Serp1 | 143.9 | 546.6 | 3.8 | 130.2 | 266.9 | 2.1 |
| LOC499781 | 1.6 | 6.0 | 3.8 | 1.6 | 6.5 | 4.0 |
| Trib2 | 1.6 | 6.1 | 3.8 | 1.7 | 7.9 | 4.8 |
| Agpat9 | 0.8 | 3.0 | 3.8 | 1.0 | 3.0 | 3.1 |
| Slc38a5 | 0.7 | 2.6 | 3.8 | 0.1 | 0.1 | 1.0 |
| Ddx3x | 40.4 | 152.0 | 3.8 | 93.2 | 132.0 | 1.4 |
| Rtp1 | 3.0 | 11.1 | 3.7 | 4.0 | 6.5 | 1.6 |
| Tmub1 | 28.2 | 105.4 | 3.7 | 24.5 | 36.3 | 1.5 |
| Cul4b | 30.5 | 114.1 | 3.7 | 39.0 | 83.5 | 2.1 |
| Fdxr | 3.2 | 12.0 | 3.7 | 5.4 | 5.7 | 1.0 |
| Atg16l2 | 7.1 | 26.5 | 3.7 | 5.1 | 8.0 | 1.6 |
| Samd8 | 13.6 | 50.8 | 3.7 | 16.0 | 36.2 | 2.3 |
| Pde10a | 33.5 | 125.2 | 3.7 | 46.2 | 91.8 | 2.0 |
| Ism1 | 3.1 | 11.6 | 3.7 | 5.2 | 30.6 | 5.9 |
| Ctnnb1 | 120.6 | 447.6 | 3.7 | 142.2 | 303.6 | 2.1 |
| Aspg | 0.1 | 0.5 | 3.7 | 0.1 | 0.0 | 0.4 |
| Camk1g | 6.0 | 22.1 | 3.7 | 2.1 | 5.4 | 2.6 |
| Arih1 | 9.4 | 34.7 | 3.7 | 11.1 | 20.7 | 1.9 |
| Rpl21 | 1.0 | 3.8 | 3.7 | 2.8 | 3.4 | 1.2 |
| Dusp5 | 23.0 | 85.0 | 3.7 | 16.1 | 42.9 | 2.7 |
| Sult4a1 | 33.9 | 124.9 | 3.7 | 30.8 | 50.2 | 1.6 |
| Eml4 | 17.8 | 65.5 | 3.7 | 14.8 | 27.7 | 1.9 |
| Eif1a | 39.0 | 143.0 | 3.7 | 44.0 | 59.0 | 1.3 |
| Il18 | 0.6 | 2.1 | 3.7 | 1.1 | 1.5 | 1.3 |
| Ddhd1 | 10.0 | 36.4 | 3.7 | 7.9 | 11.8 | 1.5 |
| Fam84a | 0.2 | 0.7 | 3.6 | 0.3 | 0.2 | 0.9 |
| Ubr4 | 40.3 | 146.7 | 3.6 | 45.0 | 110.4 | 2.5 |
| Herpud1 | 93.9 | 342.0 | 3.6 | 45.9 | 66.0 | 1.4 |
| Ppat | 24.6 | 89.7 | 3.6 | 40.4 | 69.9 | 1.7 |
| Nid2 | 0.2 | 0.7 | 3.6 | 1.5 | 2.2 | 1.4 |
| Enc1 | 67.5 | 245.4 | 3.6 | 56.1 | 157.7 | 2.8 |
| Stk11 | 30.5 | 110.5 | 3.6 | 37.8 | 68.3 | 1.8 |
| Hivep2 | 22.0 | 79.8 | 3.6 | 23.0 | 51.4 | 2.2 |
| Tmem30a | 26.7 | 96.6 | 3.6 | 34.3 | 66.4 | 1.9 |
| Egr1 | 23.6 | 85.2 | 3.6 | 10.1 | 93.1 | 9.2 |
| Maged1 | 457.4 | 1649.7 | 3.6 | 430.4 | 796.1 | 1.8 |
| Tspan13 | 47.3 | 170.4 | 3.6 | 56.3 | 90.7 | 1.6 |
| Rinl | 0.1 | 0.3 | 3.6 | 0.1 | 0.0 | 0.0 |
| MGC125239 | 14.8 | 53.3 | 3.6 | 13.7 | 29.7 | 2.2 |
| Rmdn3 | 6.7 | 24.0 | 3.6 | 5.6 | 11.7 | 2.1 |
| Ccnd3 | 49.4 | 176.5 | 3.6 | 39.0 | 126.9 | 3.3 |
| Gsdmd | 1.5 | 5.2 | 3.6 | 1.0 | 2.0 | 2.0 |
| Rnf19b | 9.7 | 34.4 | 3.6 | 12.3 | 16.5 | 1.3 |
| Spock2 | 325.7 | 1158.5 | 3.6 | 108.0 | 226.8 | 2.1 |
| Pcdhgb7 | 0.4 | 1.3 | 3.6 | 1.5 | 1.0 | 0.7 |
| Rpl37a-ps1 | 101.9 | 361.6 | 3.5 | 319.2 | 342.9 | 1.1 |
| 41891 | 73.5 | 260.4 | 3.5 | 142.5 | 234.5 | 1.6 |
| Btaf1 | 15.0 | 53.1 | 3.5 | 17.5 | 56.3 | 3.2 |
| St18 | 140.7 | 496.5 | 3.5 | 73.2 | 200.7 | 2.7 |
| Vdac1 | 61.2 | 215.6 | 3.5 | 74.4 | 103.9 | 1.4 |
| Cltc | 165.7 | 579.1 | 3.5 | 168.6 | 275.3 | 1.6 |
| Gtf3c4 | 16.7 | 58.2 | 3.5 | 24.4 | 54.2 | 2.2 |
| Vegfa | 179.7 | 625.2 | 3.5 | 86.8 | 270.6 | 3.1 |
| Hpx | 0.7 | 2.3 | 3.5 | 0.4 | 0.5 | 1.2 |
| Slc9a3r1 | 127.7 | 443.5 | 3.5 | 310.8 | 692.2 | 2.2 |
| Snx30 | 13.0 | 45.2 | 3.5 | 9.5 | 15.3 | 1.6 |
| Arsj | 0.3 | 1.1 | 3.5 | 1.0 | 0.8 | 0.9 |
| Cflar | 7.6 | 26.1 | 3.5 | 7.0 | 15.5 | 2.2 |
| Tsc22d2 | 7.5 | 25.9 | 3.5 | 8.5 | 32.1 | 3.8 |
| Rasl11b | 2.1 | 7.3 | 3.5 | 3.2 | 10.8 | 3.4 |
| Surf4 | 9.5 | 32.5 | 3.4 | 8.8 | 20.6 | 2.3 |
| Trib1 | 50.2 | 172.0 | 3.4 | 55.4 | 107.4 | 1.9 |
| Tle3 | 23.9 | 81.7 | 3.4 | 12.5 | 17.1 | 1.4 |
| Frmd4a | 9.6 | 32.7 | 3.4 | 17.2 | 26.1 | 1.5 |
| Mir343 | 289.7 | 990.5 | 3.4 | 0.0 | 367.4 | |
| Fgfr1 | 17.9 | 61.2 | 3.4 | 12.7 | 40.1 | 3.2 |
| Ranbp2 | 23.3 | 79.2 | 3.4 | 22.3 | 30.8 | 1.4 |
| Slc3a2 | 136.8 | 465.5 | 3.4 | 164.5 | 335.0 | 2.0 |
| Tpst2 | 54.0 | 183.3 | 3.4 | 43.0 | 72.3 | 1.7 |
| Wnt4 | 74.5 | 252.4 | 3.4 | 31.3 | 92.3 | 2.9 |
| RGD1305464 | 6.8 | 23.0 | 3.4 | 8.5 | 21.0 | 2.5 |
| Hspa5 | 1076.4 | 3641.3 | 3.4 | 462.9 | 792.3 | 1.7 |
| Trpm8 | 0.0 | 0.1 | 3.4 | 0.0 | 0.1 | 4.4 |
| Jam2 | 0.0 | 0.1 | 3.4 | 0.0 | 0.0 | 0.5 |
| Iqub | 0.1 | 0.3 | 3.4 | 0.1 | 0.0 | 0.3 |
| Egr2 | 0.1 | 0.2 | 3.4 | 0.0 | 0.5 | 23.6 |
| Trpv2 | 0.1 | 0.2 | 3.4 | 0.7 | 0.6 | 0.9 |
| Aldh1l1 | 0.1 | 0.2 | 3.4 | 0.0 | 0.1 | 4.4 |
| Ccdc163 | 3.7 | 12.3 | 3.4 | 7.0 | 9.8 | 1.4 |
| Tinagl1 | 0.1 | 0.3 | 3.4 | 0.3 | 0.2 | 0.6 |
| Spdya | 0.1 | 0.3 | 3.4 | 0.1 | 0.0 | 0.0 |
| Zfp295 | 12.1 | 40.7 | 3.4 | 12.1 | 18.7 | 1.5 |
| Grasp | 2.4 | 8.0 | 3.4 | 1.8 | 6.1 | 3.4 |
| Crkl | 8.3 | 28.1 | 3.4 | 13.5 | 28.6 | 2.1 |
| Rgs7bp | 0.6 | 2.1 | 3.4 | 0.9 | 1.3 | 1.5 |
| Prkar1a | 261.4 | 877.7 | 3.4 | 339.4 | 564.1 | 1.7 |
| Nap1l3 | 6.1 | 20.3 | 3.4 | 4.9 | 8.0 | 1.6 |
| Olr906 | 0.2 | 0.6 | 3.3 | 0.1 | 0.2 | 3.0 |
| Nt5c3 | 9.3 | 31.2 | 3.3 | 17.4 | 38.9 | 2.2 |
| Tspyl2 | 17.2 | 57.5 | 3.3 | 8.9 | 11.8 | 1.3 |
| Camk2n2 | 124.1 | 413.5 | 3.3 | 75.6 | 179.7 | 2.4 |
| Lrp12 | 9.0 | 29.8 | 3.3 | 9.8 | 21.7 | 2.2 |
| Gpr6 | 22.8 | 75.7 | 3.3 | 34.7 | 85.7 | 2.5 |
| Gba2 | 12.4 | 41.0 | 3.3 | 20.6 | 47.4 | 2.3 |
| Cnksr3 | 6.8 | 22.5 | 3.3 | 11.5 | 14.2 | 1.2 |
| Cldnd1 | 33.3 | 110.5 | 3.3 | 45.8 | 76.8 | 1.7 |
| Rasd2 | 0.2 | 0.8 | 3.3 | 0.7 | 1.5 | 2.1 |
| Aldoart1 | 0.6 | 2.1 | 3.3 | 1.1 | 1.9 | 1.8 |
| Agmat | 0.7 | 2.4 | 3.3 | 2.6 | 2.7 | 1.0 |
| Zfhx2 | 12.7 | 41.9 | 3.3 | 7.7 | 22.5 | 2.9 |
| Fam220a | 16.3 | 53.8 | 3.3 | 16.7 | 38.3 | 2.3 |
| Srsf2 | 223.7 | 736.6 | 3.3 | 273.5 | 706.0 | 2.6 |
| Vkorc1l1 | 1.9 | 6.2 | 3.3 | 4.6 | 5.7 | 1.3 |
| Surf6 | 3.5 | 11.5 | 3.3 | 8.7 | 9.8 | 1.1 |
| Nfkbie | 11.1 | 36.5 | 3.3 | 9.5 | 28.8 | 3.0 |
| Tnnc1 | 0.5 | 1.6 | 3.3 | 2.0 | 1.2 | 0.6 |
| Dhx38 | 19.2 | 62.9 | 3.3 | 33.9 | 35.4 | 1.0 |
| Kit | 93.5 | 306.0 | 3.3 | 108.5 | 236.4 | 2.2 |
| Sema4b | 61.7 | 202.1 | 3.3 | 52.0 | 123.8 | 2.4 |
| Tp53inp2 | 100.7 | 329.0 | 3.3 | 67.0 | 169.6 | 2.5 |
| Arg2 | 0.4 | 1.3 | 3.3 | 0.4 | 0.4 | 1.1 |
| Prmt1 | 0.5 | 1.6 | 3.3 | 2.3 | 3.0 | 1.3 |
| Fam160a1 | 2.4 | 7.7 | 3.3 | 1.4 | 2.9 | 2.0 |
| Cyr61 | 0.5 | 1.6 | 3.3 | 0.4 | 0.5 | 1.2 |
| Znrd1 | 98.2 | 319.2 | 3.3 | 101.0 | 192.4 | 1.9 |
| Selt | 56.7 | 183.9 | 3.2 | 93.6 | 141.7 | 1.5 |
| Ezr | 53.3 | 172.5 | 3.2 | 98.6 | 208.5 | 2.1 |
| Pde1c | 11.4 | 37.0 | 3.2 | 13.1 | 31.8 | 2.4 |
| Pou6f2 | 1.2 | 3.8 | 3.2 | 15.6 | 38.1 | 2.4 |
| Orc1 | 3.4 | 11.1 | 3.2 | 4.2 | 6.4 | 1.5 |
| Arf4 | 116.2 | 375.2 | 3.2 | 109.5 | 256.8 | 2.3 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Ets2 | 52.1 | 167.8 | 3.2 | 64.7 | 198.5 | 3.1 |
| Gtf2f1 | 76.0 | 244.7 | 3.2 | 128.6 | 140.9 | 1.1 |
| Nubp1 | 0.4 | 1.2 | 3.2 | 1.5 | 1.1 | 0.7 |
| Psmb6 | 5.1 | 16.5 | 3.2 | 18.2 | 19.7 | 1.1 |
| Tph1 | 0.3 | 1.0 | 3.2 | 0.4 | 0.5 | 1.4 |
| Rlbp1 | 0.3 | 0.8 | 3.2 | 0.9 | 0.9 | 1.0 |
| Rps15 | 414.8 | 1329.1 | 3.2 | 1220.8 | 1602.4 | 1.3 |
| Slc16a3 | 0.3 | 1.0 | 3.2 | 0.4 | 0.5 | 1.4 |
| Lims2 | 0.3 | 1.0 | 3.2 | 0.1 | 0.5 | 7.4 |
| Eaf1 | 17.7 | 56.6 | 3.2 | 25.0 | 56.6 | 2.3 |
| Nav2 | 42.5 | 135.5 | 3.2 | 21.1 | 43.9 | 2.1 |
| Nrn1 | 2.5 | 8.0 | 3.2 | 8.8 | 24.7 | 2.8 |
| Nap1l2 | 30.8 | 97.9 | 3.2 | 31.4 | 33.6 | 1.1 |
| Jak1 | 47.1 | 149.5 | 3.2 | 67.6 | 89.7 | 1.3 |
| Hck | 0.7 | 2.1 | 3.2 | 0.5 | 0.7 | 1.5 |
| Dffb | 13.8 | 43.8 | 3.2 | 12.1 | 52.8 | 4.4 |
| LOC100302372 | 0.1 | 0.2 | 3.2 | 0.1 | 0.3 | 2.0 |
| Rxra | 39.2 | 123.1 | 3.1 | 35.4 | 125.3 | 3.5 |
| Hivep1 | 13.2 | 41.5 | 3.1 | 9.7 | 41.3 | 4.2 |
| Evi2a | 0.2 | 0.6 | 3.1 | 0.0 | 0.4 | 7.4 |
| Baiap2 | 26.5 | 83.1 | 3.1 | 15.2 | 45.8 | 3.0 |
| Ablim2 | 16.8 | 52.6 | 3.1 | 5.9 | 13.2 | 2.3 |
| Gspt2 | 8.1 | 25.4 | 3.1 | 7.8 | 20.8 | 2.6 |
| Mad2l1bp | 19.5 | 61.0 | 3.1 | 42.1 | 93.7 | 2.2 |
| Hspbp1 | 62.0 | 193.5 | 3.1 | 109.2 | 170.2 | 1.6 |
| Ccdc80 | 0.2 | 0.7 | 3.1 | 0.5 | 0.8 | 1.4 |
| Vwce | 0.4 | 1.2 | 3.1 | 0.2 | 0.4 | 1.8 |
| Itpr3 | 40.5 | 126.2 | 3.1 | 38.0 | 67.4 | 1.8 |
| Ell | 9.1 | 28.3 | 3.1 | 7.4 | 15.8 | 2.1 |
| Efnb1 | 18.5 | 57.7 | 3.1 | 14.8 | 33.6 | 2.3 |
| Zbtb49 | 6.6 | 20.4 | 3.1 | 6.1 | 11.1 | 1.8 |
| Ppap2a | 42.4 | 131.8 | 3.1 | 25.2 | 36.1 | 1.4 |
| Med31 | 19.9 | 61.9 | 3.1 | 17.7 | 11.4 | 0.6 |
| Sgcd | 0.1 | 0.4 | 3.1 | 0.1 | 0.1 | 1.5 |
| Arhgap24 | 13.5 | 41.8 | 3.1 | 6.0 | 18.8 | 3.2 |
| RT1-CE2 | 2.1 | 6.4 | 3.1 | 4.7 | 7.1 | 1.5 |
| LOC100362347 | 4.1 | 12.7 | 3.1 | 4.5 | 6.8 | 1.5 |
| Iffo2 | 15.8 | 48.6 | 3.1 | 22.2 | 30.3 | 1.4 |
| LOC691995 | 4.8 | 14.7 | 3.1 | 10.0 | 18.8 | 1.9 |
| Traf4 | 65.2 | 200.6 | 3.1 | 98.7 | 156.7 | 1.6 |
| Hmox1 | 19.5 | 60.0 | 3.1 | 10.3 | 48.4 | 4.7 |
| Ccrn4l | 32.2 | 98.6 | 3.1 | 21.7 | 61.5 | 2.8 |
| Uba1 | 107.3 | 328.1 | 3.1 | 155.1 | 266.1 | 1.7 |
| Creb3l1 | 11.4 | 34.8 | 3.1 | 5.2 | 7.4 | 1.4 |
| Chpf | 54.1 | 165.1 | 3.1 | 46.3 | 110.1 | 2.4 |
| Eif6 | 82.0 | 250.3 | 3.1 | 130.8 | 192.0 | 1.5 |
| Chst8 | 1.5 | 4.5 | 3.1 | 8.6 | 7.8 | 0.9 |
| Creb3l2 | 41.4 | 125.9 | 3.0 | 33.1 | 132.4 | 4.0 |
| Taf1d | 15.9 | 48.3 | 3.0 | 28.1 | 43.8 | 1.6 |
| Myo16 | 5.5 | 16.7 | 3.0 | 1.7 | 3.2 | 1.9 |
| Fggy | 1.0 | 3.1 | 3.0 | 1.3 | 0.7 | 0.5 |
| Igf1r | 113.2 | 343.1 | 3.0 | 28.8 | 126.9 | 4.4 |
| Tln1 | 31.7 | 95.8 | 3.0 | 47.9 | 88.1 | 1.8 |
| Spats1 | 0.3 | 0.9 | 3.0 | 0.7 | 0.6 | 0.8 |
| Vps18 | 13.8 | 41.8 | 3.0 | 12.8 | 24.0 | 1.9 |
| Tbcc | 13.9 | 41.9 | 3.0 | 19.7 | 33.4 | 1.7 |
| Kcnk1 | 9.2 | 27.6 | 3.0 | 10.4 | 21.2 | 2.0 |
| Cables1 | 4.7 | 14.3 | 3.0 | 4.8 | 6.3 | 1.3 |
| Ppp2r1b | 13.6 | 40.9 | 3.0 | 17.6 | 29.1 | 1.7 |
| Abca5 | 4.2 | 12.8 | 3.0 | 3.0 | 6.2 | 2.1 |
| Tspyl4 | 41.5 | 124.9 | 3.0 | 38.9 | 66.6 | 1.7 |
| Erlin1 | 27.3 | 82.1 | 3.0 | 20.6 | 39.2 | 1.9 |
| Cpne8 | 2.4 | 7.2 | 3.0 | 6.0 | 12.3 | 2.0 |
| Top1 | 2.6 | 7.8 | 3.0 | 6.1 | 8.4 | 1.4 |
| Ccnl1 | 12.3 | 36.9 | 3.0 | 10.5 | 19.3 | 1.8 |
| Rhbdf2 | 5.1 | 15.3 | 3.0 | 7.1 | 12.1 | 1.7 |
| Pcgf5 | 15.8 | 47.1 | 3.0 | 14.4 | 27.8 | 1.9 |
| Id2 | 2.3 | 6.8 | 3.0 | 10.6 | 8.2 | 0.8 |
| Pabpc4 | 25.3 | 75.1 | 3.0 | 52.0 | 84.1 | 1.6 |
| Krt73 | 1.4 | 4.2 | 3.0 | 0.8 | 0.5 | 0.6 |
| Cdc42ep3 | 7.8 | 23.0 | 3.0 | 8.0 | 13.1 | 1.6 |
| Dlg3 | 5.4 | 16.1 | 3.0 | 3.3 | 3.5 | 1.1 |
| Ggct | 15.9 | 47.1 | 3.0 | 12.9 | 17.3 | 1.3 |
| Vegfc | 0.3 | 0.8 | 3.0 | 1.6 | 2.0 | 1.3 |
| Rras2 | 4.0 | 11.7 | 3.0 | 6.8 | 10.7 | 1.6 |
| Tor1b | 73.4 | 216.0 | 2.9 | 110.5 | 339.4 | 3.1 |
| Srsf7 | 65.8 | 193.2 | 2.9 | 101.4 | 138.9 | 1.4 |
| Ddx6 | 2.0 | 5.9 | 2.9 | 2.2 | 2.8 | 1.3 |
| Ica1 | 141.6 | 414.6 | 2.9 | 119.1 | 179.2 | 1.5 |
| Ddit4 | 11.6 | 34.0 | 2.9 | 10.4 | 19.9 | 1.9 |
| Ripk4 | 14.4 | 41.9 | 2.9 | 16.0 | 27.4 | 1.7 |
| Syt7 | 283.1 | 825.6 | 2.9 | 333.0 | 737.1 | 2.2 |
| Chac1 | 15.8 | 46.1 | 2.9 | 1.9 | 8.0 | 4.1 |
| Dnajc25 | 9.0 | 26.2 | 2.9 | 9.9 | 14.8 | 1.5 |
| Gpbp1 | 13.5 | 39.0 | 2.9 | 15.8 | 30.3 | 1.9 |
| Ckb | 536.5 | 1554.2 | 2.9 | 759.7 | 1426.6 | 1.9 |
| Ccny | 59.0 | 170.8 | 2.9 | 53.2 | 101.1 | 1.9 |
| Plg | 0.2 | 0.6 | 2.9 | 0.3 | 0.2 | 0.7 |
| Pcdha8 | 0.1 | 0.3 | 2.9 | 0.3 | 0.7 | 2.2 |
| Peli3 | 5.8 | 16.9 | 2.9 | 5.4 | 7.8 | 1.4 |
| Sts | 4.3 | 12.4 | 2.9 | 1.8 | 5.3 | 2.9 |
| Naf1 | 3.1 | 8.9 | 2.9 | 3.3 | 7.1 | 2.1 |
| Aldoa | 274.2 | 791.1 | 2.9 | 365.2 | 727.6 | 2.0 |
| Rasal1 | 5.2 | 15.1 | 2.9 | 4.0 | 9.1 | 2.3 |
| LOC684112 | 19.5 | 56.1 | 2.9 | 14.3 | 30.2 | 2.1 |
| Isca1 | 67.5 | 194.6 | 2.9 | 68.2 | 121.3 | 1.8 |
| Ass1 | 45.5 | 131.1 | 2.9 | 11.1 | 19.9 | 1.8 |
| Zfp516 | 50.5 | 145.3 | 2.9 | 25.1 | 70.2 | 2.8 |
| Usp2 | 0.6 | 1.7 | 2.9 | 0.3 | 1.0 | 3.4 |
| Wsb1 | 5.1 | 14.6 | 2.9 | 13.7 | 23.5 | 1.7 |
| RGD1310352 | 88.7 | 254.7 | 2.9 | 82.9 | 109.6 | 1.3 |
| Oraov1 | 17.6 | 50.4 | 2.9 | 24.0 | 55.9 | 2.3 |
| Phf20 | 16.7 | 47.8 | 2.9 | 19.4 | 22.8 | 1.2 |
| Eif4a2 | 92.6 | 265.0 | 2.9 | 112.5 | 145.4 | 1.3 |
| Bag3 | 30.8 | 88.2 | 2.9 | 43.4 | 78.2 | 1.8 |
| Ttpal | 19.1 | 54.6 | 2.9 | 13.4 | 47.0 | 3.5 |
| Asic2 | 2.0 | 5.8 | 2.9 | 1.5 | 5.2 | 3.4 |
| Hspa12b | 0.4 | 1.2 | 2.9 | 0.7 | 0.9 | 1.3 |
| Sh3pxd2a | 17.9 | 51.0 | 2.8 | 6.9 | 9.1 | 1.3 |
| Pcdhga12 | 0.5 | 1.3 | 2.8 | 0.6 | 1.5 | 2.5 |
| Slc20a1 | 30.5 | 86.5 | 2.8 | 39.0 | 60.3 | 1.5 |
| Nt5e | 6.4 | 18.0 | 2.8 | 2.9 | 3.7 | 1.3 |
| Apold1 | 0.8 | 2.3 | 2.8 | 1.4 | 3.1 | 2.2 |
| Rell1 | 13.9 | 39.2 | 2.8 | 14.1 | 26.5 | 1.9 |
| Appbp2 | 15.5 | 44.0 | 2.8 | 14.9 | 30.1 | 2.0 |
| Ppp1r15b | 34.0 | 96.0 | 2.8 | 26.0 | 58.0 | 2.2 |
| Tbccd1 | 16.3 | 46.2 | 2.8 | 9.3 | 9.7 | 1.0 |
| Pde8a | 7.8 | 22.0 | 2.8 | 5.5 | 11.1 | 2.0 |
| Trpc1 | 3.7 | 10.4 | 2.8 | 4.0 | 8.7 | 2.1 |
| Lamb3 | 21.1 | 59.6 | 2.8 | 32.7 | 55.1 | 1.7 |
| Bex1 | 236.0 | 665.0 | 2.8 | 601.7 | 642.9 | 1.1 |
| Ptprcap | 1.0 | 2.9 | 2.8 | 1.6 | 2.4 | 1.5 |
| Mecom | 1.1 | 3.2 | 2.8 | 5.3 | 16.4 | 3.1 |
| Unc13a | 32.5 | 91.4 | 2.8 | 27.1 | 49.9 | 1.8 |
| Tmem150b | 1.9 | 5.2 | 2.8 | 2.4 | 2.4 | 1.0 |
| Nfkbia | 28.9 | 80.9 | 2.8 | 30.6 | 79.9 | 2.6 |
| Slc25a37 | 4.1 | 11.5 | 2.8 | 3.0 | 8.3 | 2.8 |
| F13b | 0.5 | 1.4 | 2.8 | 1.4 | 2.2 | 1.6 |
| Tmem39a | 31.7 | 88.4 | 2.8 | 21.1 | 36.4 | 1.7 |
| RGD1311863 | 2.1 | 5.9 | 2.8 | 6.9 | 10.4 | 1.5 |
| Nudt4 | 60.0 | 165.9 | 2.8 | 93.7 | 125.1 | 1.3 |
| Hsp90aa1 | 14.5 | 40.1 | 2.8 | 44.8 | 50.9 | 1.1 |
| Rtn4rl1 | 68.8 | 190.0 | 2.8 | 47.6 | 95.4 | 2.0 |
| Smarca5 | 6.0 | 16.5 | 2.8 | 8.3 | 11.4 | 1.4 |
| Mxd3 | 46.5 | 128.2 | 2.8 | 111.8 | 144.3 | 1.3 |
| Bcor | 24.3 | 66.9 | 2.8 | 16.1 | 26.7 | 1.7 |
| Tnfrsf21 | 7.8 | 21.3 | 2.7 | 17.7 | 37.2 | 2.1 |
| Mcl1 | 16.5 | 45.3 | 2.7 | 20.2 | 41.1 | 2.0 |
| Stat3 | 52.9 | 144.6 | 2.7 | 45.9 | 100.4 | 2.2 |
| Tra2b | 17.5 | 47.6 | 2.7 | 30.5 | 42.7 | 1.4 |
| Atp2a2 | 283.6 | 773.2 | 2.7 | 244.9 | 490.9 | 2.0 |
| Ccdc86 | 231.9 | 631.7 | 2.7 | 263.2 | 364.8 | 1.4 |
| Ubqln2 | 165.8 | 451.0 | 2.7 | 164.5 | 292.8 | 1.8 |
| Nsbp1 | 2.4 | 6.5 | 2.7 | 12.7 | 7.9 | 0.6 |
| Snrnp48 | 19.3 | 52.3 | 2.7 | 26.2 | 42.0 | 1.6 |
| Slc38a2 | 67.3 | 182.7 | 2.7 | 101.6 | 166.6 | 1.6 |
| Alkbh5 | 44.6 | 121.0 | 2.7 | 40.0 | 75.7 | 1.9 |
| Efna5 | 12.1 | 32.7 | 2.7 | 4.5 | 12.1 | 2.7 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Nav3 | 0.0 | 0.1 | 2.7 | 0.0 | 0.1 | 1.8 |
| Scn4a | 0.0 | 0.0 | 2.7 | 0.0 | 0.0 | 0.0 |
| Frem3 | 0.0 | 0.0 | 2.7 | 0.1 | 0.1 | 1.1 |
| Slc9a3 | 0.0 | 0.1 | 2.7 | 0.0 | 0.1 | 2.2 |
| Heyl | 0.0 | 0.1 | 2.7 | 0.0 | 0.1 | 5.2 |
| Gucy2d | 0.0 | 0.1 | 2.7 | 0.0 | 0.0 | |
| Kbtbd8 | 1.5 | 4.2 | 2.7 | 2.4 | 5.0 | 2.1 |
| Cpxm2 | 0.0 | 0.1 | 2.7 | 0.0 | 0.0 | 0.0 |
| Dll4 | 0.1 | 0.2 | 2.7 | 0.2 | 0.2 | 1.5 |
| Hephl1 | 0.0 | 0.1 | 2.7 | 0.1 | 0.0 | 0.0 |
| Tmc3 | 0.0 | 0.1 | 2.7 | 0.0 | 0.0 | 1.5 |
| Nat8l | 0.0 | 0.1 | 2.7 | 0.0 | 0.0 | 0.0 |
| Itgb2 | 0.0 | 0.1 | 2.7 | 0.0 | 0.0 | 0.0 |
| Ppef2 | 0.0 | 0.1 | 2.7 | 0.1 | 0.0 | 0.0 |
| Itih4 | 0.1 | 0.2 | 2.7 | 0.1 | 0.0 | 0.0 |
| Ptplad1 | 22.4 | 60.4 | 2.7 | 19.0 | 30.2 | 1.6 |
| Mycbpap | 0.1 | 0.1 | 2.7 | 0.0 | 0.0 | |
| Hsf2bp | 0.3 | 0.8 | 2.7 | 0.1 | 0.3 | 3.3 |
| Ncf1 | 0.0 | 0.1 | 2.7 | 0.2 | 0.0 | 0.2 |
| B3galt1 | 0.1 | 0.3 | 2.7 | 0.2 | 0.1 | 0.4 |
| Pck1 | 0.0 | 0.1 | 2.7 | 0.2 | 0.0 | 0.2 |
| Ccdc67 | 0.0 | 0.1 | 2.7 | 0.0 | 0.0 | |
| Slc25a21 | 0.1 | 0.2 | 2.7 | 0.0 | 0.1 | 3.0 |
| P2rx5 | 0.1 | 0.2 | 2.7 | 0.0 | 0.0 | |
| Mxra8 | 0.0 | 0.1 | 2.7 | 0.0 | 0.1 | |
| Slc27a5 | 0.1 | 0.2 | 2.7 | 0.0 | 0.0 | 1.5 |
| Lingo2 | 0.0 | 0.1 | 2.7 | 0.0 | 0.1 | 4.4 |
| Rab21 | 20.5 | 55.2 | 2.7 | 24.2 | 36.9 | 1.5 |
| Hmox2-ps1 | 0.1 | 0.3 | 2.7 | 0.3 | 0.2 | 0.7 |
| Tra2a | 38.9 | 105.0 | 2.7 | 44.3 | 86.3 | 1.9 |
| Cpa5 | 0.0 | 0.1 | 2.7 | 0.1 | 0.4 | 3.9 |
| Slc7a7 | 0.0 | 0.1 | 2.7 | 0.1 | 0.1 | 1.5 |
| Adrb2 | 0.0 | 0.1 | 2.7 | 0.3 | 0.1 | 0.6 |
| Aknad1 | 0.0 | 0.1 | 2.7 | 0.0 | 0.0 | |
| Defb36 | 17.6 | 47.4 | 2.7 | 11.9 | 17.5 | 1.5 |
| LOC299282 | 0.0 | 0.1 | 2.7 | 0.0 | 0.1 | |
| Nab1 | 11.8 | 31.8 | 2.7 | 10.2 | 26.1 | 2.6 |
| Wisp1 | 0.0 | 0.1 | 2.7 | 0.0 | 0.1 | 3.0 |
| Cyp1a2 | 0.0 | 0.1 | 2.7 | 0.0 | 0.0 | |
| Ces1c | 0.1 | 0.2 | 2.7 | 0.0 | 0.0 | 0.0 |
| Hoga1 | 0.0 | 0.1 | 2.7 | 0.0 | 0.0 | |
| Nsg1 | 319.8 | 861.1 | 2.7 | 417.9 | 723.4 | 1.7 |
| Oas1h | 0.1 | 0.3 | 2.7 | 0.2 | 0.1 | 0.5 |
| Slc25a47 | 0.2 | 0.4 | 2.7 | 0.6 | 0.0 | 0.0 |
| RGD1564149 | 0.1 | 0.3 | 2.7 | 0.3 | 0.2 | 0.7 |
| Ppp1r32 | 0.6 | 1.5 | 2.7 | 0.5 | 1.4 | 3.1 |
| Gapdh-ps1 | 0.1 | 0.2 | 2.7 | 0.1 | 0.1 | 1.5 |
| Tuba8 | 0.1 | 0.2 | 2.7 | 0.1 | 0.1 | 1.0 |
| Dusp14 | 0.2 | 0.5 | 2.7 | 0.2 | 0.2 | 1.1 |
| Cldn14 | 0.1 | 0.2 | 2.7 | 0.0 | 0.1 | |
| Qk | 0.1 | 0.2 | 2.7 | 0.2 | 0.1 | 0.6 |
| Mid1ip1 | 226.4 | 608.7 | 2.7 | 517.5 | 958.3 | 1.9 |
| Rnf133 | 0.1 | 0.2 | 2.7 | 0.1 | 0.4 | 3.7 |
| Eid3 | 0.4 | 1.2 | 2.7 | 1.0 | 2.1 | 2.0 |
| Mef2b | 0.1 | 0.3 | 2.7 | 0.2 | 0.5 | 3.0 |
| Lipogenin | 0.1 | 0.2 | 2.7 | 0.0 | 0.2 | |
| Arr3 | 0.1 | 0.2 | 2.7 | 0.0 | 0.0 | |
| Pou5f2 | 0.1 | 0.2 | 2.7 | 0.2 | 0.0 | 0.0 |
| RGD1359334 | 0.1 | 0.2 | 2.7 | 0.0 | 0.0 | |
| Azgp1 | 0.2 | 0.6 | 2.7 | 0.2 | 0.3 | 1.1 |
| Rhoq | 3.9 | 10.5 | 2.7 | 3.7 | 5.3 | 1.4 |
| Pax4 | 0.1 | 0.2 | 2.7 | 0.2 | 0.2 | 1.0 |
| Coro1a | 18.2 | 48.9 | 2.7 | 28.2 | 45.7 | 1.6 |
| Atp6v1e2 | 0.1 | 0.2 | 2.7 | 0.3 | 0.2 | 0.7 |
| Map3k2 | 8.8 | 23.7 | 2.7 | 6.7 | 16.3 | 2.4 |
| Magi3 | 5.8 | 15.5 | 2.7 | 6.7 | 9.3 | 1.4 |
| Ninj2 | 0.2 | 0.6 | 2.7 | 0.0 | 0.0 | |
| LOC500594 | 0.1 | 0.3 | 2.7 | 0.1 | 0.0 | 0.0 |
| Baiap2l1 | 17.8 | 47.4 | 2.7 | 16.6 | 29.9 | 1.8 |
| Setl1 | 0.1 | 0.3 | 2.7 | 0.1 | 0.0 | 0.0 |
| Lpin1 | 9.6 | 25.6 | 2.7 | 12.8 | 22.2 | 1.7 |
| Eef1a1 | 54.1 | 144.1 | 2.7 | 165.7 | 175.7 | 1.1 |
| Mogat1 | 0.1 | 0.3 | 2.7 | 0.1 | 0.2 | 1.5 |
| RGD1309586 | 0.8 | 2.2 | 2.7 | 2.1 | 2.5 | 1.2 |
| Gsta4 | 0.1 | 0.4 | 2.7 | 0.3 | 0.2 | 0.5 |
| Trmt10c | 5.4 | 14.4 | 2.7 | 6.9 | 13.0 | 1.9 |
| Nudt18 | 3.0 | 8.0 | 2.7 | 1.9 | 0.9 | 0.5 |
| Uba2 | 2.4 | 6.4 | 2.7 | 4.9 | 6.3 | 1.3 |
| Sptbn1 | 152.6 | 405.9 | 2.7 | 190.3 | 297.2 | 1.6 |
| Spaca4 | 0.2 | 0.4 | 2.7 | 0.2 | 1.1 | 4.5 |
| Acot2 | 2.1 | 5.6 | 2.7 | 2.6 | 3.0 | 1.1 |
| Golga7 | 29.9 | 79.4 | 2.7 | 29.2 | 44.8 | 1.5 |
| Epas1 | 38.7 | 102.8 | 2.7 | 11.3 | 26.8 | 2.4 |
| H3f3b | 103.7 | 275.2 | 2.7 | 147.3 | 221.7 | 1.5 |
| Gpr19 | 7.6 | 20.3 | 2.7 | 10.1 | 15.9 | 1.6 |
| Ttc9 | 10.7 | 28.4 | 2.6 | 4.5 | 14.0 | 3.1 |
| Otud3 | 3.5 | 9.3 | 2.6 | 4.5 | 7.7 | 1.7 |
| Actg1 | 1.3 | 3.5 | 2.6 | 2.8 | 3.5 | 1.3 |
| Azin1 | 42.3 | 112.1 | 2.6 | 43.7 | 101.3 | 2.3 |
| Urb2 | 3.5 | 9.2 | 2.6 | 4.3 | 9.1 | 2.1 |
| Wdr43 | 14.9 | 39.4 | 2.6 | 30.3 | 41.5 | 1.4 |
| Pnrc1 | 22.8 | 60.3 | 2.6 | 16.6 | 35.3 | 2.1 |
| Ncl | 35.9 | 94.7 | 2.6 | 138.9 | 116.5 | 0.8 |
| Timp2 | 5.3 | 13.9 | 2.6 | 5.0 | 5.4 | 1.1 |
| Rpl32 | 0.2 | 0.6 | 2.6 | 0.0 | 0.3 | |
| Prpf38a | 23.8 | 62.5 | 2.6 | 34.6 | 46.3 | 1.3 |
| Thsd7a | 0.3 | 0.7 | 2.6 | 3.1 | 3.7 | 1.2 |
| Slc18a2 | 0.9 | 2.4 | 2.6 | 1.0 | 2.2 | 2.1 |
| Syncrip | 8.6 | 22.5 | 2.6 | 22.6 | 29.4 | 1.3 |
| Nrarp | 1.1 | 2.8 | 2.6 | 1.0 | 2.4 | 2.3 |
| Cebpz | 15.4 | 40.3 | 2.6 | 19.1 | 28.7 | 1.5 |
| Tars | 35.5 | 93.0 | 2.6 | 45.5 | 79.6 | 1.8 |
| Rps25 | 1.1 | 2.8 | 2.6 | 1.9 | 1.9 | 1.0 |
| Trim45 | 1.7 | 4.5 | 2.6 | 1.0 | 2.5 | 2.5 |
| Uspl1 | 12.3 | 32.1 | 2.6 | 19.6 | 30.0 | 1.5 |
| Prickle1 | 9.9 | 25.8 | 2.6 | 6.2 | 6.1 | 1.0 |
| Scgb1c1 | 0.3 | 0.7 | 2.6 | 0.4 | 0.0 | 0.0 |
| Eif3a | 65.2 | 170.6 | 2.6 | 103.8 | 103.9 | 1.0 |
| Mtss1l | 39.9 | 104.3 | 2.6 | 31.7 | 29.3 | 0.9 |
| Gnl1 | 54.9 | 143.4 | 2.6 | 70.0 | 95.2 | 1.4 |
| Mcu | 21.8 | 57.0 | 2.6 | 21.6 | 32.2 | 1.5 |
| NMS | 0.3 | 0.8 | 2.6 | 0.0 | 0.0 | |
| Ang1 | 0.3 | 0.8 | 2.6 | 4.3 | 3.9 | 0.9 |
| LOC287167 | 0.3 | 0.8 | 2.6 | 1.2 | 0.0 | 0.0 |
| Atp11a | 48.5 | 126.3 | 2.6 | 22.7 | 32.9 | 1.5 |
| Pop4 | 36.9 | 96.0 | 2.6 | 45.2 | 51.1 | 1.1 |
| Pfdn2 | 13.5 | 35.0 | 2.6 | 28.1 | 28.4 | 1.0 |
| Ctdp1 | 21.7 | 56.4 | 2.6 | 26.2 | 42.1 | 1.6 |
| LOC498231 | 0.2 | 0.4 | 2.6 | 0.4 | 0.6 | 1.5 |
| Mgat2 | 9.4 | 24.4 | 2.6 | 7.0 | 15.6 | 2.2 |
| Zfp347 | 1.5 | 4.0 | 2.6 | 1.4 | 5.2 | 3.6 |
| Dnaaf2 | 4.5 | 11.7 | 2.6 | 3.2 | 5.6 | 1.8 |
| Eif2ak1 | 47.3 | 122.3 | 2.6 | 48.6 | 96.1 | 2.0 |
| Srsf5 | 70.4 | 181.8 | 2.6 | 84.5 | 83.7 | 1.0 |
| Smim12 | 7.7 | 19.9 | 2.6 | 6.6 | 6.2 | 0.9 |
| Atp2b1 | 52.6 | 135.6 | 2.6 | 46.7 | 76.9 | 1.6 |
| Mkrn2 | 15.9 | 40.9 | 2.6 | 13.7 | 22.6 | 1.6 |
| Hcn4 | 30.5 | 78.6 | 2.6 | 21.7 | 24.8 | 1.1 |
| Gpatch21 | 4.5 | 11.5 | 2.6 | 3.1 | 7.0 | 2.3 |
| Astn2 | 0.7 | 1.8 | 2.6 | 0.7 | 0.9 | 1.3 |
| Amd1 | 30.8 | 79.1 | 2.6 | 36.4 | 61.4 | 1.7 |
| Mapk8ip1 | 143.0 | 366.6 | 2.6 | 149.8 | 285.3 | 1.9 |
| Prdm2 | 11.4 | 29.1 | 2.6 | 7.5 | 12.2 | 1.6 |
| Mki67ip | 32.3 | 82.9 | 2.6 | 43.3 | 53.4 | 1.2 |
| Tmx4 | 27.2 | 69.5 | 2.6 | 36.1 | 41.2 | 1.1 |
| Tmem189 | 118.4 | 302.4 | 2.6 | 91.4 | 184.1 | 2.0 |
| Cox7a2 | 2.2 | 5.6 | 2.6 | 1.9 | 4.7 | 2.6 |
| Gnb5 | 15.1 | 38.5 | 2.6 | 12.1 | 15.7 | 1.3 |
| Foxa1 | 5.8 | 14.7 | 2.6 | 3.3 | 23.9 | 7.3 |
| Hap1 | 52.5 | 133.8 | 2.6 | 45.9 | 72.8 | 1.6 |
| Oxnad1 | 7.4 | 18.8 | 2.6 | 8.9 | 10.5 | 1.2 |
| Usp12 | 0.8 | 2.0 | 2.5 | 0.6 | 0.6 | 1.0 |
| Pfn3 | 3.3 | 8.3 | 2.5 | 2.4 | 3.6 | 1.5 |
| Pou6f1 | 7.5 | 19.2 | 2.5 | 6.3 | 6.4 | 1.0 |
| Sms | 0.5 | 1.2 | 2.5 | 2.1 | 1.6 | 0.8 |
| Dctn1 | 162.3 | 412.5 | 2.5 | 129.1 | 185.6 | 1.4 |
| Eif5b | 0.7 | 1.9 | 2.5 | 1.8 | 1.1 | 0.6 |
| Cd200 | 30.1 | 76.3 | 2.5 | 34.2 | 64.6 | 1.9 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Cpn1 | 58.8 | 149.0 | 2.5 | 71.9 | 108.9 | 1.5 |
| Grin2c | 0.1 | 0.3 | 2.5 | 0.1 | 0.2 | 2.1 |
| Ntng2 | 0.3 | 0.7 | 2.5 | 1.2 | 2.5 | 2.1 |
| Tinf2 | 9.2 | 23.2 | 2.5 | 6.5 | 11.0 | 1.7 |
| Josd1 | 42.1 | 106.3 | 2.5 | 36.5 | 50.7 | 1.4 |
| Aebp2 | 10.5 | 26.6 | 2.5 | 14.6 | 24.6 | 1.7 |
| Tprn | 27.2 | 68.5 | 2.5 | 17.9 | 36.4 | 2.0 |
| Zfp655 | 0.5 | 1.4 | 2.5 | 0.8 | 0.8 | 1.0 |
| Slc25a33 | 3.7 | 9.4 | 2.5 | 5.4 | 7.9 | 1.5 |
| Tmed5 | 4.7 | 11.7 | 2.5 | 10.0 | 19.4 | 1.9 |
| Pnn | 19.2 | 48.2 | 2.5 | 31.8 | 36.8 | 1.2 |
| Mib2 | 7.7 | 19.4 | 2.5 | 7.9 | 8.8 | 1.1 |
| Impact | 21.0 | 52.4 | 2.5 | 18.8 | 22.7 | 1.2 |
| Man1b1 | 69.0 | 172.5 | 2.5 | 58.8 | 62.3 | 1.1 |
| Rpl31 | 6.8 | 17.1 | 2.5 | 7.3 | 9.6 | 1.3 |
| Mbnl2 | 46.9 | 117.2 | 2.5 | 38.8 | 78.3 | 2.0 |
| Slc2a13 | 2.3 | 5.8 | 2.5 | 0.8 | 2.1 | 2.5 |
| Pdha1 | 6.4 | 16.0 | 2.5 | 12.9 | 16.9 | 1.3 |
| Zfand5 | 22.1 | 54.9 | 2.5 | 33.3 | 44.6 | 1.3 |
| Filip1 | 8.9 | 22.1 | 2.5 | 9.8 | 14.4 | 1.5 |
| Il1r1 | 38.7 | 96.3 | 2.5 | 27.8 | 43.9 | 1.6 |
| Fzd3 | 3.4 | 8.4 | 2.5 | 5.0 | 7.2 | 1.4 |
| Pam | 158.4 | 393.7 | 2.5 | 190.9 | 331.6 | 1.7 |
| Lrfn4 | 49.3 | 122.4 | 2.5 | 50.5 | 96.4 | 1.9 |
| Zpbp | 0.8 | 1.9 | 2.5 | 0.6 | 0.8 | 1.4 |
| Cpa2 | 14.4 | 35.6 | 2.5 | 5.8 | 12.7 | 2.2 |
| Fabp3 | 18.2 | 45.2 | 2.5 | 106.9 | 116.9 | 1.1 |
| Id3 | 161.1 | 399.5 | 2.5 | 134.6 | 265.9 | 2.0 |
| Prcp | 8.1 | 20.0 | 2.5 | 13.5 | 21.5 | 1.6 |
| Srgap1 | 1.0 | 2.4 | 2.5 | 2.1 | 3.1 | 1.5 |
| Sema7a | 0.2 | 0.4 | 2.5 | 0.3 | 0.3 | 1.2 |
| Ntmt1 | 28.3 | 69.9 | 2.5 | 50.7 | 67.5 | 1.3 |
| Ccdc19 | 0.3 | 0.7 | 2.5 | 0.2 | 0.2 | 0.7 |
| Arhgap28 | 0.6 | 1.5 | 2.5 | 0.8 | 1.0 | 1.2 |
| Rreb1 | 9.9 | 24.4 | 2.5 | 9.4 | 17.0 | 1.8 |
| Rhbdl1 | 0.3 | 0.8 | 2.5 | 0.5 | 0.6 | 1.2 |
| Vav3 | 2.7 | 6.8 | 2.5 | 5.7 | 12.5 | 2.2 |
| Pbdc1 | 9.7 | 23.9 | 2.5 | 16.2 | 18.4 | 1.1 |
| Sacm1l | 8.8 | 21.6 | 2.5 | 9.3 | 10.3 | 1.1 |
| Itch | 13.4 | 33.1 | 2.5 | 12.6 | 17.4 | 1.4 |
| Btbd9 | 10.6 | 26.0 | 2.5 | 10.6 | 22.1 | 2.1 |
| Slc25a3 | 302.5 | 744.2 | 2.5 | 441.9 | 679.1 | 1.5 |
| Galnt10 | 36.5 | 89.7 | 2.5 | 46.1 | 67.1 | 1.5 |
| Impdh2 | 53.6 | 131.7 | 2.5 | 84.1 | 103.7 | 1.2 |
| Irf7 | 4.8 | 11.8 | 2.5 | 10.0 | 9.5 | 0.9 |
| Map1lc3a | 74.2 | 182.0 | 2.5 | 46.4 | 63.7 | 1.4 |
| Atf4 | 235.5 | 574.4 | 2.4 | 138.2 | 256.5 | 1.9 |
| Per2 | 8.8 | 21.3 | 2.4 | 4.5 | 12.7 | 2.8 |
| Gtpbp4 | 1.2 | 2.9 | 2.4 | 1.7 | 2.4 | 1.4 |
| Kitlg | 0.4 | 0.9 | 2.4 | 2.4 | 4.4 | 1.8 |
| Hnrnph2 | 91.0 | 221.3 | 2.4 | 120.2 | 142.3 | 1.2 |
| Prima1 | 0.1 | 0.3 | 2.4 | 0.0 | 0.1 | 1.5 |
| Cldn1 | 0.4 | 0.9 | 2.4 | 0.4 | 0.7 | 1.7 |
| Dmgdh | 0.1 | 0.3 | 2.4 | 0.1 | 0.1 | 1.0 |
| Rnf138 | 2.0 | 4.8 | 2.4 | 2.7 | 3.5 | 1.3 |
| Fem1a | 49.9 | 121.2 | 2.4 | 49.1 | 84.8 | 1.7 |
| Slc26a5 | 0.2 | 0.4 | 2.4 | 0.0 | 0.0 | 1.5 |
| Ccrl2 | 0.2 | 0.5 | 2.4 | 0.2 | 0.3 | 1.5 |
| Mxi1 | 26.5 | 64.1 | 2.4 | 36.9 | 35.4 | 1.0 |
| Rgs16 | 54.7 | 132.4 | 2.4 | 122.8 | 209.8 | 1.7 |
| RGD1309104 | 33.3 | 80.7 | 2.4 | 21.5 | 34.7 | 1.6 |
| Rbm47 | 47.5 | 114.9 | 2.4 | 42.7 | 64.2 | 1.5 |
| Fhdc1 | 29.0 | 70.2 | 2.4 | 24.6 | 27.5 | 1.1 |
| Gramd3 | 35.3 | 85.4 | 2.4 | 18.0 | 34.4 | 1.9 |
| Smim14 | 80.7 | 194.9 | 2.4 | 19.4 | 36.2 | 1.9 |
| Ucn3 | 1.3 | 3.2 | 2.4 | 0.0 | 0.0 | |
| Slc35c1 | 35.8 | 86.3 | 2.4 | 49.1 | 130.0 | 2.6 |
| Dnmt3a | 21.8 | 52.3 | 2.4 | 21.4 | 34.7 | 1.6 |
| Tgfbr3 | 2.3 | 5.4 | 2.4 | 2.0 | 4.2 | 2.2 |
| Nt5dc3 | 44.9 | 107.9 | 2.4 | 21.3 | 58.8 | 2.8 |
| Dnaja2 | 46.8 | 112.6 | 2.4 | 84.3 | 94.7 | 1.1 |
| Agpat6 | 39.8 | 95.6 | 2.4 | 53.8 | 60.7 | 1.1 |
| Apod | 0.6 | 1.3 | 2.4 | 0.1 | 0.4 | 4.5 |
| RGD1560888 | 37.9 | 91.0 | 2.4 | 58.3 | 83.2 | 1.4 |
| Atp5g1 | 183.4 | 440.6 | 2.4 | 201.6 | 281.6 | 1.4 |
| Naa50 | 3.0 | 7.2 | 2.4 | 4.8 | 8.5 | 1.7 |
| Cyp2c23 | 0.4 | 0.9 | 2.4 | 0.5 | 0.9 | 1.8 |
| Itpkb | 59.5 | 142.5 | 2.4 | 3.4 | 6.1 | 1.8 |
| Socs2 | 49.4 | 118.2 | 2.4 | 28.2 | 35.1 | 1.2 |
| Dyrk2 | 13.9 | 33.4 | 2.4 | 12.7 | 18.2 | 1.4 |
| Ubl3 | 284.8 | 681.3 | 2.4 | 124.3 | 273.2 | 2.2 |
| Flna | 2.6 | 6.2 | 2.4 | 5.0 | 8.4 | 1.7 |
| Wdr1 | 129.8 | 310.3 | 2.4 | 129.6 | 203.2 | 1.6 |
| Spag9 | 29.1 | 69.4 | 2.4 | 28.9 | 40.2 | 1.4 |
| Sez6l | 5.0 | 11.8 | 2.4 | 0.3 | 1.0 | 3.0 |
| Usp51 | 8.6 | 20.5 | 2.4 | 10.9 | 28.0 | 2.6 |
| Nefm | 4.6 | 10.9 | 2.4 | 3.7 | 5.7 | 1.6 |
| Hnrph1 | 77.2 | 183.9 | 2.4 | 142.3 | 165.5 | 1.2 |
| RGD1306119 | 4.0 | 9.5 | 2.4 | 4.1 | 8.3 | 2.0 |
| Fahd1 | 26.0 | 61.7 | 2.4 | 25.5 | 37.0 | 1.5 |
| Srsf3 | 21.4 | 50.7 | 2.4 | 28.2 | 36.7 | 1.3 |
| Pragmin | 3.1 | 7.5 | 2.4 | 4.3 | 15.1 | 3.5 |
| Fam108b1 | 12.3 | 29.1 | 2.4 | 16.6 | 20.4 | 1.2 |
| Chp | 7.8 | 18.4 | 2.4 | 9.0 | 12.2 | 1.4 |
| Flcn | 27.0 | 63.9 | 2.4 | 29.6 | 27.5 | 0.9 |
| Get4 | 73.7 | 174.6 | 2.4 | 93.0 | 94.5 | 1.0 |
| Grin2b | 0.1 | 0.1 | 2.4 | 0.0 | 0.0 | |
| Bhlhe40 | 23.6 | 55.9 | 2.4 | 95.7 | 76.9 | 0.8 |
| Tcf7l2 | 0.9 | 2.2 | 2.4 | 1.0 | 2.6 | 2.6 |
| Taf7 | 9.9 | 23.3 | 2.4 | 11.6 | 12.3 | 1.1 |
| Il18r1 | 0.1 | 0.3 | 2.4 | 0.2 | 0.1 | 0.6 |
| Uap1l1 | 8.7 | 20.6 | 2.4 | 5.2 | 6.8 | 1.3 |
| Tmem63c | 16.8 | 39.7 | 2.4 | 21.4 | 26.3 | 1.2 |
| Gtf2a2 | 3.1 | 7.4 | 2.4 | 3.7 | 6.3 | 1.7 |
| Th | 0.4 | 0.9 | 2.4 | 0.1 | 0.2 | 1.5 |
| Cyp2d3 | 0.2 | 0.5 | 2.4 | 0.2 | 0.2 | 1.1 |
| Uri1 | 6.2 | 14.6 | 2.4 | 8.8 | 8.4 | 1.0 |
| Tnk1 | 19.8 | 46.6 | 2.4 | 17.7 | 34.5 | 2.0 |
| Ssr3 | 75.7 | 178.0 | 2.3 | 77.6 | 114.4 | 1.5 |
| Ppfibp2 | 0.4 | 1.0 | 2.3 | 0.1 | 0.2 | 2.4 |
| Nampt | 11.9 | 28.0 | 2.3 | 16.3 | 21.8 | 1.3 |
| Col16a1 | 2.8 | 6.6 | 2.3 | 1.3 | 1.6 | 1.2 |
| Heca | 6.4 | 15.0 | 2.3 | 9.4 | 9.5 | 1.0 |
| RGD1359108 | 5.8 | 13.6 | 2.3 | 8.9 | 15.2 | 1.7 |
| Ehd4 | 5.1 | 12.0 | 2.3 | 5.4 | 8.7 | 1.6 |
| RGD1563216 | 1.3 | 3.0 | 2.3 | 2.4 | 2.0 | 0.8 |
| Clic4 | 52.9 | 123.7 | 2.3 | 26.1 | 59.2 | 2.3 |
| Iqcb1 | 6.3 | 14.8 | 2.3 | 5.7 | 5.9 | 1.0 |
| Bag2 | 9.4 | 21.9 | 2.3 | 9.7 | 9.6 | 1.0 |
| Cryba4 | 0.5 | 1.1 | 2.3 | 0.5 | 1.2 | 2.4 |
| Rrp1 | 30.5 | 71.3 | 2.3 | 48.6 | 50.7 | 1.0 |
| Galnt11 | 25.7 | 60.0 | 2.3 | 15.4 | 19.3 | 1.3 |
| Dd25 | 6.5 | 15.2 | 2.3 | 5.2 | 8.7 | 1.7 |
| Prex1 | 50.8 | 118.1 | 2.3 | 84.1 | 105.9 | 1.3 |
| Mcfd2 | 41.4 | 96.4 | 2.3 | 32.7 | 52.9 | 1.6 |
| Epm2aip1 | 36.3 | 84.4 | 2.3 | 30.2 | 43.7 | 1.4 |
| Fbxo33 | 6.3 | 14.6 | 2.3 | 5.7 | 10.7 | 1.9 |
| Pomc | 3.3 | 7.7 | 2.3 | 4.3 | 4.6 | 1.1 |
| Pde4b | 2.2 | 5.0 | 2.3 | 5.5 | 10.5 | 1.9 |
| Hic2 | 3.1 | 7.1 | 2.3 | 2.5 | 4.3 | 1.7 |
| Mllt11 | 31.8 | 73.5 | 2.3 | 35.1 | 90.9 | 2.6 |
| Mccc2 | 18.1 | 41.8 | 2.3 | 16.5 | 23.9 | 1.4 |
| Mab21l1 | 0.5 | 1.1 | 2.3 | 0.5 | 0.5 | 1.1 |
| Gabarapl2 | 7.7 | 17.7 | 2.3 | 7.9 | 10.3 | 1.3 |
| Man1a1 | 1.1 | 2.5 | 2.3 | 3.7 | 5.7 | 1.6 |
| Cdk12 | 21.4 | 49.3 | 2.3 | 17.3 | 33.4 | 1.9 |
| Adra2a | 20.6 | 47.6 | 2.3 | 13.1 | 44.1 | 3.4 |
| Sar1a | 79.9 | 184.5 | 2.3 | 85.3 | 102.3 | 1.2 |
| Idi1 | 12.5 | 28.7 | 2.3 | 14.0 | 22.8 | 1.6 |
| Ube2j1 | 55.1 | 126.8 | 2.3 | 32.7 | 59.8 | 1.8 |
| Orc2 | 6.4 | 14.6 | 2.3 | 6.3 | 11.2 | 1.8 |
| Golph3 | 30.5 | 70.3 | 2.3 | 34.0 | 55.9 | 1.6 |
| Trim36 | 0.8 | 1.8 | 2.3 | 1.3 | 1.8 | 1.4 |
| Odc1 | 23.5 | 54.1 | 2.3 | 39.4 | 62.2 | 1.6 |
| Rdh16 | 1.4 | 3.2 | 2.3 | 0.7 | 0.6 | 1.0 |
| Mvk | 29.0 | 66.6 | 2.3 | 37.5 | 31.5 | 0.8 |
| Slc10a3 | 15.0 | 34.4 | 2.3 | 12.8 | 15.4 | 1.2 |
| Onecut1 | 0.3 | 0.8 | 2.3 | 0.8 | 1.2 | 1.4 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Gstm4 | 42.2 | 96.6 | 2.3 | 90.5 | 136.2 | 1.5 |
| Supt16h | 28.2 | 64.7 | 2.3 | 36.8 | 41.5 | 1.1 |
| Shank3 | 18.8 | 43.0 | 2.3 | 15.3 | 21.7 | 1.4 |
| Asb1 | 5.1 | 11.6 | 2.3 | 4.3 | 8.8 | 2.0 |
| Marcksl1 | 1.1 | 2.4 | 2.3 | 7.8 | 8.1 | 1.0 |
| Phlpp2 | 13.1 | 30.0 | 2.3 | 10.7 | 17.9 | 1.7 |
| Phf17 | 17.7 | 40.5 | 2.3 | 19.0 | 17.1 | 0.9 |
| Grwd1 | 24.3 | 55.5 | 2.3 | 42.8 | 66.1 | 1.5 |
| Trpc5 | 0.3 | 0.8 | 2.3 | 0.3 | 0.4 | 1.1 |
| Slc35e4 | 16.7 | 38.2 | 2.3 | 12.0 | 16.3 | 1.4 |
| Dync1li1 | 22.5 | 51.3 | 2.3 | 22.1 | 32.6 | 1.5 |
| Tbc1d10a | 6.4 | 14.6 | 2.3 | 6.3 | 7.3 | 1.1 |
| Lysmd3 | 10.6 | 24.2 | 2.3 | 5.4 | 11.0 | 2.0 |
| Rorb | 1.1 | 2.4 | 2.3 | 2.4 | 8.2 | 3.4 |
| Adcy9 | 13.6 | 31.1 | 2.3 | 10.1 | 18.6 | 1.8 |
| Ebf3 | 15.5 | 35.1 | 2.3 | 6.5 | 21.9 | 3.4 |
| Gpd2 | 103.6 | 235.6 | 2.3 | 80.0 | 159.7 | 2.0 |
| Bzw1 | 10.6 | 24.0 | 2.3 | 22.4 | 29.7 | 1.3 |
| Rnf41 | 41.4 | 94.0 | 2.3 | 46.4 | 67.7 | 1.5 |
| Pabpc2 | 0.7 | 1.6 | 2.3 | 2.1 | 1.7 | 0.8 |
| Tceal8 | 30.2 | 68.5 | 2.3 | 28.8 | 34.7 | 1.2 |
| Rpl12 | 8.7 | 19.8 | 2.3 | 19.4 | 21.8 | 1.1 |
| Bex2 | 203.0 | 459.6 | 2.3 | 214.1 | 214.5 | 1.0 |
| Cd63 | 824.8 | 1865.5 | 2.3 | 946.0 | 994.7 | 1.1 |
| Hspa4l | 9.2 | 20.7 | 2.3 | 12.3 | 14.8 | 1.2 |
| Kras | 14.6 | 32.9 | 2.3 | 24.5 | 27.0 | 1.1 |
| Pkhd1l1 | 0.0 | 0.0 | 2.3 | 0.1 | 0.1 | 1.1 |
| Zbtb11 | 12.2 | 27.6 | 2.3 | 14.8 | 23.8 | 1.6 |
| Lyn | 10.7 | 24.2 | 2.3 | 6.1 | 8.0 | 1.3 |
| Actl7b | 1.9 | 4.2 | 2.3 | 1.1 | 1.6 | 1.4 |
| Tfrc | 41.7 | 94.1 | 2.3 | 89.4 | 124.9 | 1.4 |
| Abca17 | 0.0 | 0.1 | 2.3 | 0.1 | 0.1 | 1.0 |
| Tbk1 | 10.6 | 24.0 | 2.3 | 10.8 | 13.2 | 1.2 |
| Gorab | 3.9 | 8.8 | 2.3 | 3.8 | 6.7 | 1.8 |
| Scara5 | 0.1 | 0.1 | 2.3 | 0.4 | 1.5 | 3.7 |
| Cd164 | 258.4 | 581.4 | 2.3 | 240.1 | 382.1 | 1.6 |
| Adam11 | 0.2 | 0.4 | 2.2 | 0.7 | 0.4 | 0.6 |
| Sqstm1 | 367.8 | 827.0 | 2.2 | 383.3 | 637.5 | 1.7 |
| Fam126b | 2.2 | 4.9 | 2.2 | 2.1 | 6.0 | 2.9 |
| LOC500475 | 0.2 | 0.5 | 2.2 | 0.6 | 0.2 | 0.3 |
| Nfe2 | 0.1 | 0.3 | 2.2 | 0.1 | 0.1 | 1.0 |
| Gpr160 | 0.2 | 0.3 | 2.2 | 0.1 | 0.2 | 3.0 |
| Syt5 | 180.7 | 405.0 | 2.2 | 245.1 | 355.1 | 1.4 |
| RGD1308706 | 2.6 | 5.8 | 2.2 | 5.5 | 11.5 | 2.1 |
| Ufm1 | 39.3 | 88.1 | 2.2 | 52.7 | 78.9 | 1.5 |
| Isg20l2 | 3.2 | 7.2 | 2.2 | 3.7 | 6.1 | 1.6 |
| Selk | 21.7 | 48.6 | 2.2 | 14.7 | 18.8 | 1.3 |
| Hs3st3a1 | 0.2 | 0.5 | 2.2 | 0.0 | 0.3 | |
| Rpp25l | 38.9 | 87.0 | 2.2 | 60.3 | 68.0 | 1.1 |
| Tesk1 | 21.0 | 46.9 | 2.2 | 25.8 | 57.8 | 2.2 |
| Piga | 4.3 | 9.7 | 2.2 | 0.9 | 2.8 | 3.0 |
| Cetn4 | 0.5 | 1.2 | 2.2 | 1.0 | 1.3 | 1.3 |
| Zfp868 | 6.2 | 13.8 | 2.2 | 7.3 | 12.4 | 1.7 |
| Crybb1 | 0.3 | 0.6 | 2.2 | 1.3 | 1.2 | 1.0 |
| Samd4b | 26.6 | 59.3 | 2.2 | 28.4 | 38.6 | 1.4 |
| Golga3 | 1.1 | 2.5 | 2.2 | 1.7 | 1.8 | 1.0 |
| Prkx | 5.2 | 11.5 | 2.2 | 9.5 | 17.4 | 1.8 |
| Rps24 | 52.5 | 116.7 | 2.2 | 107.5 | 103.8 | 1.0 |
| Ddx58 | 3.2 | 7.0 | 2.2 | 4.7 | 2.5 | 0.5 |
| Celf6 | 7.4 | 16.5 | 2.2 | 4.7 | 6.3 | 1.4 |
| Irak3 | 0.7 | 1.6 | 2.2 | 0.6 | 0.3 | 0.6 |
| LOC498750 | 6.5 | 14.3 | 2.2 | 9.0 | 7.6 | 0.8 |
| Atp5d | 371.4 | 823.3 | 2.2 | 546.3 | 874.4 | 1.6 |
| Sf1 | 146.4 | 324.4 | 2.2 | 134.6 | 273.3 | 2.0 |
| Urgcp | 23.2 | 51.4 | 2.2 | 16.5 | 28.9 | 1.8 |
| Enah | 138.1 | 305.9 | 2.2 | 99.9 | 146.5 | 1.5 |
| Olfm1 | 19.1 | 42.2 | 2.2 | 10.3 | 18.8 | 1.8 |
| Mtr | 7.7 | 17.0 | 2.2 | 8.5 | 10.5 | 1.2 |
| Peli1 | 2.9 | 6.5 | 2.2 | 3.8 | 5.3 | 1.4 |
| Etv1 | 64.7 | 142.9 | 2.2 | 106.0 | 171.5 | 1.6 |
| Eprs | 78.2 | 172.8 | 2.2 | 60.4 | 73.4 | 1.2 |
| Man2a1 | 14.8 | 32.6 | 2.2 | 25.6 | 51.7 | 2.0 |
| Ostm1 | 8.6 | 19.0 | 2.2 | 8.1 | 11.2 | 1.4 |
| Slc30a7 | 27.6 | 60.8 | 2.2 | 31.3 | 75.8 | 2.4 |
| Ctrb1 | 2.8 | 6.1 | 2.2 | 9.7 | 8.9 | 0.9 |
| Lemd3 | 12.2 | 26.8 | 2.2 | 10.0 | 15.6 | 1.6 |
| Creb3 | 52.5 | 115.6 | 2.2 | 51.6 | 84.1 | 1.6 |
| Hyou1 | 135.3 | 298.0 | 2.2 | 59.4 | 75.2 | 1.3 |
| Hdac5 | 87.5 | 192.6 | 2.2 | 73.4 | 72.0 | 1.0 |
| Lmbrd1 | 12.8 | 28.2 | 2.2 | 13.7 | 18.6 | 1.4 |
| Sfpq | 129.7 | 285.5 | 2.2 | 218.1 | 346.8 | 1.6 |
| Zfyve9 | 5.8 | 12.8 | 2.2 | 6.0 | 6.8 | 1.1 |
| Pcmtd1 | 4.3 | 9.5 | 2.2 | 5.1 | 5.5 | 1.1 |
| Ankrd9 | 9.1 | 20.0 | 2.2 | 4.6 | 10.9 | 2.4 |
| Slc35d1 | 12.9 | 28.3 | 2.2 | 20.3 | 42.8 | 2.1 |
| LOC100363289 | 2.5 | 5.6 | 2.2 | 3.3 | 2.8 | 0.9 |
| Gfod1 | 3.9 | 8.5 | 2.2 | 5.1 | 9.2 | 1.8 |
| Sytl1 | 0.3 | 0.7 | 2.2 | 0.2 | 0.1 | 0.9 |
| St8sia4 | 2.1 | 4.7 | 2.2 | 2.3 | 7.0 | 3.1 |
| Fam181b | 0.4 | 1.0 | 2.2 | 0.1 | 0.3 | 2.0 |
| RGD1562310 | 19.5 | 42.5 | 2.2 | 15.5 | 32.3 | 2.1 |
| Nop58 | 35.7 | 78.0 | 2.2 | 65.3 | 75.8 | 1.2 |
| PVR | 9.5 | 20.7 | 2.2 | 10.1 | 26.8 | 2.7 |
| Fam91a1 | 22.9 | 49.9 | 2.2 | 27.3 | 42.3 | 1.5 |
| Actn4 | 132.5 | 289.2 | 2.2 | 159.2 | 267.9 | 1.7 |
| Orc4 | 2.9 | 6.3 | 2.2 | 4.2 | 4.5 | 1.1 |
| Scx | 0.6 | 1.3 | 2.2 | 0.2 | 0.2 | 0.7 |
| RT1-CE3 | 0.6 | 1.3 | 2.2 | 1.3 | 1.8 | 1.3 |
| Ptpro | 0.3 | 0.6 | 2.2 | 2.3 | 3.5 | 1.5 |
| Morf4l2 | 230.3 | 499.9 | 2.2 | 343.1 | 393.8 | 1.1 |
| Agfg1 | 17.2 | 37.3 | 2.2 | 16.5 | 30.6 | 1.9 |
| Ptprn | 275.6 | 597.4 | 2.2 | 202.4 | 346.1 | 1.7 |
| Sclt1 | 4.3 | 9.4 | 2.2 | 3.1 | 3.6 | 1.2 |
| Syap1 | 20.0 | 43.3 | 2.2 | 21.2 | 30.2 | 1.4 |
| Pdzd8 | 8.8 | 19.0 | 2.2 | 7.7 | 19.1 | 2.5 |
| Tubb4a | 113.4 | 245.3 | 2.2 | 111.8 | 210.0 | 1.9 |
| Ippk | 14.5 | 31.5 | 2.2 | 13.5 | 18.0 | 1.3 |
| Nptxr | 63.5 | 137.3 | 2.2 | 55.4 | 88.6 | 1.6 |
| Trpv3 | 2.5 | 5.5 | 2.2 | 0.2 | 0.8 | 3.5 |
| Anp32e | 95.5 | 206.2 | 2.2 | 210.3 | 189.0 | 0.9 |
| Sec61a1 | 237.2 | 512.0 | 2.2 | 223.8 | 323.2 | 1.4 |
| Lrrc73 | 43.6 | 93.9 | 2.2 | 80.4 | 122.1 | 1.5 |
| Pcdhga2 | 0.3 | 0.6 | 2.2 | 0.2 | 0.6 | 3.0 |
| Pcsk1 | 14.3 | 30.7 | 2.2 | 7.4 | 9.3 | 1.3 |
| Spata2 | 19.6 | 42.0 | 2.1 | 15.2 | 31.4 | 2.1 |
| Brd1 | 30.1 | 64.6 | 2.1 | 34.6 | 51.7 | 1.5 |
| Lsm5 | 7.4 | 15.8 | 2.1 | 17.4 | 14.1 | 0.8 |
| S100a5 | 4.1 | 8.7 | 2.1 | 34.8 | 42.5 | 1.2 |
| Il17rb | 6.4 | 13.7 | 2.1 | 16.9 | 14.9 | 0.9 |
| Clock | 10.6 | 22.7 | 2.1 | 8.9 | 15.4 | 1.7 |
| C1qa | 2.7 | 5.7 | 2.1 | 4.9 | 6.2 | 1.3 |
| Foxj3 | 37.4 | 80.1 | 2.1 | 28.7 | 67.6 | 2.4 |
| LOC100365935 | 9.9 | 21.3 | 2.1 | 4.7 | 3.2 | 0.7 |
| Slc23a2 | 10.0 | 21.3 | 2.1 | 9.1 | 23.8 | 2.6 |
| Exog | 3.1 | 6.6 | 2.1 | 5.5 | 6.9 | 1.3 |
| Ccnh | 11.3 | 24.2 | 2.1 | 15.4 | 21.9 | 1.4 |
| Ift172 | 11.4 | 24.4 | 2.1 | 6.0 | 6.5 | 1.1 |
| Xpot | 17.8 | 38.0 | 2.1 | 20.6 | 22.7 | 1.1 |
| Tmed7 | 43.9 | 93.5 | 2.1 | 48.9 | 73.4 | 1.5 |
| LOC688869 | 5.6 | 11.9 | 2.1 | 11.9 | 7.7 | 0.6 |
| Pgam1 | 311.7 | 664.1 | 2.1 | 450.6 | 716.3 | 1.6 |
| Smek1 | 17.0 | 36.2 | 2.1 | 22.3 | 36.8 | 1.6 |
| Tdp2 | 8.0 | 17.1 | 2.1 | 9.6 | 13.0 | 1.4 |
| Klf13 | 13.2 | 28.0 | 2.1 | 7.0 | 25.1 | 3.6 |
| Mapk6 | 25.8 | 54.9 | 2.1 | 22.3 | 27.4 | 1.2 |
| Spire1 | 11.6 | 24.8 | 2.1 | 12.5 | 15.3 | 1.2 |
| Scarb1 | 212.9 | 452.1 | 2.1 | 178.9 | 269.2 | 1.5 |
| Kcnab1 | 0.2 | 0.3 | 2.1 | 0.2 | 0.3 | 1.7 |
| Tmie | 0.2 | 0.4 | 2.1 | 0.2 | 0.1 | 0.6 |
| Neto2 | 10.9 | 23.1 | 2.1 | 22.0 | 42.8 | 1.9 |
| Ttc7 | 14.7 | 31.2 | 2.1 | 8.2 | 12.9 | 1.6 |
| Bop1 | 38.9 | 82.4 | 2.1 | 57.9 | 80.1 | 1.4 |
| Tradd | 5.1 | 10.7 | 2.1 | 1.8 | 3.2 | 1.8 |
| Eif2c3 | 5.6 | 11.9 | 2.1 | 6.3 | 12.2 | 1.9 |
| Wnk1 | 78.2 | 165.3 | 2.1 | 53.5 | 126.7 | 2.4 |
| Xkr6 | 1.1 | 2.4 | 2.1 | 0.8 | 1.9 | 2.4 |
| Zfp61 | 36.3 | 76.8 | 2.1 | 17.7 | 31.2 | 1.8 |
| Pde7b | 1.4 | 3.0 | 2.1 | 5.8 | 8.5 | 1.4 |

TABLE 2-continued

RNAseq values and fold inductions in INS1 cells grown in chronic high glucose compared to controls and stimulated with FSK.

| | Low control | Low FSK | Fold | High control | High FSK | Fold |
|---|---|---|---|---|---|---|
| Spata25 | 0.4 | 0.8 | 2.1 | 0.7 | 0.5 | 0.7 |
| Rpl19 | 196.7 | 415.8 | 2.1 | 438.4 | 529.6 | 1.2 |
| Etf1 | 26.1 | 55.1 | 2.1 | 31.3 | 41.1 | 1.3 |
| Crnkl1 | 0.5 | 1.1 | 2.1 | 1.3 | 0.7 | 0.6 |
| Sh3bgrl2 | 5.5 | 11.6 | 2.1 | 6.1 | 11.5 | 1.9 |
| Tmem176b | 1.1 | 2.2 | 2.1 | 1.6 | 1.8 | 1.2 |
| Npm1 | 65.7 | 138.3 | 2.1 | 150.4 | 188.4 | 1.3 |
| Rpl22l1 | 20.8 | 43.8 | 2.1 | 32.4 | 38.8 | 1.2 |
| Scml4 | 4.4 | 9.2 | 2.1 | 2.0 | 1.2 | 0.6 |
| Stk40 | 34.0 | 71.5 | 2.1 | 26.4 | 45.0 | 1.7 |
| Zdhhc5 | 54.4 | 114.4 | 2.1 | 45.7 | 73.6 | 1.6 |
| LOC500625 | 0.5 | 1.1 | 2.1 | 1.3 | 1.6 | 1.2 |
| Ubn1 | 27.0 | 56.7 | 2.1 | 26.1 | 36.4 | 1.4 |
| Txnl1 | 141.1 | 295.4 | 2.1 | 157.0 | 227.7 | 1.5 |
| Clcnka | 1.0 | 2.1 | 2.1 | 1.3 | 1.4 | 1.1 |
| Rpl11 | 88.6 | 185.3 | 2.1 | 257.2 | 250.0 | 1.0 |
| Adat3 | 6.2 | 12.9 | 2.1 | 8.8 | 12.9 | 1.5 |
| Slc4a7 | 2.0 | 4.2 | 2.1 | 2.5 | 6.1 | 2.4 |
| Hdlbp | 72.7 | 151.9 | 2.1 | 75.4 | 112.7 | 1.5 |
| Txndc17 | 20.7 | 43.3 | 2.1 | 26.8 | 30.4 | 1.1 |
| LOC500035 | 5.4 | 11.2 | 2.1 | 5.2 | 23.4 | 4.5 |
| Trak1 | 33.2 | 69.4 | 2.1 | 28.1 | 46.6 | 1.7 |
| Zcchc12 | 67.1 | 139.9 | 2.1 | 57.4 | 94.9 | 1.7 |
| Strap | 56.7 | 118.3 | 2.1 | 90.8 | 124.7 | 1.4 |
| Hsp90b1 | 466.3 | 971.0 | 2.1 | 375.0 | 395.7 | 1.1 |
| Ivns1abp | 56.9 | 118.5 | 2.1 | 74.0 | 98.9 | 1.3 |
| Pdcd4 | 43.4 | 89.9 | 2.1 | 54.2 | 57.4 | 1.1 |
| LOC500959 | 5.5 | 11.4 | 2.1 | 10.4 | 14.0 | 1.3 |
| Mien1 | 1.2 | 2.4 | 2.1 | 1.7 | 2.3 | 1.4 |
| Ppp4r2 | 18.0 | 37.2 | 2.1 | 28.7 | 30.0 | 1.0 |
| Zfp472 | 1.8 | 3.6 | 2.1 | 3.8 | 3.9 | 1.0 |
| Ywhaz | 346.3 | 715.2 | 2.1 | 473.1 | 656.9 | 1.4 |
| Zfp131 | 8.6 | 17.8 | 2.1 | 9.5 | 12.3 | 1.3 |
| Pdgfa | 15.0 | 31.1 | 2.1 | 16.0 | 36.0 | 2.2 |
| LOC687575 | 146.3 | 301.9 | 2.1 | 210.9 | 214.8 | 1.0 |
| Efhd2 | 7.0 | 14.5 | 2.1 | 9.7 | 12.9 | 1.3 |
| Rps29 | 18.8 | 38.8 | 2.1 | 23.2 | 32.0 | 1.4 |
| Tob2 | 23.4 | 48.3 | 2.1 | 17.9 | 19.0 | 1.1 |
| Mthfd2 | 57.4 | 118.3 | 2.1 | 36.1 | 68.0 | 1.9 |
| Clk4 | 9.3 | 19.1 | 2.1 | 7.5 | 11.8 | 1.6 |
| Phf8 | 8.8 | 18.1 | 2.1 | 7.3 | 13.4 | 1.8 |
| Pnmal2 | 229.2 | 471.8 | 2.1 | 142.7 | 126.6 | 0.9 |
| Bdh1 | 32.4 | 66.7 | 2.1 | 49.2 | 80.2 | 1.6 |
| Pom121 | 81.1 | 166.8 | 2.1 | 80.7 | 138.5 | 1.7 |
| Tm4sf4 | 243.9 | 501.4 | 2.1 | 204.3 | 315.8 | 1.5 |
| Entpd6 | 11.7 | 24.0 | 2.1 | 15.3 | 19.4 | 1.3 |
| Plxna2 | 0.4 | 0.9 | 2.1 | 1.0 | 1.3 | 1.3 |
| Tbx15 | 1.2 | 2.4 | 2.1 | 2.4 | 2.0 | 0.8 |
| Ppard | 9.6 | 19.7 | 2.1 | 6.9 | 13.6 | 2.0 |
| Cyth3 | 15.0 | 30.7 | 2.0 | 16.8 | 54.2 | 3.2 |
| Vps37b | 25.4 | 52.0 | 2.0 | 24.5 | 32.2 | 1.3 |
| Dkc1 | 42.9 | 87.8 | 2.0 | 79.6 | 97.6 | 1.2 |
| Usp9x | 27.4 | 56.0 | 2.0 | 27.4 | 40.0 | 1.5 |
| Hnrpdl | 78.2 | 160.1 | 2.0 | 110.7 | 165.3 | 1.5 |
| Rab11fip1 | 5.4 | 11.0 | 2.0 | 4.4 | 8.3 | 1.9 |
| Pde3b | 50.8 | 103.8 | 2.0 | 23.9 | 45.5 | 1.9 |
| LOC686295 | 2.4 | 4.9 | 2.0 | 2.9 | 3.8 | 1.3 |
| Fn1 | 417.3 | 852.9 | 2.0 | 118.1 | 320.4 | 2.7 |
| Kdm1b | 4.5 | 9.1 | 2.0 | 5.7 | 8.1 | 1.4 |
| Agt | 2.6 | 5.2 | 2.0 | 2.6 | 4.7 | 1.8 |
| Taf1a | 4.4 | 9.0 | 2.0 | 5.0 | 6.7 | 1.3 |
| Mef2d | 71.5 | 146.0 | 2.0 | 95.8 | 175.0 | 1.8 |
| Fmc1 | 12.7 | 26.0 | 2.0 | 26.7 | 28.5 | 1.1 |
| Rap2a | 6.6 | 13.5 | 2.0 | 5.9 | 12.9 | 2.2 |
| Rab3gap2 | 26.0 | 53.1 | 2.0 | 22.7 | 29.1 | 1.3 |
| Gars | 215.3 | 439.6 | 2.0 | 175.8 | 308.1 | 1.8 |
| Ccni | 118.6 | 242.1 | 2.0 | 156.2 | 240.1 | 1.5 |
| Bhlha15 | 31.3 | 63.9 | 2.0 | 10.3 | 10.9 | 1.1 |
| Canx | 118.5 | 241.6 | 2.0 | 117.7 | 134.4 | 1.1 |
| Nolc1 | 90.2 | 183.8 | 2.0 | 159.3 | 192.8 | 1.2 |
| LOC683722 | 6.0 | 12.3 | 2.0 | 4.4 | 7.9 | 1.8 |
| Ormdl3 | 140.9 | 286.8 | 2.0 | 119.0 | 128.5 | 1.1 |
| Sncaip | 3.7 | 7.4 | 2.0 | 3.4 | 4.9 | 1.4 |
| Snapc1 | 2.3 | 4.6 | 2.0 | 2.3 | 2.7 | 1.2 |
| Hmcn1 | 0.0 | 0.0 | 2.0 | 0.1 | 0.0 | 0.3 |
| Myof | 0.0 | 0.0 | 2.0 | 0.1 | 0.1 | 0.6 |
| Btg3 | 71.9 | 145.9 | 2.0 | 51.0 | 63.0 | 1.2 |
| Stard8 | 0.2 | 0.3 | 2.0 | 0.2 | 0.4 | 2.3 |
| Nckap1l | 0.1 | 0.2 | 2.0 | 2.0 | 1.8 | 0.9 |
| Megf10 | 0.0 | 0.1 | 2.0 | 0.0 | 0.2 | |
| Plcb2 | 0.0 | 0.1 | 2.0 | 0.0 | 0.0 | 1.0 |
| Il13ra1 | 0.1 | 0.3 | 2.0 | 0.2 | 0.2 | 1.0 |
| Rpl17 | 58.0 | 117.5 | 2.0 | 128.6 | 126.3 | 1.0 |
| Pabpc6 | 0.0 | 0.1 | 2.0 | 0.0 | 0.1 | 4.4 |
| Epha3 | 0.1 | 0.1 | 2.0 | 0.1 | 0.0 | 0.5 |
| Tomm20 | 44.5 | 90.1 | 2.0 | 49.5 | 70.0 | 1.4 |
| Lrfn5 | 0.1 | 0.1 | 2.0 | 0.1 | 0.2 | 1.2 |
| Gabre | 0.1 | 0.1 | 2.0 | 0.0 | 0.0 | |
| Hspd1 | 23.5 | 47.6 | 2.0 | 63.0 | 63.0 | 1.0 |
| Kif9 | 0.1 | 0.3 | 2.0 | 0.1 | 0.0 | 0.7 |
| Map3k4 | 12.6 | 25.4 | 2.0 | 16.9 | 22.7 | 1.3 |
| Hs3st2 | 0.3 | 0.6 | 2.0 | 0.4 | 1.0 | 2.6 |
| Otop3 | 0.1 | 0.1 | 2.0 | 0.1 | 0.0 | 0.0 |
| Accsl | 0.1 | 0.3 | 2.0 | 0.1 | 0.1 | 0.9 |
| Msn | 0.6 | 1.2 | 2.0 | 3.1 | 3.2 | 1.0 |
| Chd1 | 10.3 | 20.8 | 2.0 | 17.2 | 24.3 | 1.4 |
| Ahi1 | 16.1 | 32.6 | 2.0 | 12.3 | 18.6 | 1.5 |
| Bysl | 27.8 | 56.1 | 2.0 | 38.3 | 56.8 | 1.5 |
| Epor | 0.1 | 0.2 | 2.0 | 0.1 | 0.1 | 1.0 |
| Spon2 | 0.4 | 0.7 | 2.0 | 0.4 | 0.3 | 0.7 |
| Zfp385d | 0.1 | 0.2 | 2.0 | 0.3 | 0.1 | 0.2 |
| Twistnb | 4.0 | 8.1 | 2.0 | 5.9 | 9.1 | 1.5 |
| Hnrnpa1 | 16.9 | 34.2 | 2.0 | 24.6 | 35.4 | 1.4 |
| Rrs1 | 19.0 | 38.4 | 2.0 | 46.4 | 71.4 | 1.5 |
| Chrne | 0.1 | 0.2 | 2.0 | 0.2 | 0.0 | 0.0 |
| Smad1 | 24.0 | 48.4 | 2.0 | 20.9 | 29.8 | 1.4 |
| RGD1311084 | 0.1 | 0.2 | 2.0 | 0.0 | 0.0 | |
| Rho | 0.1 | 0.2 | 2.0 | 0.1 | 0.1 | 0.7 |
| Sgce | 0.1 | 0.2 | 2.0 | 0.3 | 0.3 | 0.8 |
| T2 | 0.1 | 0.2 | 2.0 | 0.1 | 0.1 | 0.7 |
| Tmem114 | 0.1 | 0.2 | 2.0 | 0.0 | 0.0 | |
| Tpp2 | 6.0 | 12.0 | 2.0 | 9.8 | 12.3 | 1.3 |
| Smad3 | 2.8 | 5.7 | 2.0 | 2.2 | 1.6 | 0.7 |
| Ctf1 | 0.1 | 0.2 | 2.0 | 0.2 | 0.4 | 1.8 |
| Hspa4 | 68.7 | 138.6 | 2.0 | 91.8 | 113.8 | 1.2 |
| Icam2 | 0.1 | 0.2 | 2.0 | 0.2 | 0.0 | 0.0 |
| Fam49a | 0.1 | 0.2 | 2.0 | 0.2 | 0.1 | 1.0 |
| Nkx2-2 | 95.3 | 192.1 | 2.0 | 43.0 | 93.4 | 2.2 |
| Kcnj13 | 0.7 | 1.4 | 2.0 | 0.3 | 0.8 | 3.0 |
| Ggt5 | 0.1 | 0.3 | 2.0 | 0.0 | 0.0 | |
| Zfp830 | 10.1 | 20.4 | 2.0 | 15.4 | 17.0 | 1.1 |
| Pdrg1 | 21.6 | 43.4 | 2.0 | 28.6 | 28.6 | 1.0 |
| Notch4 | 0.5 | 0.9 | 2.0 | 0.4 | 0.6 | 1.7 |
| Acpt | 0.1 | 0.3 | 2.0 | 0.1 | 0.2 | 3.0 |
| Il28ra | 5.0 | 10.0 | 2.0 | 4.0 | 6.8 | 1.7 |
| Cxcl2 | 0.5 | 1.0 | 2.0 | 0.1 | 0.4 | 3.2 |
| Syp | 370.0 | 744.1 | 2.0 | 292.1 | 447.7 | 1.5 |
| Pde4dip | 30.7 | 61.8 | 2.0 | 21.0 | 29.3 | 1.4 |
| Srp54 | 19.9 | 40.0 | 2.0 | 24.2 | 27.8 | 1.1 |
| Gnmt | 0.2 | 0.4 | 2.0 | 0.0 | 0.0 | |
| Acsl4 | 14.3 | 28.6 | 2.0 | 15.5 | 24.1 | 1.6 |
| Ficd | 44.8 | 89.9 | 2.0 | 13.4 | 15.9 | 1.2 |
| Gzmm | 0.2 | 0.4 | 2.0 | 0.5 | 0.0 | 0.0 |
| Gnl3 | 15.5 | 31.0 | 2.0 | 17.5 | 23.1 | 1.3 |
| RGD1309079 | 0.5 | 1.1 | 2.0 | 0.6 | 0.8 | 1.3 |
| Kcnb1 | 24.3 | 48.7 | 2.0 | 15.9 | 13.1 | 0.8 |
| Rpl7a | 0.2 | 0.4 | 2.0 | 0.3 | 0.7 | 2.5 |
| LOC689959 | 8.9 | 17.9 | 2.0 | 7.9 | 7.2 | 0.9 |
| Hmga2 | 0.2 | 0.5 | 2.0 | 0.4 | 0.0 | 0.0 |
| Tex38 | 0.2 | 0.5 | 2.0 | 0.5 | 0.1 | 0.3 |

Figure 9:
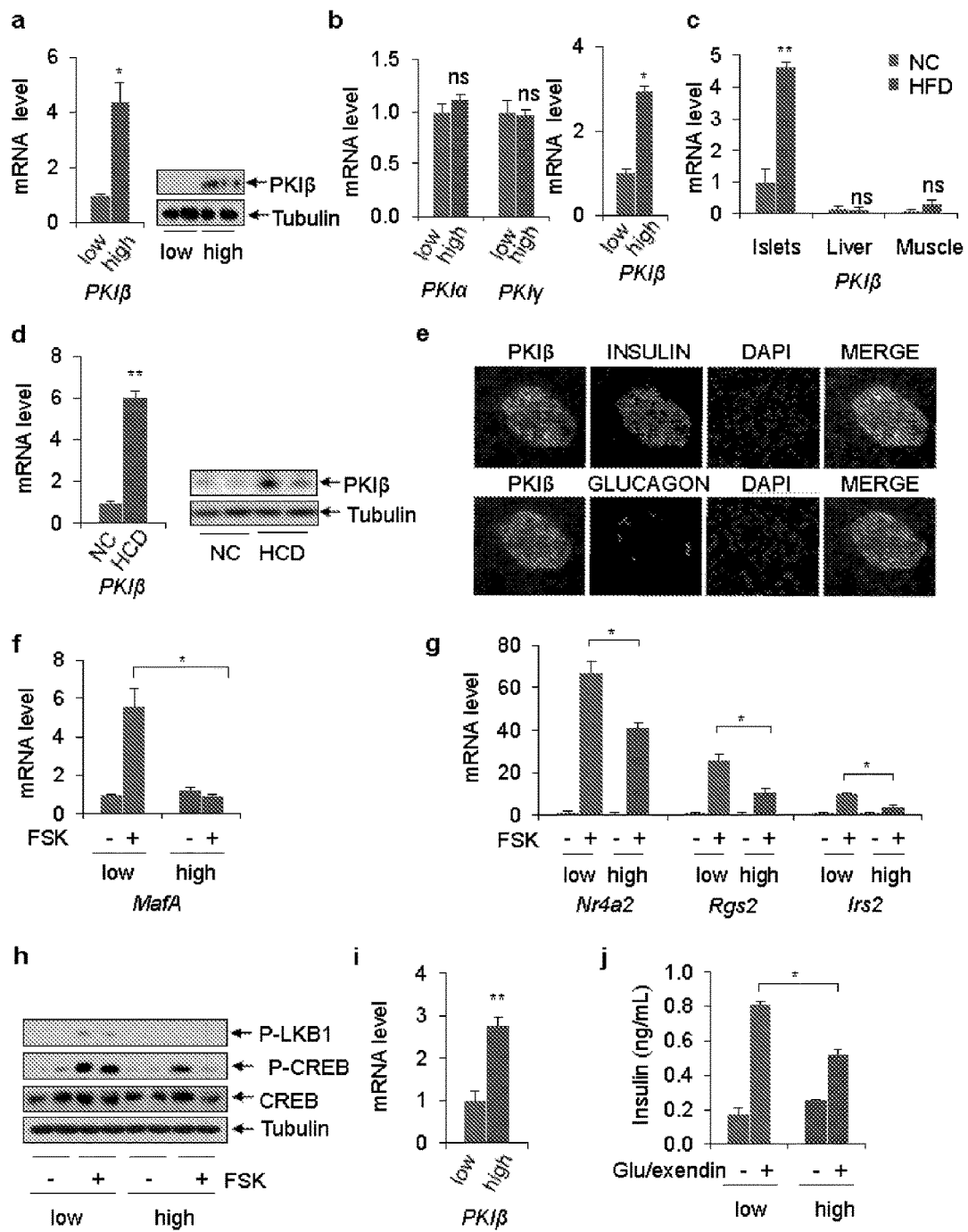
FIG. 9: High Glucose Exposure stimulates expression of PKIB. Chronic increases in glucose exposure trigger expression of PKIB in pancreatic islets. a. Effect of prolonged exposure of cultured mouse islets to high glucose on induction of PKIB mRNA and protein (*p<0.05. n=4). b. mRNA amounts for PKIA, PKIB, and PKIG in INS1 cells maintained on high glucose as described above (*p<0.05. n=6). c. Effect of HFD feeding on PKIB mRNA amounts in islets versus other tissues (liver, skeletal muscle) (p<0.01. n=4). d. Effect of HCD feeding on PKIB expression (p<0.01. n=4). e. Immunostaining of mouse pancreatic islets showing relative colocalization of PKIB with glucagon or insulin (n=6). f. and g. mRNA amounts for MafA (f) and other CREB target genes (g) in human islets maintained under low (2.8 mM) or high (20 mM) glucose conditions for 3 days. Exposure to FSK for 2 hours shown (*p<0.05. n=4). h. and i. Effect of low and high glucose exposure on CREB phosphorylation (h) and PKIB mRNA accumulation (i). Exposure to FSK indicated (**p<0.01. n=4). j. Effect of exendin treatment on insulin secretion from human islets maintained under low or high glucose conditions (*p<0.05. n=3).

Having seen that chronic glucose exposure disrupts PKA activity without affecting cAMP accumulation, the inventors considered the involvement of a Protein Kinase A Inhibitor (PKI) in this process. Consisting of three closely related polypeptides (PKIA, PKIB, PKIG) the PKIs have been shown to bind with high specificity and affinity to PKA; they also contain a potent nuclear export signal that maintains PKA in the cytoplasm (Taylor et al., 2005) (Fantozzi et al., 1994; Wen et al., 1994; Wen et al., 1995). PKIB was selectively upregulated in INS1 cells and cultured pancreatic islets following prolonged exposure to high glucose (FIGS. 9a and 9b). Indeed, PKIB mRNA and protein amounts were also increased in pancreatic islets but not other metabolic tissues from HFD and HCD fed mice relative to controls (FIG. 3f; FIGS. 9c and 9d).

In immunohistochemical studies, PKIB was detected in beta cells of the pancreatic islets, but not in surrounding glucagon producing alpha cells or in acinar cells of the exocrine pancreas (FIG. 9e). Similar to its effects in mouse islets, chronic glucose exposure also promoted PKIB expression in human islets, thereby attenuating CREB phosphorylation and target gene expression (FIGS. 9f-9j).

Based on its proposed role in nuclear export, it was reasoned that PKIB may reduce CREB phosphorylation by blocking the nuclear accumulation of PKA. Supporting this idea, exposure to FSK promoted an increase in nuclear amounts of PKA catalytic subunit in INS1 cells maintained under low glucose conditions but not in cells maintained on high glucose (FIG. 3g).

Figure 4:
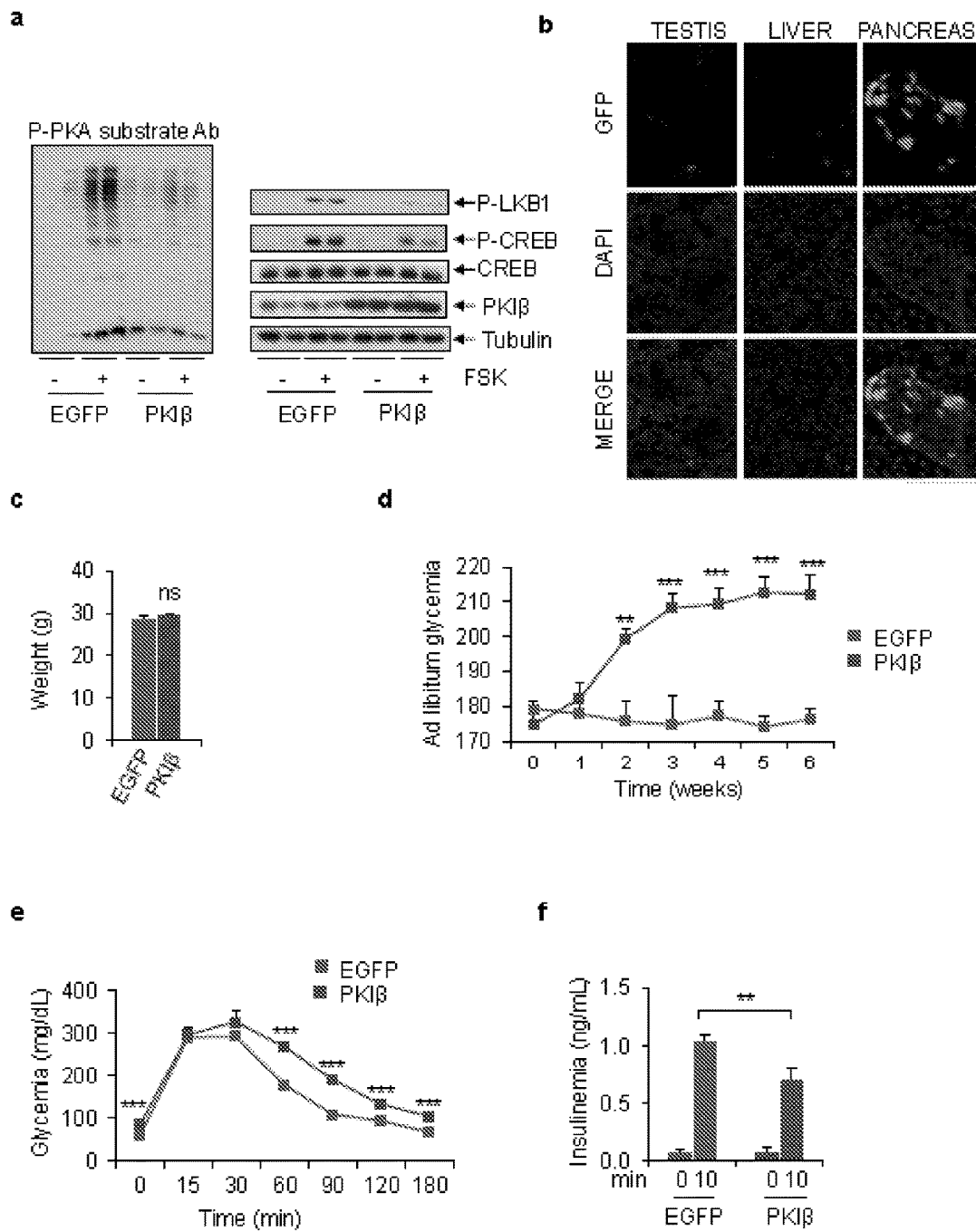
FIG. 4: PKIB Disrupts Beta Cell Function. a Immunoblots showing effect of dsAAV-MIP-PKIB expression on PKA activity using phospho-PKA substrate antibody (left) or phospho-CREB and phospho LKB antiserum (right) in MIN6 cells (n=4). b. Immunohistochemical analysis of GFP expression from AAV encoded EGFP virus in testis, liver and pancreas 10 days after injection (n=3). c. and d. Body weight (c) as well as circulating ad libitum glucose concentrations in mice infected with PKIB (the higher plot, indicated by filled black squares) or control EGFP (d) (p<0.01, *p<0.01; n=5) e. and f. Circulating glucose (OGTT) and insulin concentrations in mice following oral glucose administration (f) (p<0.01, *p<0.01; n=5). Data are shown as mean±s.e.m.

Although PKI potently inhibits PKA activity, the importance of this pathway for insulin secretion is unclear, as increases in circulating glucose modulate insulin secretion primilary through calcium signaling. In that event, the PKIB would cause only modest changes in circulating glucose and insulin concentrations. To evaluate the effects of this inhibitor on glucose homeostasis, the inventors employed a double stranded AAV8 vector expressing PKIB under control of the mouse insulin promoter, which targets transgene expression specifically to beta cells. Over-expression of AAV8-encoded PKIB in MIN6 insulinoma cells reduced PKA activity and correspondingly disrupted CREB phosphorylation in response to FSK treatment (FIG. 4a). Following intraperitoneal administration, a control AAV-MIP-EGFP virus was expressed in pancreatic islets but not other tissues such as liver and testis (FIG. 4b). Ad libitum circulating glucose concentrations increased progressively over a 6 weeks period in mice expressing AAV encoded PKIB (FIGS. 4c and 4d). Although their body weights were identical to controls, PKIB-over-expressing animals became relatively glucose intolerant and they had lower circulating concentrations of insulin in response to oral glucose tolerance testing, indicating that PKIB expression is sufficient to disrupt beta cell function (FIGS. 4e and 4f).

Figure 5:
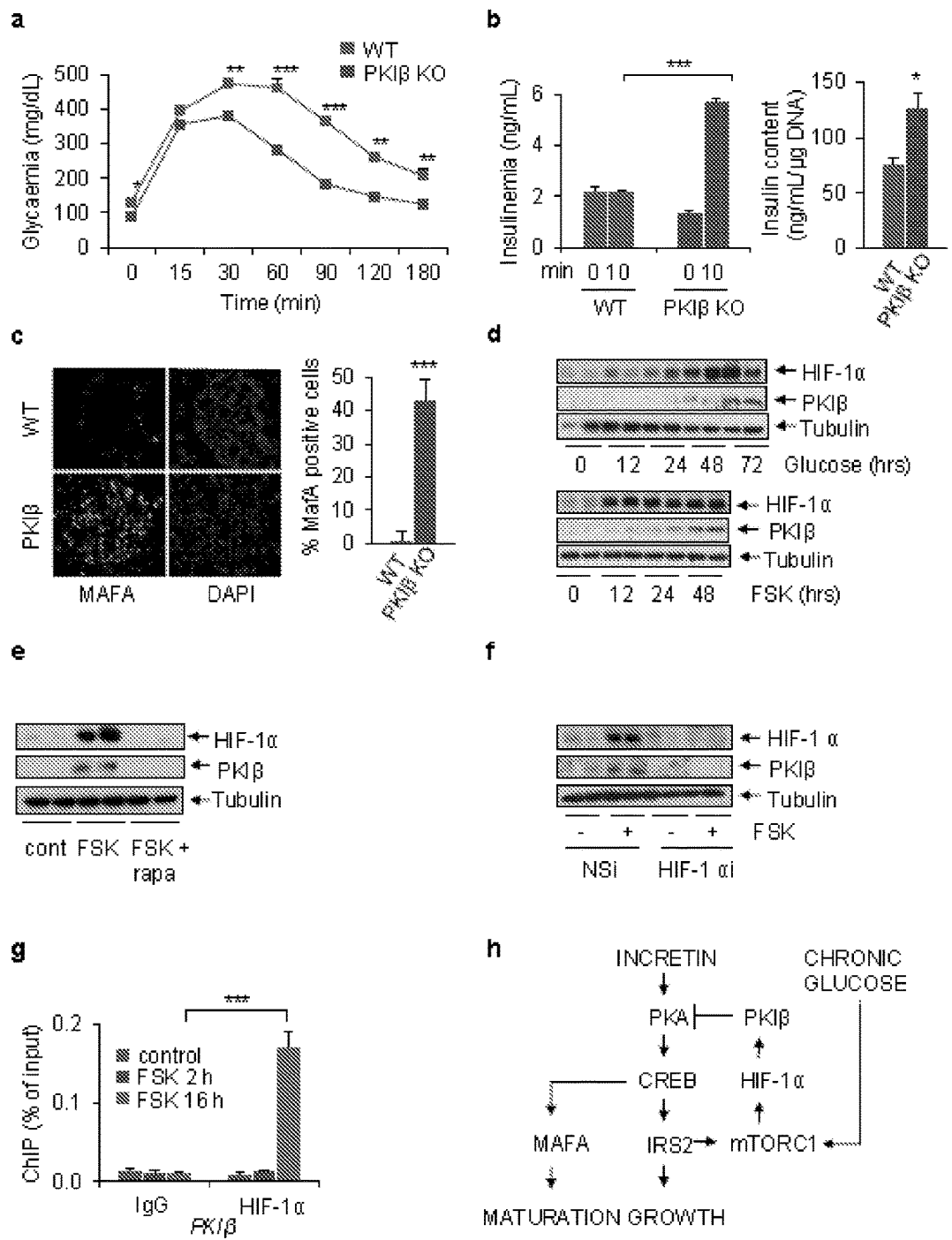
FIG. 5: Knockout of PKIB Improves Pancreatic Islet Function in insulin resistance. a. OGTT of PKIB (the lower plot, indicated by filled black squares) knockout and control littermates maintained on a HFD for 12 weeks. (p<0.01, *p<0.01; n=6) b. Circulating insulin concentrations in control and PKIB mutant littermates under basal conditions and 10 minutes following oral glucose administration. Right, relative insulin content in isolated pancreatic islets (*p<0.05, *p<0.01; n=6). c Immunohistochemical analysis showing MafA staining in pancreatic sections from HFD-fed control mice and PKIB−/− littermates. d. Time course of PKIB mRNA accumulation in INS1 cells exposed to FSK (n=4). e. Effect of mTORC1 inhibitor rapamycin on PKIB mRNA amounts in INS1 cells exposed to FSK for 14 hours (n=4). f. Effect of HIF-1α RNAi-mediated knockdown on PKIB mRNA levels in INS1 cells (n=4). g. ChiP assays showing effect of short (2 hr) or long term (16 hrs) exposure to FSK on HIF-1α occupancy over the PKIB promoter (*p<0.001; n=6). h. Feedback regulation of beta cell CREB activity in insulin resistance. Glucose and incretin dependent increases in CREB/CRTC2 activity during feeding promote the expression of IRS2, which in turn mediates induction of mTORC1 complexes. When hyperglycemia is prolonged, increases in HIF-1 protein trigger expression of PKIB, which down-regulates the CREB/CRTC2 pathway by binding to and inhibiting PKA. Data are shown as mean±s.e.m.
Figure 10:
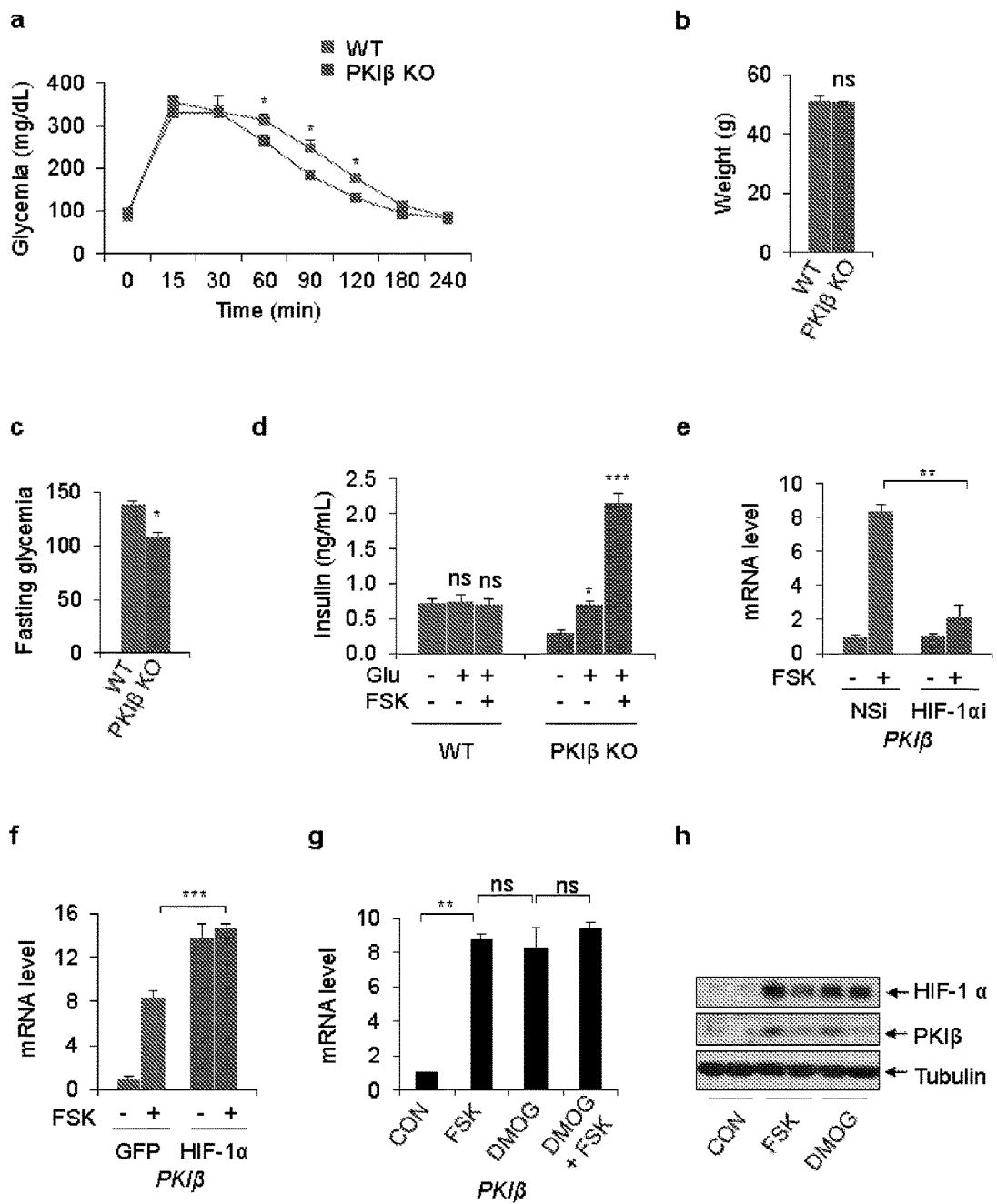
FIG. 10: Effect of HFD feeding on pancreatic islet function in PKIB knockout mice. The mTORC1/HIF1 pathway mediates induction of PKIB in response to chronic glucose stimulation. a. OGTT testing of PKIB KO (the lower plot, indicated by filled black squares) and wild-type littermates maintained on a normal chow diet (*p<0.05. n=5). b.-d.

Mice with a knockout of PKIB were used to determine whether the upregulation of this inhibitor in response to high fat diet feeding contributes to the deterioration in pancreatic islet function. Although they were otherwise unremarkable (Belyamani et al., 2001), NC-fed PKIB KO mice were modestly more glucose tolerant relative to wild-type littermates by OGTT (FIG. 10a). When placed on a HFD, however, PKIB mutants had lower fasting blood glucose concentrations and were substantially more glucose tolerant (FIG. 5a, FIGS. 10b-10d). Moreover, circulating insulin concentrations rose 3-fold in PKIB knockout mice following glucose administration, but they remained unchanged in controls (FIG. 5b). Similarly, MafA expression was strongly reduced in pancreatic sections from control mice following HFD-feeding, but it remained high in PKIB KO mice (FIG. 5c). Taken together, these results demonstrate that the upregulation of PKIB in insulin resistance disrupts beta cell CREB activity and insulin secretion.

In the setting of insulin resistance, chronic hyperglycemia is thought to promote beta cell hypertrophy in part through the induction of the energy sensing kinase mTOR. Indeed, prolonged exposure of pancreatic islets to glucose or FSK triggers the mTORC1-dependent activation of HIF-1α (Van de Velde et al., 2011) in beta cells, prompting the evaluation of the role of this pathway in mediating the induction of PKIB. Exposure of INS1 cells to glucose or FSK increased HIF-1α protein amounts after 12-24 hours followed by increases in PKIB protein amounts (FIG. 5d).

Consistent with a requirement for mTOR activity, exposure to the mTORC1 inhibitor rapamycin effectively blocked the upregulation of PKIB in cells exposed to FSK (FIG. 5e). Moreover, RNAi-mediated depletion of HIF-1α also disrupted PKIB induction, whereas HIF-1α over-expression potentiated it (FIG. 5f, FIGS. 10e and 10f). The effect of HIF on PKIB expression appears direct; HIF1 protein amounts over consensus binding sites on the PKIB promoter increased following prolonged but not short term FSK treatment of INS1 cells by ChIP assay (FIG. 5g). Indeed, selective induction of endogenous HIF1, by administration of the prolyl hydroxylase inhibitor DMOG, also upregulated PKIB expression, demonstrating that HIF is sufficient for induction of PKIB in beta cells (FIGS. 10g and 10h).

Taken together, the results show how CRTC2 mediates effects of incretin hormones through upregulation of MafA and other CREB target genes that promote insulin gene expression and secretion (FIG. 5h). In response to nutrient stress, GLP1 and glucose promote pancreatic islet function through increases in mTORC1 activity that culminate in the induction of the HIF pathway. When insulin resistance is prolonged, HIF1 inhibits CREB activity by stimulating the expression of PKIB and blocking the activation of PKA (FIG. 5h). Although prolonged exposure to FSK led to induction of PKIB in cultured islets, chronic treatment of insulin-resistant mice with GLP-1R agonist improved glucose intolerance in vivo (Irwin et al., 2009). Incretin signaling accounts for a large fraction of post-prandial glucose disposal, and the attenuation of this pathway in type II diabetes is thought to contribute significantly to the increased glucose excursions that are characteristic of this disease (Holst et al., 2011). Indeed, a sizable percentage of type II diabetic patients appear to be unresponsive to GLP1 agonist therapy (Buysschaert et al., 2012; Hall et al., 2013; Preumont et al., 2012), potentially reflecting the upregulation of PKIs. Although the mechanism is unclear, PKIA also appears to be upregulated in pancreatic islets from type II diabetic individuals (Gunton et al., 2005). Reducing the expression of PKIs in beta cells may provide therapeutic benefit in this setting.

EXAMPLE 2

Materials and Methods

Animals

All studies except for high fat and high carbohydrate diets studies were performed using 10 to 12 weeks old males mice in a C57Bl6 background. Animals were adapted to their environment for 1 week before studies and were housed in colony cages with a 12 hours light/12 hours dark cycle in a temperature-controlled environment. C57BL6 were purchased from Jackson laboratories. For high fat diet studies, C57BL6 mice were fed with high fat diet for 20 weeks beginning at 8 weeks of age (60% kcal fat, D12492, Research Diet Inc). Age-matched C57BL6 on normal chow were used as controls. For high carbohydrate diet studies, 8 weeks old males C57BL6 where maintain in diet with 73% carbohydrate during 10 weeks (AIN-93M, Resarch Diet Inc). PKIB mice were purchased from MMRRC (B6.129P2-Pkib$^{tm1Idz}$/Mmmh) MIP-CreERT mice were a gift from Dr. Phillipson of the University of Chicago. The CRTC2$^{flox/flox}$ mice are homozygous for a "floxed" CRTC2 allele in which CRTC2 exons 1 and 5 are flanked by loxP target sites for Cre recombinase. Animal studies were approved by the Institutional Animal Care and Use Committee (IACUC) at the Salk Institute.

In Vivo Analysis

At 10 weeks of age, CRTC2 flox/flox MIP-Cre/ERT mice (MIP-T2 KO mice) were fed with tamoxifen (sigma, T5648) dissolved in corn oil at 100 mg/kg body weight (once per day for 5 days). Following tamoxifen administration, the mice were housed for 5-10 days before being used and analyzed for Cre-recombinase activity. MIP-T2 KO mice fed with corn oil were used as controls. Following an overnight fast, mice were administered glucose (1 g/Kg) by oral gavage or by i.p., and glucose levels were measured every 30 minutes over a 3 hours period. Insulin tolerance was tested by i.p. injection of 6-hour fasted mice with 1 U/Kg of insulin (Humulin R, Eli Lilly) followed by blood glucose measurements every 15 minutes until 1 hour. For insulin dosage, blood was taking from the tail vein after 10 minutes of glucose gavage. dsAAV infections were carried out at a dose of a 4×10$^{11}$ genomes (vg) per mouse. Viruses were administrated intraperitoneally in a total volume of 800 µL of sterile saline solution containing 5% sorbitol.

Cell Culture and cAMP Measurement

INS-1 insulinoma cells were cultured in RPMI (corning cellgro) containing 10% fetal bovine serum (Gemini Bio Products), 100 µg/mL penicillin-streptomycin and 1 mM sodium pyruvate (corning cellgro). MIN6 cells were grown in DMEM (corning cellgro) with 10% FBS, 100 µg/mL penicillin-streptomycin and 70 uM beta-mercaptoethanol. For chronic glucose experiments, cells were maintained under low (2.8 mM) or high (20 mM) glucose for 3 days. Exendin-4 (10 nM), Forskolin (10 µM), KCl (40 mM), DMOG (1 mM) and rapamycin (50 nM) were added to cells as indicated. Cellular cAMP levels were measured using an ELISA kit (Cayman Chemical Company) according to manufacturer's instructions.

RNA Interference

The sequences of the oligonucleotides used for target rat mafA were as follows: 5'-GAGGAUCUGUAVUGGAUGA-3' (SEQ ID NO: 69) and 5' UCAUCCAGUACAGAUC-CUC-3' (SEQ ID NO: 70). As for a negative control, RNA duplexes targeting GFP were used: 5'-GCAAGCUGAC-CCUGAAGUUC-3' (SEQ ID NO: 71); and 5'-GAAC-UUCAGGGUCAGCUUGC-3' (SEQ ID NO: 72). After annealing 100 pmol of synthetic RNA duplex using Lipofectamine 2000 reagent (Invitrogen) per well (6 well plates) and cells were harvest 48 hours later.

Islet Isolation and Human Islets

Briefly, pancreata from 10 to 12 weeks old mice were injected with liberase (0.2 mg/mL, Roche Applied Science) and digest at 37° C. for 15 minutes. Preparations were washed with Hank's buffered salt solution and the dissociated islets were purified on histopaque gradients (Sigma Aldrich) and cultured in RPMI with 10% FBS for 3 days before testing. Human islets were supplied by the Integrated islets Distribution Program (IIDP) (http://iidp.coh.org/). Donor's information is listed in Table 3 below.

TABLE 3

Human islets donor's information.

| Donor ID | Age | Gender | BMI | Race | Cause of death |
|---|---|---|---|---|---|
| AAI4274 | 42 | Male | 22.76 | African American | Anoxia |
| AAJX077 | 59 | Male | 23.5 | N/A | Stroke |

Insulin Secretion:

INS-1 cells or primary islets were starved 2 hours in Krebs-Ringer Bicarbonate Hepes buffer (KRBH) containing 0.2% BSA and exposed to 2.8 mM or 20 mM glucose with or without FSK (10 µM) or exendin 4 (10 nM) for 1 hour. Insulin release and content were measured using the ultrasensitive insulin ELISA kit (Mercodia). Results are presented as insulin secretion (ng/mL) per hour normalized to insulin content. Insulin content is normalized to DNA. Insulin dosage in vivo, was assayed using the ultra sensitive mouse insulin ELISA (Crystal Chem).

Adenoviruses

For adenoviruses construction, cDNA were subcloned in the pAdTRACK vector. Rat PKIB cDNA was obtained by PCR using primers 5'-CAT CTCGAGATGAGGACAGATTC (sense; SEQ ID NO: 73) and 5'-CATGGTACCTTATTTGT CTTCGTCTAG (antisense; SEQ ID NO: 74), which introduces XhoI and KpnI sites (underlined) respectively. Complete viral vectors were generated by homologous recombination with the AdEASY vector as described (Koo et al., 2005). The MafA adenovirus was a gift from Dr. Matsuoka TA. Adenoviruses were then produced in MGH cells and purified using CsCl gradients. dsAAV-MIP-EGFP was a gift from Dr. Paul D. Robbins of the University of Pittsburgh. Mouse PKIB cDNA was obtained by PCR using primers 5'-CAT ACCGGTATGAGGACAGATTCATCAGA (sense; SEQ ID NO: 75) and (anti-sense; SEQ ID NO: 76)
5'-CATGCGGCCGCTCATTTTCCTTCATTTAG, which introduces AgeI and NotI (underlined) respectively. The dsAAV virus expressing mouse PKIβ was generated by excising EGFP with restriction enzymes AgeI and NotI. Recombinant dsAAV vectors were generating according to the triple transfection protocol using AAV8 serotype.

Real-Time Quantitative PCR and RNAseq

Total RNAs from cells or primary islets were extracted using Trizol and cDNA was generated using the Transcriptor First Strand cDNA Synthesis kit (Roche Applied Science). cDNAs were quantified on a lightcycler 480 instrument (Roche Applied Science). Gene expression data were presented relative to the expression of housekeeping gene L32 (rat samples) and 18S (mouse and human islets). Primer sequences are listed in Table 4 below. RNA-Seq libraries were prepared using the mRNA isolation protocol and the NEBNext-Ultra kits from New England Biolabs following the manufacturer's protocols. Libraries were quantitated by Qubit (Invitrogen), and run on a MiSeq instrument with paired-end 75 bp reads using v3 chemistry (Illumina) Data were analyzed by tophat2 and cuffdiff against the mouse mm10 genome build. The GEO accession number for RNAseq studies reported in the paper is GSE60158.

TABLE 4

Oligonucleotides used for Q-PCR analysis

| Target cDNA (rat) | | Primer sequence (SEQ ID NOs: 17-34) |
|---|---|---|
| GLP1R | Fw | 5'-CTGCTTTGTCAACAATGAGGTC-3' |
| | Rev | 5'-GTCCCTCTGGATGTTCAAGC-3' |
| IRS2 | Fw | 5'-TCATGGGCATGTAGCCATCA-3' |
| | Rev | 5'-TCTCCCAAAGTGGCCTAC-3' |
| L32 | Fw | 5'-GAAAACCAAGCACATGCTGC-3' |
| | Rev | 5'-TTGTTGCACATCAGCAGCAC-5' |
| MafA | Fw | 5'-GAGAAGTGCCAGCTCCAGA-3' |
| | Rev | 5'-TACAGGTCCCGCTCCTTG-3' |
| Nr4a2 | Fw | 5'-CTACCTGTCCAAACTGTTGG-3' |
| | Rev | 5'-GGTAAGGTGTCCAGGAAAAG-3' |
| PC | Fw | 5'-AGTTCCGTGTCCGAGGTGTA-3' |
| | Rev | 5'-TGCTGGTTGTTGAGCACATT-3' |
| Pdx1 | Fw | 5'-AAAACCGTCGCATGAAGTGG-3' |
| | Rev | 5'-CCCGCTACTACGTTTCTTATCT-3' |
| PKIβ | Fw | 5'-GTCCCTCTGGATGTTCAAGC-3' |
| | Rev | 5'-GAAAACCAAGCACATGCTGC-3' |
| RGS2 | Fw | 5'-GCGCTTCCTCAGGAGAAGGCT-3' |
| | Rev | 5'-AACGGCCCCAAGGTCGAGGA-3' |

| Target cDNA (mouse) | | Primer sequence (SEQ ID NOs: 35-52) |
|---|---|---|
| 18S | Fw | 5'-GTTCCGACCATAAACGATGCC-3' |
| | Rev | 5'-TGGTGGTGCCCTTCCGTCAAT-3' |
| GLP1R | Fw | 5'-CTGCCCAGCAACACCAGT-3' |
| | Rev | 5'-CAGTCGGCAGCCTAGAGAGT-3' |
| IRS2 | Fw | 5'-TCCAGGCACTGGAGCTTT-3' |
| | Rev | 5'-GGCTGGTAGCGCTTCACT-3' |
| MafA | Fw | 5'-AGGCCTTCCGGGGTCAGAG-3' |
| | Rev | 5'-TGGAGCTGGCACTTCTCGCT-3' |
| Nr4a2 | Fw | 5'-TCAGAGCCCACGTCGATT-3' |
| | Rev | 5'-TAGTCAGGGTTTGCCTGGAA-3' |
| PC | Fw | 5'-GTTCCGTGTCCGAGGTGTAA-3' |
| | Rev | 5-AACTGGGTGTCCACTGTGC-3' |
| Pdx1 | Fw | 5'-CTTAACCTAGGCGTCGCACAA-3' |
| | Rev | 5'-GAAGCTCAGGGCTGTTTTTCC-3' |
| PKIβ | Fw | 5'-TCTGATCTATGGAAATGAAAATAACAG-3' |
| | Rev | 5'-GGTTTCAGGGGCTTTATGGT-3' |
| RGS2 | Fw | 5'-AGAAAATGAAGCGGACACTCTT-3' |
| | Rev | 5'-TTGCCAGTTTTGGGCTTC-3' |

| Target cDNA (human) | | Primer sequence (SEQ ID NOs: 53-64) |
|---|---|---|
| 18S | Fw | 5'-GTTCCGACCATAAACGATGCC-3' |
| | Rev | 5'-TGGTGGTGCCCTTCCGTCAAT-3' |
| IRS2 | Fw | 5'-TTCTTGTCCCACCACTTGAA-3' |
| | Rev | 5'-CTGACATGTGACATCCTGGTG-3' |
| MafA | Fw | 5'-AGCGAGAAGTGCCAACTCC-3' |
| | Rev | 5'-TTGTACAGGTCCCGCTCTTT-3' |
| Nr4a2 | Fw | 5'-AACTGCACTTCGGCAGAGTT-3' |
| | Rev | 5'-AAAAGCAATGGGGAGTCCA-3' |
| PKIβ | Fw | 5'-GGCTGGAGTCATGCTATACTGAA-3' |
| | Rev | 5'-ATGAATCTGTCCTCATAGCAACAT-3' |
| RGS2 | Fw | 5'-CAAACAGCAAGCTTTCATCAAG-3' |
| | Rev | 5'-AGCCCTGAATGCAGCAAG-3' |

Chromatin Immunoprecipitation

INS-1 cells were plated on 15 cm dishes and exposed to forskolin as specified. Chromatin immunoprecipitation with HIF-1α, CREB, P-CREB and CRTC2 antisera was performed as described (Ravnskjaer et al., 2007). Oligonucleotides used for ChIP analysis are listed in Table 5, below.

TABLE 5

Oligonucleotides used for Q-PCR analysis

| Target enhancer region (rat) | | Sequence (SEQ ID NOs: 65-68) |
|---|---|---|
| MafA | Fw | 5'-CGGTCTGGATCTGGAATTCTGGGA-3' |
| | Rev | 5'-GCCACAAGGAGAACACGGAGGG-3' |
| PKIβ | Fw | 5'-CCCATCTCCACAACGTCACA-3' |
| | Rev | 5'-CGGAAAGGCGAGAAAGAAGC-3' |

Protein Analysis:

Total protein from cultured cells or primary islets was extracted in a Tris-HCl buffer containing 0.5% NP40, protease and phosphatase inhibitors. Proteins were quantified using Bradford reagent and separated using SDS-PAGE. For cellular fractionation, cells were resuspended in hypotonic lysis buffer (40 mM TrisHCl PH 7.4, 10 mM NaCl, 1 mM EDTA with DTT and protease inhibitors). Cells were lysed using a dounce homogenizer and centrifuged. Cytosolic supernatants were collected. Nuclear pellets were washed 3 times and resuspended in nuclear extraction buffer (40 mM TrisHCl PH 7.4, 420 mM NaCl, 10% Glycerol, 1 mM EDTA). Samples were sonicated and centrifuged. Nuclear supernatants were collected.

Histology

After antigen retrieval, 10 μm frozen pancreatic sections were incubated with the indicated antibodies overnight and with fluorophore conjugated secondary antibody and DAPI for 1 h. Sections were mounted with PBS 70% and analysed in a Zeiss VivaTome.

Antisera

Antibodies used for immunoblotting, ChIP and Immunofluorescence are indicated in alphabetical order: glucagon (G2654, Sigma Aldrich), HIF-1α (10006421, Cayman chemical), insulin (180067, ZYMED laboratories), MafA (NB400-137, Novus), PKAa cat (sc-903, Santa Cruz Biotechnology Inc.), PKIB (NBP1-74255, Novus Biologicals), PKIB (IF) (NBP1-55720, Novus Biologicals), pLKB1 (pSer428) (C67A3, Cell Signalling Technology), Phospho PKA substrates (100G7E, Cell Signalling Technology), Tubulin (05-829, Millipore). For CREB, pCREB (pSer133), and CRTC2 detection, rabbit polyclonal antibodies were raised against their respective antigens.

Statistical Analysis

All mice used in experiments were around 10-12 weeks old except mice in HFD or HCD. Whenever possible, littermates of appropriate genotype were used as age-matched controls. The number of mice per experiment was limited by the availability of the required genotype and age. Criteria of exclusion were: 1) gender and age 2) evident signs of disease. 3) spontaneous natural death during the experiment. Sample size (number of mice, islets and cells) is within the range of published literature. All results are presented as means±SEM (standard error of mean). Statistical analysis were performed with unpaired Student's t-test. Differences were considered statistically significant at $p<0.05$ (*$p<0.05$; $p<0.01$ and *$p<0.001$).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publn. 2002/0168707
U.S. Patent Publn. 2003/0051263
U.S. Patent Publn. 2003/0055020
U.S. Patent Publn. 2003/0159161
U.S. Patent Publn. 2004/0064842
U.S. Patent Publn. 2004/0265839
U.S. Patent Publn. 2005/0014166
U.S. Pat. No. 4,797,368
U.S. Pat. No. 4,816,567
U.S. Pat. No. 5,100,883
U.S. Pat. No. 5,118,677
U.S. Pat. No. 5,118,678
U.S. Pat. No. 5,120,842
U.S. Pat. No. 5,139,941
U.S. Pat. No. 5,151,413
U.S. Pat. No. 5,256,790
U.S. Pat. No. 5,258,389
U.S. Pat. No. 6,506,559
U.S. Pat. No. 6,569,620
U.S. Pat. No. 6,573,099
U.S. Pat. No. 6,716,580
U.S. Pat. No. 6,806,084
WO 92/05179
WO 93/11130
WO 94/02136
WO 94/02485
WO 94/09010
WO 95/14023
WO 95/16691
WO 96/41807

Altarejos et al., CREB and the CRTC co-activators: sensors for hormonal and metabolic signals. Nat Rev Mol Cell Biol 12, 141-151, 2011.

Artner et al., MafA is a dedicated activator of the insulin gene in vivo. J Endocrinol 198, 271-279, doi:10.1677/JOE-08-0063, 2008.

Artner et al., MafA and MafB regulate genes critical to beta-cells in a unique temporal manner. Diabetes 59, 2530-2539, doi:10.2337/db10-0190, 2010.

Belyamani et al., Reproductive function in protein kinase inhibitor-deficient mice. Mol Cell Biol 21, 3959-3963, doi:10.1128/MCB.21.12.3959-3963.2001, 2001.

Butler et al., The replication of beta cells in normal physiology, in disease and for therapy. Nature clinical practice. Endocrinology & metabolism 3, 758-768, doi:10.1038/ncpendmet0647, 2007.

Buysschaert et al., Glycemic control and weight changes in patients with type 2 diabetes intensified to three insulin regimens after therapeutic failure to exenatide. Acta clinica Belgica 67, 250-254, 2012.

Cantley et al. Deletion of the von Hippel-Lindau gene in pancreatic beta cells impairs glucose homeostasis in mice. J Clin Invest 119, 125-135, doi:10.1172/JCI26934, 2009.

Drucker, The biology of incretin hormones. Cell Metab 3, 153-165, 2006.

Drucker et al., The incretin system: glucagon-like peptide-1 receptor agonists and dipeptidyl peptidase-4 inhibitors in type 2 diabetes. Lancet 368, 1696-1705, 2006.

Fantozzi et al., Thermostable inhibitor of cAMP-dependent protein kinase enhances the rate of export of the kinase catalytic subunit from the nucleus. J Biol Chem 269, 2676-2686, 1994.

Gunton et al., Loss of ARNT/HIF1beta mediates altered gene expression and pancreatic-islet dysfunction in human type 2 diabetes. Cell 122, 337-349, doi:10.1016/j.cell.2005.05.027, 2005.

Guo et al. Inactivation of specific beta cell transcription factors in type 2 diabetes. J Clin Invest, doi:10.1172/JCI65390, 2013.

Hall et al., Primary-care observational database study of the efficacy of GLP-1 receptor agonists and insulin in the UK. Diabetic medicine: a journal of the British Diabetic Association 30, 681-686, doi:10.1111/dme.12137, 2013.

Hang et al., MafA and MafB activity in pancreatic beta cells. Trends Endocrinol Metab 22, 364-373, doi:10.1016/j.tem.2011.05.003, 2011.

Hoist et al., Loss of incretin effect is a specific, important, and early characteristic of type 2 diabetes. Diabetes Care 34 Suppl 2, S251-257, doi:10.2337/dc11-s227, 2011.

Jhala et al., cAMP promotes pancreatic beta-cell survival via CREB-mediated induction of IRS2. Genes Dev 17, 1575-1580, 2003.

Koo et al., The CREB coactivator TORC2 is a key regulator of fasting glucose metabolism. Nature 437, 1109-1111, 2005.

Matsuoka et al., MafA regulates expression of genes important to islet beta-cell function. Mol Endocrinol 21, 2764-2774, doi:10.1210/me.2007-0028, 2007.

Matthews et al., J. Clin. Endocrinol. Metab. 93 (12): 4810-4817, 2008.

Nauck et al., Diabetes Care. 32(7):1237-43, 2009.

Onnis et al., J. Cell. Mol. Med., 13(9A):2780-2786, 2009.

Park et al., Exendin-4 uses Irs2 signaling to mediate pancreatic beta cell growth and function. J Biol Chem 281, 1159-1168, doi:10.1074/jbc.M508307200, 2006.

Prentki et al., Islet beta cell failure in type 2 diabetes. J Clin Invest 116, 1802-1812, doi:10.1172/JCI29103, 2006.

Preumont et al., Predictive factors associated with primary failure to exenatide and non goal attainment in patients with type 2 diabetes. Acta clinica Belgica 67, 411-415, 2012.

Puri et al., Elimination of von Hippel-Lindau function perturbs pancreas endocrine homeostasis in mice. PLoS ONE 8, e72213, doi:10.1371/journal.pone.0072213, 2013.

Ratner et al., Diabet Med. September; 27(9):1024-32, 2010.

Ravnskjaer et al., Cooperative interactions between CBP and TORC2 confer selectivity to CREB target gene expression. Embo J 26, 2880-2889, 2007.

Scarpetta et al., Evidence for two additional isoforms of the endogenous protein kinase inhibitor of cAMP-dependent protein kinase in mouse. J Biol Chem 268, 10927-10931, 1993.

Screaton et al., The CREB coactivator TORC2 functions as a calcium- and cAMP-sensitive coincidence detector. Cell 119, 61-74, 2004.

Shapiro et al., High yield of rodent islets with intraductal collagenase and stationary digestion—a comparison with standard technique. Cell transplantation 5, 631-638, 1996.

Szabat et al., Maturation of adult beta-cells revealed using a Pdx1/insulin dual-reporter lentivirus. Endocrinology 150, 1627-1635, doi:10.1210/en.2008-1224, 2009.

Talchai et al., Pancreatic beta cell dedifferentiation as a mechanism of diabetic beta cell failure. Cell 150, 1223-1234, doi:10.1016/j.cell.2012.07.029, 2012.

Taylor et al., Dynamics of signaling by PKA. Biochim Biophys Acta 1754, 25-37, doi:10.1016/j.bbapap.2005.08.024, 2005.

Van de Velde et al., mTOR links incretin signaling to HIF induction in pancreatic beta cells. Proc Natl Acad Sci USA 108, 16876-16882, doi:10.1073/pnas.1114228108, 2011.

Wen et al., Heat-stable inhibitors of cAMP-dependent protein kinase carry a nuclear export signal. J Biol Chem 269, 32214-32220, 1994.

Wen et al., Identification of a signal for rapid export of proteins from the nucleus. Cell 82, 463-473, 1995.

Zehetner et al. PVHL is a regulator of glucose metabolism and insulin secretion in pancreatic beta cells. Genes Dev 22, 3135-3146, 2008.

Zhang et al., Genome-wide analysis of cAMP-response element binding protein occupancy, phosphorylation, and target gene activation in human tissues. Proc Natl Acad Sci USA 102, 4459-4464, 2005.

What is claimed is:

1. A method for treating a diabetic subject resistant to a Glucagon-like peptide-1 (GLP1) agonist therapy comprising administering an effective amount of a PKIB pathway inhibitor to the subject, wherein the PKIB pathway inhibitor is selected from the group consisting of an inhibitor of PKIB, a mTOR inhibitor and a HIF inhibitor.

2. The method of claim 1, wherein the subject has been diagnosed with Type II Diabetes.

3. The method of claim 1, wherein the subject is resistant to Exenatide, Liraglutide, Taspoglutide, Albiglutide and/or Lixisenatide.

4. The method of claim 1, wherein the subject is a human subject.

5. The method of claim 1, further comprising administering to the subject a GLP1 agonist.

6. The method of claim 1, wherein the PKIB pathway inhibitor is a mTOR inhibitor.

7. The method of claim 6, wherein the mTOR inhibitor is sirolimus, everolimus, temsirolimus, or rapamycin.

8. The method of claim 1, wherein the PKIB pathway inhibitor is an inhibitor of PKIB.

9. The method of claim 8, wherein the inhibitor of PKIB is an inhibitory nucleic acid.

10. The method of claim 9, wherein the inhibitory nucleic acid is a complementary to all or part of the sequence of SEQ ID NO: 2, SEQ ID NO: 4, SEQ ID NO: 5, SEQ ID NO: 6, SEQ ID NO: 7or SEQ ID NO: 8.

11. The method of claim 9, wherein the inhibitory nucleic acid is a siRNA or dsRNA.

12. The method of claim 1, wherein the PKIB pathway inhibitor is a HIF inhibitor.

13. The method of claim 1, wherein the HIF inhibitor is FG-4592, IOX2, 2-Methoxyestradiol (2-MeOE2), CL67, CAY10585 (CAS 934593-90-5), sc-205346 (CAS 934593-90-5), Chetomin (CAS 1403-36-7) or Chrysin (CAS 480-40-0).

14. The method of claim 1, wherein the subject has been determined to be resistant to the Glucagon-like peptide-1 (GLP1) agonist therapy.

15. The method of claim 5, wherein the GLP1 agonist is Exenatide, Liraglutide, Taspoglutide, Albiglutide or Lixisenatide.

* * * * *

SEQUENCE LISTING

```
<160> NUMBER OF SEQ ID NOS: 79

<210> SEQ ID NO 1
<211> LENGTH: 78
<212> TYPE: PRT
<213> ORGANISM: Homo sapiens

<400> SEQUENCE: 1

Met Arg Thr Asp Ser Ser Lys Met Thr Asp Val Glu Ser Gly Val Ala
1               5                   10                  15

Asn Phe Ala Ser Ser Ala Arg Ala Gly Arg Arg Asn Ala Leu Pro Asp
            20                  25                  30

Ile Gln Ser Ser Ala Ala Thr Asp Gly Thr Ser Asp Leu Pro Leu Lys
        35                  40                  45

Leu Glu Ala Leu Ser Val Lys Glu Asp Ala Lys Glu Lys Asp Glu Lys
    50                  55                  60

Thr Thr Gln Asp Gln Leu Glu Lys Pro Gln Asn Glu Glu Lys
65                  70                  75

<210> SEQ ID NO 2
<211> LENGTH: 2012
<212> TYPE: DNA
```

<213> ORGANISM: Homo sapiens

<400> SEQUENCE: 2

```
gactgcgcat gcgcgtcact agacgacacg gctgtcttct ttcctggaga atttctcaag      60
gactgctggc tggaaactta acggctaatg tggatctgac cgtagtttgc caaattaaga     120
aaacgttttt accctgttga agatttgctt taacttcaaa agtgatgaca agaaagtatg     180
gacaccccct caggaccaac ctgataagtc actgagacgg ggtttcaccg tgttagccag     240
gatggtcttg atctcctgac ctcgtgatcc gcccgcctcg gcctcccaaa gtgctgggat     300
tacaggcgtg agccaccgcg ccccggcagc aaaggttttt ctttcgttta agatgacac      360
actctgaaat taatttgatt ttgagatttg agaacttgga catacatact tcctatggaa     420
ggagtcatgc tatactgaaa agacacttca tcaagataac tctgggagaa gcagaaaacc     480
ctgtgccagg gacaggaaag ataggagaaa gaaagtttat cagaattttt taaacctgtc     540
tcagaaataa caacatattt taatcagaga tttatgttgc tatgaggaca gattcatcaa     600
aaatgactga cgtggagtct ggggtcgcca attttgcatc ttcagcaagg gcaggccgcc     660
ggaatgcctt accagacatc cagagttcag ctgccacaga cggaacctca gatttgcccc     720
tcaaactgga ggctctctcc gtgaaggaag atgcaaaaga gaaagatgaa aaaacaacac     780
aagaccaatt ggaaaagcct caaaatgaag aaaaatgaag gctcataatc tatcaagagt     840
gctgaatttc tgcatgttga aagacttagt ggttctgttt tcttgagaca tttaatctgg     900
tggtaactgt ggtaacattg cagccctaag cagcatgtgt atattagata attgtgttgt     960
gatgctactc actttgattg caatgatgat gtccaaggta agctattaaa aggcaggtta    1020
cttccaaatc gcactgaagg aaaaggttaa gaataataca tgatcacaga aatgcatacc    1080
actgtctgta aacccaacaa aattcactgt tctcttttgg atttatttag cctgatgtat    1140
ttttaattca atttttatgg tgatgggcaa atcattcttg gtaaatgtaa atcaaacatg    1200
attgatttaa aacttcatgg aatttgtaga aaattatgga catttttggt gagaaagaac    1260
aatagtcaaa actcacatgg atagagtgtg tttgtttttt gccaaaaatg ccccagactt    1320
tttcccaaac ctcaaaaacg tcttggaaaa attgtaaaag tttgataaca gaaacatctt    1380
taggatattt ttgtctgaca tattttgctt ctagtatgtg cctactgtga tttttttcat    1440
gtggaaaatg caaaatttgt aacaaaatgg ttatatggaa catgcctatt aaatgaattt    1500
tactatcttc cctaactttg gtctgtgtat gtgtgtgtgt tttactttaa tatgaattat    1560
acaaaatact agttgtttta cactctcttt tcttattctt agggcttttg tgtatgtctg    1620
acttgttttt aaataacttc ctcagcaatg cagaccttaa ttttatatt ttttaaagt      1680
agctaacata gcagtaggca cttaagcatt tagtcaatga tattggtaga aatagtaaaa    1740
tacatccttt aaatatatat ctaagcatat atttaaaag gagcaaaaat aaaaccaaag     1800
tgttagtaaa ttttgattta ttagatattt tagaaaaata atagaattct gaagttttaa    1860
aaatgtcagt aattaattta ttttcatttt cagaaatata tgcatgcagt tatgttttat    1920
ttgattgttg acttaggcta tgtctgtata cagtaaccaa ataaactctt tcactattaa    1980
agagatttct tactgaaaaa aaaaaaaaaa aa                                  2012
```

<210> SEQ ID NO 3
<211> LENGTH: 85
<212> TYPE: PRT
<213> ORGANISM: Homo sapiens

<400> SEQUENCE: 3

```
Met Ser His Gln Asp Val Ala Met Arg Thr Asp Ser Ser Lys Met Thr
1               5                   10                  15

Asp Val Glu Ser Gly Val Ala Asn Phe Ala Ser Ser Ala Arg Ala Gly
            20                  25                  30

Arg Arg Asn Ala Leu Pro Asp Ile Gln Ser Ser Ala Thr Asp Gly
        35                  40                  45

Thr Ser Asp Leu Pro Leu Lys Leu Glu Ala Leu Ser Val Lys Glu Asp
    50                  55                  60

Ala Lys Glu Lys Asp Glu Lys Thr Thr Gln Asp Gln Leu Glu Lys Pro
65                  70                  75                  80

Gln Asn Glu Glu Lys
            85

<210> SEQ ID NO 4
<211> LENGTH: 1953
<212> TYPE: DNA
<213> ORGANISM: Homo sapiens

<400> SEQUENCE: 4
gactgcgcat gcgcgtcact agacgacacg gctgtcttct ttcctggaga atttctcaag      60
gactgctggc tggaaactta acggctaatg tggatctgac cgtagtttgc caaattaaga     120
aaacgttttt accctgttga agatttgctt taacttcaaa agtgatgaca agaaagtatg     180
gacacccctt caggaccaac ctgataagtc actggttttt ctttcgttta agatgacac      240 actctgaaat taatttgatt ttgagatttg agaacttgga catacatact tcctatggaa     300
ggagtcatgc tatactgaaa agacacttca tcaagataac tctgggagaa gcagaaaacc     360
ctgtgccagg gacaggaaag ataggagaaa gaaagtttat cagaattttt taaacctgtc     420
tcagaaataa caacatattt taatcagaga tttgctgaag cttcagagat cacctgccaa     480
acacaggctg aacctgacag catgtcacac caggatgttg ctatgaggac agattcatca     540
aaaatgactg acgtggagtc tggggtcgcc aattttgcat cttcagcaag ggcaggccgc     600
cggaatgcct taccagacat ccagagttca gctgccacag acggaacctc agatttgccc     660
ctcaaactgg aggctctctc cgtgaaggaa gatgcaaaag agaaagatga aaaaacaaca     720
caagaccaat tggaaaagcc tcaaaatgaa gaaaaatgaa ggctcataat ctatcaagag     780
tgctgaattt ctgcatgttg aaagacttag tggttctgtt ttcttgagac atttaatctg     840
gtggtaactg tggtaacatt gcagccctaa gcagcatgtg tatattagat aatttgtgttg    900 tgatgctact cactttgatt gcaatgatga tgtccaaggt aagctattaa aaggcaggtt     960
acttccaaat cgcactgaag gaaaaggtta agaataatac atgatcacag aaatgcatac    1020
cactgtctgt aaaccaaaca aaattcactg ttctcttttg gatttattta gcctgatgta    1080 ttttttaattc aattttatg gtgatgggca atcattcttt ggtaaatgta aatcaaacat    1140
gattgattta aaacttcatg gaatttgtag aaaattatgg acattttgg tgagaaagaa    1200 caatagtcaa aactcacatg gatagagtgt gtttgttttt tgccaaaaat gccccagact    1260
ttttcccaaa cctcaaaaac gtcttggaaa aattgtaaaa gtttgataac agaaacatct    1320
ttaggatatt tttgtctgac atattttgct tctagtatgt gcctactgtg atttttttca    1380
tgtggaaaat gcaaaatttg taacaaaatg gttatatgga acatgcctat taaatgaatt    1440
ttactatctt ccctaacttt ggtctgtgta tgtgtgtgtg ttttacttta atatgaatta    1500
tacaaaatac tagttgtttt acactctctt ttcttattct tagggctttt gtgtatgtct    1560
```

```
gacttgtttt taaataactt cctcagcaat gcagaccttc atttttatat tttttttaaag    1620 tagctaacat agcagtaggc acttaagcat ttagtcaatg atattggtag aaatagtaaa    1680
atacatcctt taaatatata tctaagcata tattttaaaa ggagcaaaaa taaaaccaaa    1740
gtgttagtaa attttgattt attagatatt ttagaaaaat aatagaattc tgaagtttta    1800
aaaatgtcag taattaattt attttcattt tcagaaatat atgcatgcag ttatgtttta    1860
tttgattgtt gacttaggct atgtctgtat acagtaacca aataaactct ttcactatta    1920
aagagatttc ttactgaaaa aaaaaaaaaa aaa                                  1953
```

<210> SEQ ID NO 5
<211> LENGTH: 1614
<212> TYPE: DNA
<213> ORGANISM: Homo sapiens

<400> SEQUENCE: 5

```
aattatccgc acaggctcta gaacttggtt tcttgaagaa gttgtaggaa agaaagttta      60
tcagaatttt ttaaacctgt ctcagaaata acaacatatt ttaatcagag atttgctgaa    120
gcttcagaga tcacctgcca acacaggct gaacctgaca gcatgtcaca ccaggatgtt    180
gctatgagga cagattcatc aaaaatgact gacgtggagt ctggggtcgc caattttgca    240
tcttcagcaa gggcaggccg ccggaatgcc ttaccagaca tccagagttc agctgccaca    300
gacggaacct cagatttgcc cctcaaactg gaggctctct ccgtgaagga agatgcaaaa    360
gagaaagatg aaaaaacaac acaagaccaa ttggaaaagc tcaaaatgaa gaaaaatga    420 aggctcataa tctatcaaga gtgctgaatt tctgcatgtt gaaagactta gtggttctgt    480
tttcttgaga catttaatct ggtggtaact gtggtaacat gcagccctaa gcagcatgt    540 gtatattaga taattgtgtt gtgatgctac tcactttgat tgcaatgatg atgtccaagg    600
taagctatta aaaggcaggt tacttccaaa tcgcactgaa ggaaaaggtt aagaataata    660
catgatcaca gaaatgcata ccactgtctg taaacccaac aaaattcact gttctctttt    720
ggatttattt agcctgatgt atttttaatt caatttttat ggtgatgggc aaatcattct    780
tggtaaatgt aaatcaaaca tgattgattt aaaacttcat ggaatttgta gaaaattatg    840 gacattttg gtgagaaaga acaatagtca aaactcacat ggatagagtg tgtttgtttt    900
ttgccaaaaa tgccccagac ttttctccaa acctcaaaaa cgtcttggaa aaattgtaaa    960
agtttgataa cagaaacatc tttaggatat ttttgtctga catattttgc ttctagtatg    1020
tgcctactgt gatttttttc atgtggaaaa tgcaaaattt gtaacaaaat ggttatatgg    1080
aacatgccta ttaaatgaat tttactatct tccctaactt tggtctgtgt atgtgtgtgt    1140
gttttacttt aatatgaatt atacaaaata ctagttgttt tacactctct tttcttattc    1200
ttagggcttt tgtgtatgtc tgacttgttt taaataact cctcagcaa tgcagacctt    1260 aatttttata tttttttaaa gtagctaaca tagcagtagg cacttaagca tttagtcaat    1320
gatattggta gaaatagtaa aatacatcct taaatatat atctaagcat atattttaaa    1380
aggagcaaaa ataaaaccaa agtgttagta aattttgatt tattagatat tttagaaaaa    1440
taatagaatt ctgaagtttt aaaaatgtca gtaattaatt tattttcatt tcagaaata    1500 tatgcatgca gttatgtttt atttgattgt tgacttaggc tatgtctgta tacagtaacc    1560
aaataaactc tttcactatt aaagagattt cttactgaaa aaaaaaaaaa aaaa           1614
```

<210> SEQ ID NO 6
<211> LENGTH: 1895

```
<212> TYPE: DNA
<213> ORGANISM: Homo sapiens

<400> SEQUENCE: 6
gaaaaaagct accgtggcac gtgccccggg gagtgatgcg gtggcccggt ttgcacggag      60
agcgggacac cgcctgggga gccgcgctcg tagcctgggg gcgggacgcg gcggccgctc     120
cctccgcccc cgagtagctg ccaccgcctg gctgcgcccc agcccagtag ctcagacgcg     180
gccgcatccc ggtggactgt agaggcggca gcgagctaga gcccgagtcg cagctccggg     240
ccgcagagcg ctgggcgagc gcgagcgcca gggcaccggc agggcaggca gctgcgcgcg     300
gctggagtca tgctatactg aaaagacact tcatcaagat aactctggga gaagcagaaa     360
accctgtgcc agggacagga agataggag aaagaaagtt tatcagaatt ttttaaacct      420
gtctcagaaa taacaacata ttttaatcag agatttatgt tgctatgagg acagattcat     480
caaaaatgac tgacgtggag tctggggtcg ccaattttgc atcttcagca agggcaggcc     540
gccggaatgc cttaccagac atccagagtt cagctgccac agacggaacc tcagatttgc     600
ccctcaaact ggaggctctc tccgtgaagg aagatgcaaa agagaaagat gaaaaaacaa     660
cacaagacca attggaaaag cctcaaaatg aagaaaatg aaggctcata atctatcaag      720
agtgctgaat ttctgcatgt tgaaagactt agtggttctg ttttcttgag acatttaatc     780
tggtggtaac tgtggtaaca ttgcagccct aagcagcatg tgtatattag ataattgtgt     840
tgtgatgcta ctcactttga ttgcaatgat gatgtccaag gtaagctatt aaaaggcagg     900
ttacttccaa atcgcactga aggaaaaggt taagaataat acatgatcac agaaatgcat     960
accactgtct gtaaacccaa caaaattcac tgttctcttt tggatttatt tagcctgatg    1020
tatttttaat tcaattttta tggtgatggg caaatcattc ttggtaaatg taaatcaaac    1080
atgattgatt taaaacttca tggaatttgt agaaaattat ggacattttt ggtgagaaag    1140
aacaatagtc aaaactcaca tggatagagt gtgtttgttt tttgccaaaa atgccccaga    1200
cttttttccca aacctcaaaa acgtcttgga aaaattgtaa agtttgata acagaaacat    1260
ctttaggata tttttgtctg acatattttg cttctagtat gtgcctactg tgattttttt    1320
catgtggaaa atgcaaaatt tgtaacaaaa tggttatatg gaacatgcct attaaatgaa    1380
ttttactatc ttccctaact ttggtctgtg tatgtgtgtg tgttttactt taatatgaat    1440
tatacaaaat actagttgtt ttacactctc ttttcttatt cttagggctt ttgtgtatgt    1500
ctgacttgtt tttaaataac ttcctcagca atgcagacct taatttttat attttttaa     1560
agtagctaac atagcagtag gcacttaagc atttagtcaa tgatattggt agaaatagta    1620
aaatacatcc tttaaatata tatctaagca tatatttaa aaggagcaaa ataaaaacca     1680
aagtgttagt aaatttttgat ttattagata ttttagaaaa ataatagaat tctgaagttt   1740
taaaaatgtc agtaattaat ttattttcat tttcagaaat atatgcatgc agttatgttt    1800
tatttgattg ttgacttagg ctatgtctgt atacagtaac caaataaact ctttcactat    1860
taaagagatt tcttactgaa aaaaaaaaaa aaaaa                                1895

<210> SEQ ID NO 7
<211> LENGTH: 1892
<212> TYPE: DNA
<213> ORGANISM: Homo sapiens

<400> SEQUENCE: 7
gactgcgcat gcgcgtcact agacgacacg gctgtcttct ttcctggaga atttctcaag      60
```

-continued

| | |
|---|---|
| gactgctggc tggaaactta acggctaatg tggatctgac cgtagtttgc caaattaaga | 120 |
| aaacgttttt accctgttga agatttgctt taacttcaaa agtgatgaca agaaagtatg | 180 |
| gacacccctt caggaccaac ctgataagtc actggttttt ctttcgttta agatgacac | 240 |
| actctgaaat taatttgatt ttgagatttg agaacttgga catacatact tcctatggaa | 300 |
| ggagtcatgc tatactgaaa agacacttca tcaagataac tctgggagaa gcagaaaacc | 360 |
| ctgtgccagg gacaggaaag ataggagaaa gaaagtttat cagaattttt taaacctgtc | 420 |
| tcagaaataa caacatattt taatcagaga tttatgttgc tatgaggaca gattcatcaa | 480 |
| aaatgactga cgtggagtct ggggtcgcca atttgcatc ttcagcaagg gcaggccgcc | 540 |
| ggaatgcctt accagacatc cagagttcag ctgccacaga cggaacctca gatttgcccc | 600 |
| tcaaactgga ggctctctcc gtgaaggaag atgcaaaaga gaaagatgaa aaaacaacac | 660 |
| aagaccaatt ggaaaagcct caaatgaag aaaaatgaag gctcataatc tatcaagagt | 720 |
| gctgaatttc tgcatgttga agacttagt ggttctgttt tcttgagaca tttaatctgg | 780 |
| tggtaactgt ggtaacattg cagccctaag cagcatgtgt atattagata attgtgttgt | 840 |
| gatgctactc actttgattg caatgatgat gtccaaggta agctattaaa aggcaggtta | 900 |
| cttccaaatc gcactgaagg aaaaggttaa gaataataca tgatcacaga aatgcatacc | 960 |
| actgtctgta aacccaacaa aattcactgt tctcttttgg atttatttag cctgatgtat | 1020 |
| ttttaattca attttatgg tgatgggcaa atcattcttg gtaaatgtaa atcaaacatg | 1080 |
| attgatttaa aacttcatgg aatttgtaga aaattatgga catttttggt gagaaagaac | 1140 |
| aatagtcaaa actcacatgg atagagtgtg tttgtttttt gccaaaaatg ccccagactt | 1200 |
| tttcccaaac ctcaaaaacg tcttggaaaa attgtaaaag tttgataaca gaaacatctt | 1260 |
| taggatattt ttgtctgaca tattttgctt ctagtatgtg cctactgtga ttttttcat | 1320 |
| gtggaaaatg caaaatttgt aacaaaatgg ttatatggaa catgcctatt aaatgaattt | 1380 |
| tactatcttc cctaactttg gtctgtgtat gtgtgtgtgt tttactttaa tatgaattat | 1440 |
| acaaaatact agttgtttta cactctcttt tcttattctt agggcttttg tgtatgtctg | 1500 |
| acttgttttt aaataacttc ctcagcaatg cagaccttaa tttttatatt tttttaaagt | 1560 |
| agctaacata gcagtaggca cttaagcatt tagtcaatga tattggtaga aatagtaaaa | 1620 |
| tacatccttt aaatatatat ctaagcatat attttaaaag gagcaaaaat aaaaccaaag | 1680 |
| tgttagtaaa ttttgattta ttagatattt tagaaaaata atagaattct gaagttttaa | 1740 |
| aaatgtcagt aattaattta ttttcatttt cagaaatata tgcatgcagt tatgtttat | 1800 |
| ttgattgttg acttaggcta tgtctgtata cagtaaccaa ataaactctt tcactattaa | 1860 |
| agagatttct tactgaaaaa aaaaaaaaa aa | 1892 |

<210> SEQ ID NO 8
<211> LENGTH: 1828
<212> TYPE: DNA
<213> ORGANISM: Homo sapiens

<400> SEQUENCE: 8

| | |
|---|---|
| gaaaaaagct accgtggcac gtgccccggg gagtgatgcg gtggcccggt ttgcacggag | 60 |
| agcgggacac cgcctgggga gccgcgctcg tagcctgggg gcgggacgcg gcggccgctc | 120 |
| cctccgcccc cgagtagctg ccaccgcctg gctgcgcccc agcccagtag ctcagacgcg | 180 |
| gccgcatccc ggtggactgt agaggcggca gcgagctaga gcccgagtcg cagctccggg | 240 |
| ccgcagagcg ctgggcgagc gcgagcgcca gggcaccggc agggcaggca gctgcgcgcg | 300 |

```
gctggagtca tgctatactg aaaagacact tcatcaagat aactctggga gaagcagaaa      360
accctgtgcc agggacagga aagataggaa tgttgctatg aggacagatt catcaaaaat      420
gactgacgtg gagtctgggg tcgccaattt tgcatcttca gcaagggcag gccgccggaa      480
tgccttacca gacatccaga gttcagctgc cacagacgga acctcagatt tgcccctcaa      540
actggaggct ctctccgtga aggaagatgc aaaagagaaa gatgaaaaaa caacacaaga      600
ccaattggaa aagcctcaaa atgaagaaaa atgaaggctc ataatctatc aagagtgctg      660
aatttctgca tgttgaaaga cttagtggtt ctgttttctt gagacattta atctggtggt      720
aactgtggta acattgcagc cctaagcagc atgtgtatat tagataattg tgttgtgatg      780
ctactcactt tgattgcaat gatgatgtcc aaggtaagct attaaaaggc aggttacttc      840
caaatcgcac tgaaggaaaa ggttaagaat aatacatgat cacagaaatg cataccactg      900
tctgtaaacc caacaaaatt cactgttctc ttttggattt atttagcctg atgtattttt      960
aattcaattt ttatggtgat gggcaaatca ttccttggta aatgtaaatca aacatgattg     1020
atttaaaact tcatggaatt tgtagaaaat tatggacatt tttggtgaga agaacaata      1080
gtcaaaactc acatggatag agtgtgtttg ttttttgcca aaaatgcccc agacttttttc     1140
ccaaacctca aaacgtctt ggaaaaattg taaaagtttg ataacagaaa catctttagg      1200
atatttttgt ctgacatatt ttgcttctag tatgtgccta ctgtgatttt tttcatgtgg      1260
aaaatgcaaa atttgtaaca aaatggttat atggaacatg cctattaaat gaattttact      1320
atcttcccta actttggtct gtgtatgtgt gtgtgtttta ctttaatatg aattatacaa      1380
aatactagtt gttttacact ctcttttctt attcttaggg cttttgtgta tgtctgactt      1440
gtttttaaat aacttcctca gcaatgcaga ccttaatttt tatattttt taaagtagct      1500
aacatagcag taggcactta agcatttagt caatgatatt ggtagaaata gtaaaataca     1560
tcctttaaat atatatctaa gcatatattt taaaaggagc aaaaataaaa ccaaagtgtt      1620
agtaaattt gatttattag atatttttaga aaaataatag aattctgaag ttttaaaaat     1680
gtcagtaatt aatttatttt cattttcaga aatatatgca tgcagttatg ttttatttga     1740
ttgttgactt aggctatgtc tgtatacagt aaccaaataa actctttcac tattaaagag     1800
atttcttact gaaaaaaaaa aaaaaaaa                                         1828

<210> SEQ ID NO 9
<211> LENGTH: 76
<212> TYPE: PRT
<213> ORGANISM: Homo sapiens

<400> SEQUENCE: 9

Met Thr Asp Val Glu Thr Thr Tyr Ala Asp Phe Ile Ala Ser Gly Arg
1               5                   10                  15

Thr Gly Arg Arg Asn Ala Ile His Asp Ile Leu Val Ser Ser Ala Ser
            20                  25                  30

Gly Asn Ser Asn Glu Leu Ala Leu Lys Leu Ala Gly Leu Asp Ile Asn
        35                  40                  45

Lys Thr Glu Gly Glu Glu Asp Ala Gln Arg Ser Thr Glu Gln Ser
    50                  55                  60

Gly Glu Ala Gln Gly Glu Ala Ala Lys Ser Glu Ser
65                  70                  75

<210> SEQ ID NO 10
<211> LENGTH: 4215
```

<212> TYPE: DNA
<213> ORGANISM: Homo sapiens

<400> SEQUENCE: 10

| | | | | | |
|---|---|---|---|---|---|
| cgctatgcag | agaaagcccc | cctggctctt | ctctctcaat | ccataatcca | gcgatgctgc | 60 |
| agctgtaaaa | gcattaatag | aaaatcaatc | cacaacctcg | cggggcagcg | atcgtcgagc | 120 |
| gccgtttcca | ggctgccttc | cctggggtcg | ggagcggccc | cgctcccccc | gtggctggcg | 180 |
| cggaatgtgg | tgatccgtcc | cggggcgggg | atgacttcat | gcagccggag | ctccgcggcg | 240 |
| ggagcggagg | ctgctgctgg | caggtggggc | gcgggccggc | gcgagctgac | cgagcactcg | 300 |
| gcgggcgcgg | cgggactgcg | gcccgtggcg | gcgtgcgcgg | ggacctgcgc | tgactaggtc | 360 |
| cggggaagtt | tcctgacttt | ctgagaagcc | ctggtttccc | caaagaagtg | atttctgata | 420 |
| gaaatctgaa | ggtcatctcc | aagaaaaaag | agatctagta | tagtcaatga | attaaagaca | 480 |
| agaaggtttc | caatcagtcc | ctgctatgtg | gatatttggt | agcaatgact | gatgtggaaa | 540 |
| ctacatatgc | agatttttatt | gcttcaggaa | gaacaggtag | aagaaatgca | atacatgata | 600 |
| tcctggtttc | ctctgcaagt | ggcaacagca | atgaattagc | cttgaaatta | gcaggtcttg | 660 |
| atatcaacaa | gacagaaggt | gaagaagatg | cacaacgaag | ttctacagaa | caaagtgggg | 720 |
| aagcccaggg | agaagcagca | aaatctgaaa | gctaacaccc | cactttgacc | ctcgaccaca | 780 |
| cctgaaaatg | tctcaaatct | ccaggagtat | ctggaatgca | tttgtttcca | tgagtgaaaa | 840 |
| gaggaaaaag | aaaatggctg | tgctgcattg | caggaacctg | ctcattatca | tgttaaaaat | 900 |
| gagggcagag | gctgtggctg | caggcagact | tttccctacc | tctgtcatta | gcaatggttg | 960 |
| aaatcatgtg | gcttgtgttt | gggcgtcatt | tttgtatgga | tcctttcact | tgatcatatg | 1020 |
| acgaaatgct | tatagagagt | agctccgacc | tagatgatga | ttcttcctgt | agcatctggc | 1080 |
| ccctcacaat | gtcagaggat | ttaattgtgt | ctaattgcga | agggttgatt | gaaccccaga | 1140 |
| gtttaaatat | ctctggctca | agtgttcacc | cagtaaaaga | aagatccaga | aagcactgtt | 1200 |
| tttagcatta | cgtatctgtg | tgttactgct | gtgttatttta | cactgttttg | tattgtacaa | 1260 |
| tatatatgct | cagcactgcc | cccttctctg | attgcttatg | aaaaacaaaa | tgatgtacat | 1320 |
| tactgtgaat | ttttataccca | ctcattttta | aaagggctgt | cttttcattt | tagttttcca | 1380 |
| tactgtggtg | gtgtacacag | gatagaacac | ccttttttaa | aacacagtct | ttccccttgc | 1440 |
| tcattgtatg | ttgatgagtt | gattaagtct | aacagattca | tcaagactcc | attgctttat | 1500 |
| tatagagaca | tttgaaaata | tccattaatg | tgaatatcac | ctgaattcag | tctgtttggt | 1560 |
| gtctgcacag | actggaattc | aatctgtcaa | atttgtttta | ttctcaagtg | gagaacttct | 1620 |
| cccacataat | atatatatat | atatatattt | taatttatga | gaattttgga | caattggaaa | 1680 |
| ggtagaaaag | aaaagccaag | atcatactaa | ggactgaaaa | tattttgttc | tatggaatca | 1740 |
| aatttctcac | aatgctgtat | gatactattt | aaatttggag | gacaacttat | cttcactaag | 1800 |
| ctgaatcagg | tggagaaagt | aatctccttg | caatcatgtg | gacaccaatc | acaaaagtaa | 1860 |
| agccctggtg | ttgtgttttc | atgtcttttt | tcagccctct | cagatccaaa | tgttattatg | 1920 |
| cacttttttaa | tgtttgtaaa | cttttactaa | taattagtgt | gaattgcatt | ctgatacaat | 1980 |
| aatgattatc | attagaagct | aacaaaattc | tcattaatac | tgtgtttgat | ggcctctgct | 2040 |
| gtgttttaac | atcgtgcttc | ttatatggaa | agtttttgtg | agctgtgtaa | tccctctggt | 2100 |
| cagtattatg | aaatcatttg | tcagtggtaa | taaataagga | accagtaata | tgccaatggt | 2160 |
| tcatgaatta | ctggacaaat | agcagacaat | gggagtccct | ttacaataac | gagcccactt | 2220 |

```
agctgtcctt gagggcttag ataccttgcc acgtgaagta ggtagagcag catttcaata     2280
ggtaatttgt gtggttgtgc cagaaactca gcccttctat gtaattacat acaggataaa     2340
aggtaagtct gctcacttct ccttctacag ggcatttcaa ctgactggaa taagggcatg     2400
gttgcattta gtactcaatc agatattact agaaaaaaaa ttaataatgt gagcctttcc     2460
gagagcagaa cgaggaaaga ttaaattta gaatgcttcc ttctgtctaa tccatcaggg      2520
gccaaaatgc ccagtaaaat tcaaacacat cacctattaa tagacttaca agtgagaaaa     2580
gaggttccta gggttatttt aggcaatccc tggtaaactg tttaaaccat caaacccta      2640 cagtcagttt tcagtatcct catttaatat tttaataggt ttcttgtgaa tttaaacttc     2700
tcttctttct taaggttgtg aaattccaaa ctgattttat gtgattttga aaagtttaga    2760
accagtgctg agtctatgtg gagggtttat attcctatgt gatatactgt tattaatgca     2820
tgtggtgcca tgcttgtctt taaatatata aatagtgcta aattgcaaag tcatatggag     2880
ctttggattt agtttgactt cttactactg ctttgtctgc tatattcaaa cccaaaggca     2940
ttcccaagct agggagataa aaattaattt tctaaaatgt ccacatccta tacattttgc     3000
ttattcatgg catcttttcaa atttattttt agtttccttt atttgccaag aatacatatg    3060
gatttgaatt tttaaggaga gaaggaaagg gtaggaaacc agggccttgg gtttagtaac     3120
aggcattgga tgtctattaa ccaactattc ttacgctaat ggctttgcag ctcctattct     3180
cccatttgat cctcaaacaa ttctattaga gtggtatttt tatccaattt cacagattaa     3240
aatataagca ctcaataaaa tataaccttt agaagcttaa aaagctagta agtgatgaac     3300
tgaggatttg aacccatgtt tgtcaccaag gagctttcca gggcacatgt cataaaatta     3360
gagccaactg cagagctgta agggaacttt tagagatgaa cttcttcagc ctccatattt     3420
tacagaagga aactgaatcc cagaaggaga aattgccgtt ctcaaggctc cctggatggg     3480
taataacaca gatatgagta ggtcacataa agtatatctt ttttaaaaaa aagaaattca     3540
attatgtctt atttggggggg tatatttccc agaagatatt tttctggcat gtggtctgta    3600
aacacagcat gattcatatt ttttatgttt catgctactc attttgttta attaccaaca     3660
aacatgggga ctttggcttt ttgacttatt tgcaacaagc atgaaattgt taaatttacc     3720
ttttatcaat tgtaatcatc ctatgccaac atattatcat aaattcatag aaatattttt     3780
aaaaataaat aacagacatt gaaatccaat tcttagataa tactcccaga acagccaatg    3840
gtaaatgccc tatacttgag tcttacttag atgctgtggt aatgcaccat tttagaagat     3900
gaatgatact gctatttctc ttcagggaaa caataatgga taaagaaatg taactgccgg     3960
gcagcaaagc ttctaagtga aacctgtagt agcagtagta gtagggagaa aatgtgtagt     4020
catcaagtga aaataggaaa ggatctatga tttatgatgt cttaatagac cctaaattgt     4080
tctttaatta caagagtggc agtctctgaa gtcatttgtg agcttgtatg acttttgtat    4140
ttagcaatgt tgcatgctca cataattgaa aattaaaagt aacacatttt tctgaaatgt     4200
aaaaaaaaaa aaaaa                                                     4215

<210> SEQ ID NO 11
<211> LENGTH: 4072
<212> TYPE: DNA
<213> ORGANISM: Homo sapiens

<400> SEQUENCE: 11
cgctatgcag agaaagcccc cctggctctt ctctctcaat ccataatcca gcgatgctgc       60
agctgtaaaa gcattaatag aaaatcaatc cacaacctcg cggggcagcg atcgtcgagc      120
```

```
gccgtttcca ggctgccttc cctggggtcg ggagcggccc cgctcccccc gtggctggcg      180
cggaatgtgg tgatccgtcc cggggcgggg atgacttcat gcagccggag ctccgcggcg      240
ggagcggagg ctgctgctgg caggtggggc gcgggccggc gcgagctgac cgagcactcg      300
gcgggcgcgg cgggactgcg gcccgtggcg gcgtgcgcgg ggacctgcgc tgactaggtc      360
cggggaagtc cctgctatgt ggatatttgg tagcaatgac tgatgtggaa actacatatg      420
cagattttat tgcttcagga agaacaggta aagaaaatgc aatacatgat atcctggttt      480
cctctgcaag tggcaacagc aatgaattag ccttgaaatt agcaggtctt gatatcaaca      540
agacagaagg tgaagaagat gcacaacgaa gttctacaga acaaagtggg gaagcccagg      600
gagaagcagc aaaatctgaa agctaacacc ccactttgac cctcgaccac acctgaaaat      660
gtctcaaatc tccaggagta tctggaatgc atttgtttcc atgagtgaaa agaggaaaaa      720
gaaaatggct gtgctgcatt gcaggaacct gctcattatc atgttaaaaa tgagggcaga      780
ggctgtggct gcaggcagac ttttccctac ctctgtcatt agcaatggtt gaaatcatgt      840
ggcttgtgtt tgggcgtcat ttttgtatgg atcctttcac ttgatcatat gacgaaatgc      900
ttatagagag tagctccgac ctagatgatg attcttcctg tagcatctgg cccctcacaa      960
tgtcagagga tttaattgtg tctaattgcg aagggttgat tgaaccccag agtttaaata     1020
tctctggctc aagtgttcac ccagtaaaag aaagatccag aaagcactgt ttttagcatt     1080
acgtatctgt gtgttactgc tgtgttattt acactgtttt gtattgtaca atatatatgc     1140
tcagcactgc cccttctct gattgcttat gaaaaacaaa atgatgtaca ttactgtgaa      1200 ttttatacc actcattttt aaaagggctg tcttttcatt ttagttttcc atactgtggt      1260
ggtgtacaca ggatagaaca ccctttttta aaacacagtc tttccccttg ctcattgtat     1320
gttgatgagt tgattaagtc taacagattc atcaagactc cattgcttta ttatagagac     1380
atttgaaaat atccattaat gtgaatatca cctgaattca gtctgtttgg tgtctgcaca     1440
gactggaatt caatctgtca aatttgtttt attctcaagt ggagaacttc tcccacataa     1500
tatatatata tatatatatt ttaatttatg agaattttgg acaattggaa aggtagaaaa     1560
gaaaagccaa gatcatacta aggactggaa atattttgtt ctatggaatc aaatttctca     1620
caatgctgta tgatactatt taaatttgga ggacaactta tcttcactaa gctgaatcag     1680
gtggagaaag taatctcctt gcaatcatgt ggacaccaat cacaaaagta aagccctggt     1740
gttgtgtttt catgtctttt ttcagccctc tcagatccaa atgttattat gcacttttta     1800
atgtttgtaa acttttacta ataattagtg tgaattgcat tctgatacaa taatgattat     1860
cattagaagc taacaaaatt ctcattaata ctgtgtttga tggcctctgc tgtgttttaa     1920
catcgtgctt cttatatgga aagttttgt gagctgtgta atccctctgg tcagtattat      1980
gaaatcattt gtcagtggta ataaataagg aaccagtaat atgccaatgg ttcatgaatt     2040
actggacaaa tagcagacaa tgggagtccc tttacaataa cgagcccact tagctgtcct     2100
tgagggctta gataccttgc cacgtgaagt aggtagagca gcatttcaat aggtaatttg     2160
tgtggttgtg ccagaaactc agcccttcta tgtaattaca tacaggataa aaggtaagtc     2220
tgctcacttc tccttctaca gggcatttca actgactgga ataagggcat ggttgcattt     2280
agtactcaat cagatattac tagaaaaaaa attaataatg tgagcctttc cgagagcaga     2340
acgaggaaag attaaatttt agaatgcttc cttctgtcta atccatcagg ggccaaaatg     2400
cccagtaaaa ttcaaacaca tcacctatta atagacttac aagtgagaaa agaggttcct     2460
```

-continued

```
agggttattt taggcaatcc ctggtaaact gtttaaacca tcaaacccct acagtcagtt      2520
ttcagtatcc tcatttaata ttttaatagg tttcttgtga atttaaactt ctcttctttc      2580
ttaaggttgt gaaattccaa actgatttta tgtgattttg aaaagtttag aaccagtgct      2640
gagtctatgt ggagggttta tattcctatg tgatatactg ttattaatgc atgtggtgcc      2700
atgcttgtct ttaaatatat aaatagtgct aaattgcaaa gtcatatgga gctttggatt      2760
tagtttgact tcttactact gctttgtctg ctatattcaa acccaaaggc attcccaagc      2820
tagggagata aaaattaatt ttctaaaatg tccacatcct atacattttg cttattcatg      2880
gcatctttca aattttattt tagtttcctt tatttgccaa gaatacatat ggatttgaat      2940
ttttaaggag agaaggaaag ggtaggaaac cagggccttg ggtttagtaa caggcattgg      3000
atgtctatta accaactatt cttacgctaa tggctttgca gctcctattc tcccatttga      3060
tcctcaaaca attctattag agtggtattt ttatccaatt tcacagatta aaatataagc      3120
actcaataaa atataacctt tagaagctta aaaagctagt aagtgatgaa ctgaggattt      3180
gaacccatgt ttgtcaccaa ggagctttcc agggcacatg tcataaaatt agagccaact      3240
gcagagctgt aagggaactt ttagagatga acttcttcag cctccatatt ttacagaagg      3300
aaactgaatc ccagaaggag aaattgccgt tctcaaggct ccctggatgg gtaataacac      3360
agatatgagt aggtcacata agtatatct ttttaaaaa aagaaattc aattatgtct      3420 tatttggggg gtatatttcc cagaagatat ttttctggca tgtggtctgt aaacacagca      3480
tgattcatat ttttatgtt tcatgctact cattttgttt aattaccaac aaacatgggg      3540
actttggctt tttgacttat ttgcaacaag catgaaattg ttaaatttac cttttatcaa      3600
ttgtaatcat cctatgccaa catattatca taaattcata gaaatatttt taaaaataaa      3660
taacagacat tgaaatccaa ttcttagata atactcccag aacagccaat ggtaaatgcc      3720
ctatacttga gtcttactta gatgctgtgg taatgcacca ttttagaaga tgaatgatac      3780
tgctatttct cttcagggaa acaataatgg ataaagaaat gtaactgccg ggcagcaaag      3840
cttctaagtg aaacctgtag tagcagtagt agtagggaga aaatgtgtag tcatcaagtg      3900
aaaataggaa aggatctatg atttatgatg tcttaataga ccctaaattg ttctttaatt      3960
acaagagtgg cagtctctga agtcatttgt gagcttgtat gacttttgta tttagcaatg      4020
ttgcatgctc acataattga aaattaaaag taacacattt ttctgaaatg ta            4072
```

<210> SEQ ID NO 12
<211> LENGTH: 1453
<212> TYPE: DNA
<213> ORGANISM: Homo sapiens

<400> SEQUENCE: 12

```
ccctccgcgg ctgcggaagg ggacgcgaac cgtcctggtc ccatccgagc cgccgtagcg        60
cgagtgccgc gggagttcgg cagcccaggt cgccaaggca acgggctccg ctgcgggttg       120
cgggctgcgg gcgctaggct gccccgggga ggcgctgcgg accggcggcc caggcacgga       180
gaggcggcga ccgcagga gacacgggga agagacagag aggagggtaa agtgagaatc         240
ctgcccgcac cacaggtctg gactgctaac cttgaatcct ggtttcttaa attctgcctc       300
cgcttctgac tgaggaccac tggattttga ggaaactttg gtcttgtggt ggtgaggagg       360
tgatgttctg gaaggaaggt acctagactt tgtggtccct gccaggaagt ggagagtgga       420
aatgtggaat gcctcacact cctcaactag aattcccgta ctgattagtc aacagtggaa       480
aatctgaaga gatgcaagca ggaaaaagaa attaaaccag gcctgaggag cgatgcgaca       540
```

```
ggcatgatgg aggtcgagtc ctcctactcg gacttcatct cctgtgaccg gacaggccgt    600
cggaatgcgg tccctgacat ccagggagac tcagaggctg tgagcgtgag gaagctggct    660
ggagacatgg gcgagctggc actcgagggg gcagaaggac aggtggaggg aagcgcccca    720
gacaaggaag ctggcaacca gccccagagc agcgatggga ccacctcgtc ttgaatctga    780
ccttgtccaa gaaggctgga cgagagacct tctgtcccct cccagagggg aaccctggc     840 actggcccag cagcctcttc tctgagctcc atgtcccaga taaaccaggc cagactgaga    900
aggctcccca gaggcctctg tggcctccac tccgggaaag ccctctgccc acaccacag     960 gcttcacatt cccaccacct tcgcaccgtg cccaggtaca ctttcaagac actgtaacca    1020
caagatgtta tttattgagc tggcgccggg acttgggcgg ggcctgccct acagtgagca    1080
gcccacacag gaacgctcct ctcgcgagcg gcccgggcag ggaccctgtc caacaccaa     1140 cacctcctct ccagcccaat cttctgggtc cagacctgct tgtccctttt ttagaaaaca    1200
cttttaaact ttttaaaaat tttaaacctt ttttcagcag atatggagag agctgacaat    1260
caattcacat tttttaagcc attttagcta aactgtcatt gtgcatctct gaggttccct    1320
catggagctc cacagatcca tttttaggga agggattttg gctcaaaacg atctgaccac    1380
ctctgccctg tccaccagga taagtgacac ctaggaccca ggaaataaat gccgatgatt    1440
tgtgtgaaaa aaa                                                       1453

<210> SEQ ID NO 13
<211> LENGTH: 1201
<212> TYPE: DNA
<213> ORGANISM: Homo sapiens

<400> SEQUENCE: 13
ccctccgcgg ctgcggaagg ggacgcgaac cgtcctggtc ccatccgagc cgccgtagcg     60
cgagtgccgc gggagttcgg cagcccaggt cgccaaggca acgggctccg ctgcgggttg    120
cgggctgcgg gcgctaggct gccccgggga ggcgctgcgg accggcggcc caggcacgga    180
gaggcggcga gaccgcagaa ttcccgtact gattagtcaa cagtggaaaa tctgaagaga    240
tgcaagcagg aaaaagaaat taaaccaggc ctgaggagcg atgcgacagg catgatggag    300
gtcgagtcct cctactcgga cttcatctcc tgtgaccgga caggccgtcg gaatgcggtc    360
cctgacatcc agggagactc agaggctgtg agcgtgagga agctggctgg agacatgggc    420
gagctggcac tcgaggggc agaaggacag gtggagggaa gcgccccaga caaggaagct    480
ggcaaccagc cccagagcag cgatgggacc acctcgtctt gaatctgacc ttgtccaaga    540
aggctggacg agagaccttc tgtcccctcc cagaggggga accctggcac tggcccagca    600
gcctcttctc tgagctccat gtcccagata aaccaggcca gactgagaag gctccccaga    660
ggcctctgtg gcctccactc cgggaaagcc ctctgcccac accacaggc ttcacattcc     720 caccaccttc gcaccgtgcc caggtacact ttcaagacac tgtaaccaca agatgttatt    780
tattgagctg gcgccgggac ttgggcgggg cctgccctac agtgagcagc ccacacagga    840
acgctcctct cgcgagcggc ccgggcaggg accctgtccc aacaccaaca cctcctctcc    900
agcccaatct tctgggtcca gacctgcttg tccctttttt agaaaacact tttaaacttt    960
ttaaaaattt taaaccttt ttcagcagat atggagagag ctgacaatca attcacattt    1020
tttaagccat tttagctaaa ctgtcattgt gcatctctga ggttccctca tggagctcca    1080
cagatccatt tttagggaag ggattttggc tcaaaacgat ctgaccacct ctgccctgtc    1140
```

```
caccaggata agtgacacct aggacccagg aaataaatgc cgatgatttg tgtgaaaaaa    1200
a                                                                   1201

<210> SEQ ID NO 14
<211> LENGTH: 1348
<212> TYPE: DNA
<213> ORGANISM: Homo sapiens

<400> SEQUENCE: 14
ccctccgcgg ctgcggaagg ggacgcgaac cgtcctggtc ccatccgagc cgccgtagcg     60
cgagtgccgc gggagttcgg cagcccaggt cgccaaggca acgggctccg ctgcgggttg    120
cgggctgcgg gcgctaggct gccccgggga ggcgctgcgg accggcggcc caggcacgga    180
gaggcggcga daccgcagga gacacgggga agagacagag aggagggtaa agtgagaatc    240
ctgcccgcac cacaggtctg gactgctaac cttgaatcct ggtttcttaa attctgcctc    300
cgcttctgac tgaggaccac tggattttga ggaaactttg gtcttaattc ccgtactgat    360
tagtcaacag tggaaaatct gaagagatgc aagcaggaaa aagaaattaa accaggcctg    420
aggagcgatg cgacaggcat gatggaggtc gagtcctcct actcggactt catctcctgt    480
gaccggacag gccgtcggaa tgcggtccct gacatccagg gagactcaga ggctgtgagc    540
gtgaggaagc tggctggaga catgggcgag ctggcactcg aggggcaga aggacaggtg    600
gagggaagcg cccagacaa ggaagctggc aaccagcccc agagcagcga tgggaccacc    660
tcgtcttgaa tctgaccttg tccaagaagg ctggacgaga gaccttctgt cccctcccag    720
agggggaacc ctggcactgg cccagcagcc tcttctctga gctccatgtc ccagataaac    780
caggccagac tgagaaggct ccccagaggc ctctgtggcc tccactccgg gaaagccctc    840
tgcccacacc cacaggcttc acattcccac caccttcgca ccgtgcccag gtacactttc    900
aagacactgt aaccacaaga tgttatttat tgagctggcg ccgggacttg ggcggggcct    960
gccctacagt gagcagccca cacaggaacg ctcctctcgc gagcggcccg ggcagggacc   1020
ctgtcccaac accaacacct cctctccagc ccaatcttct gggtccagac ctgcttgtcc   1080
ctttttaga aaacactttt aaactttta aaaattttaa acctttttc agcagatatg    1140
gagagagctg acaatcaatt cacattttt aagccatttt agctaaactg tcattgtgca    1200
tctctgaggt tccctcatgg agctccacag atccatttt agggaaggga ttttggctca    1260
aaacgatctg accacctctg ccctgtccac caggataagt gacacctagg acccaggaaa   1320
taaatgccga tgatttgtgt gaaaaaaa                                      1348

<210> SEQ ID NO 15
<211> LENGTH: 1623
<212> TYPE: DNA
<213> ORGANISM: Homo sapiens

<400> SEQUENCE: 15
ccctccgcgg ctgcggaagg ggacgcgaac cgtcctggtc ccatccgagc cgccgtagcg     60
cgagtgccgc gggagttcgg cagcccaggt cgccaaggca acgggctccg ctgcgggttg    120
cgggctgcgg gcgctaggct gccccgggga ggcgctgcgg accggcggcc caggcacgga    180
gaggcggcga daccgcagga gacacgggga agagacagag aggagggtaa agtgagaatc    240
ctgcccgcac cacaggtctg gactgctaac cttgaatcct ggtttcttaa attctgcctc    300
cgcttctgac tgaggaccac tggattttga ggaaactttg gtcttaattc ccgtactgat    360
tagtcaacag tggaaaatct gaagagatgc aagcaggaaa aagaaattaa accagtaaga    420
```

| | |
|---|---:|
| tagagactgc cactctctgg gaaccttgct gtgtagctga gcctcagcaa gtttgataat | 480 |
| acagacacag caggaggcct ggggaggacc cagcatgccc ggccaccaag cagtgatgca | 540 |
| gctggactgt tccgcagctt tccagagacc tccatggaag cacagacttc catgggttga | 600 |
| agagagtttg tgtcacaatt ccagtcccta gccctggccc tgtgtgaagt agtaacaccg | 660 |
| ccctgccagt aggatatagc tgctgaggag gcctgaggag cgatgcgaca ggcatgatgg | 720 |
| aggtcgagtc ctcctactcg gacttcatct cctgtgaccg gacaggccgt cggaatgcgg | 780 |
| tccctgacat ccagggagac tcagaggctg tgagcgtgag gaagctggct ggagacatgg | 840 |
| gcgagctggc actcgagggg gcagaaggac aggtggaggg aagcgcccca gacaaggaag | 900 |
| ctggcaacca gccccagagc agcgatggga ccacctcgtc ttgaatctga ccttgtccaa | 960 |
| gaaggctgga cgagagacct tctgtcccct cccagagggg gaaccctggc actgcccag | 1020 |
| cagcctcttc tctgagctcc atgtcccaga taaaccaggc cagactgaga aggctcccca | 1080 |
| gaggcctctg tggcctccac tccgggaaag ccctctgccc acaccacag gcttcacatt | 1140 |
| cccaccacct tcgcaccgtg cccaggtaca cttttcaagac actgtaaacca caagatgtta | 1200 |
| tttattgagc tggcgccggg acttgggcgg ggcctgccct acagtgagca gcccacacag | 1260 |
| gaacgctcct ctcgcgagcg gcccgggcag ggaccctgtc ccaacaccaa cacctcctct | 1320 |
| ccagcccaat cttctgggtc cagacctgct tgtcccttt ttagaaaaca ctttaaact | 1380 |
| ttttaaaaat tttaaacctt ttttcagcag atatggagag agctgacaat caattcacat | 1440 |
| tttttaagcc atttagcta aactgtcatt gtgcatctct gaggttccct catggagctc | 1500 |
| cacagatcca tttttaggga agggatttg gctcaaaacg atctgaccac ctctgccctg | 1560 |
| tccaccagga taagtgacac ctaggaccca ggaaataaat gccgatgatt tgtgtgaaaa | 1620 |
| aaa | 1623 |

<210> SEQ ID NO 16
<211> LENGTH: 1186
<212> TYPE: DNA
<213> ORGANISM: Homo sapiens

<400> SEQUENCE: 16

| | |
|---|---:|
| aacacccact aaaacctcaa agtgcttttc atttaggaga cacggggaag agacagagag | 60 |
| gagggtaaag tgagaatcct gcccgcacca caggtctgga ctgctaacct tgaatcctgg | 120 |
| tttcttaaat tctgcctccg cttctgactg aggaccactg gattttgagg aaactttggt | 180 |
| cttaattccc gtactgatta gtcaacagtg gaaaatctga agagatgcaa gcaggaaaaa | 240 |
| gaaattaaac caggcctgag gagcgatgcg acaggcatga tggaggtcga gtcctcctac | 300 |
| tcggacttca tctcctgtga ccggacaggc cgtcggaatg cggtccctga catccaggga | 360 |
| gactcagagg ctgtgagcgt gaggaagctg gctggagaca tgggcgagct ggcactcgag | 420 |
| ggggcagaag gacaggtgga gggaagcgcc ccagacaagg aagctggcaa ccagcccag | 480 |
| agcagcgatg ggaccacctc gtcttgaatc tgaccttgtc caagaaggct ggacgagaga | 540 |
| ccttctgtcc cctcccagag ggggaaccct ggcactggcc cagcagcctc ttctctgagc | 600 |
| tccatgtccc agataaaacca ggccagactg agaaggctcc cagaggcct ctgtggcctc | 660 |
| cactccggga aagccctctg cccacacccca caggcttcac attcccacca ccttcgcacc | 720 |
| gtgcccaggt acactttcaa gacactgtaa ccacaagatg ttatttattg agctggcgcc | 780 |
| gggacttggg cggggcctgc cctacagtga gcagcccaca caggaacgct cctctcgcga | 840 |

-continued

```
gcggcccggg cagggaccct gtcccaacac caacacctcc tctccagccc aatcttctgg    900
gtccagacct gcttgtccct tttttagaaa acacttttaa actttttaaa aattttaaac    960
cttttttcag cagatatgga gagagctgac aatcaattca cattttttaa gccatttttag  1020 ctaaactgtc attgtgcatc tctgaggttc cctcatggag ctccacagat ccattttag   1080 ggaagggatt ttggctcaaa acgatctgac cacctctgcc ctgtccacca ggataagtga  1140
cacctaggac ccaggaaata aatgccgatg atttgtgtga aaaaa              1186
```

<210> SEQ ID NO 17
<211> LENGTH: 22
<212> TYPE: DNA
<213> ORGANISM: Artificial sequence
<220> FEATURE:
<223> OTHER INFORMATION: Synthetic primer

<400> SEQUENCE: 17
ctgctttgtc aacaatgagg tc    22

<210> SEQ ID NO 18
<211> LENGTH: 20
<212> TYPE: DNA
<213> ORGANISM: Artificial sequence
<220> FEATURE:
<223> OTHER INFORMATION: Synthetic primer

<400> SEQUENCE: 18
gtccctctgg atgttcaagc    20

<210> SEQ ID NO 19
<211> LENGTH: 20
<212> TYPE: DNA
<213> ORGANISM: Artificial sequence
<220> FEATURE:
<223> OTHER INFORMATION: Synthetic primer

<400> SEQUENCE: 19
tcatgggcat gtagccatca    20

<210> SEQ ID NO 20
<211> LENGTH: 18
<212> TYPE: DNA
<213> ORGANISM: Artificial sequence
<220> FEATURE:
<223> OTHER INFORMATION: Synthetic primer

<400> SEQUENCE: 20
tctcccaaag tggcctac    18

<210> SEQ ID NO 21
<211> LENGTH: 20
<212> TYPE: DNA
<213> ORGANISM: Artificial sequence
<220> FEATURE:
<223> OTHER INFORMATION: Synthetic primer

<400> SEQUENCE: 21
gaaaaccaag cacatgctgc    20

<210> SEQ ID NO 22
<211> LENGTH: 20
<212> TYPE: DNA
<213> ORGANISM: Artificial sequence
<220> FEATURE:
<223> OTHER INFORMATION: Synthetic primer

```
<400> SEQUENCE: 22
ttgttgcaca tcagcagcac                                              20

<210> SEQ ID NO 23
<211> LENGTH: 19
<212> TYPE: DNA
<213> ORGANISM: Artificial sequence
<220> FEATURE:
<223> OTHER INFORMATION: Synthetic primer

<400> SEQUENCE: 23
gagaagtgcc agctccaga                                               19

<210> SEQ ID NO 24
<211> LENGTH: 18
<212> TYPE: DNA
<213> ORGANISM: Artificial sequence
<220> FEATURE:
<223> OTHER INFORMATION: Synthetic primer

<400> SEQUENCE: 24
tacaggtccc gctccttg                                                18

<210> SEQ ID NO 25
<211> LENGTH: 20
<212> TYPE: DNA
<213> ORGANISM: Artificial sequence
<220> FEATURE:
<223> OTHER INFORMATION: Synthetic primer

<400> SEQUENCE: 25
ctacctgtcc aaactgttgg                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic primer

<400> SEQUENCE: 26
ggtaaggtgt ccaggaaaag                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic primer

<400> SEQUENCE: 27
agttccgtgt ccgaggtgta                                              20

<210> SEQ ID NO 28
<211> LENGTH: 20
<212> TYPE: DNA
<213> ORGANISM: Artificial sequence
<220> FEATURE:
<223> OTHER INFORMATION: Synthetic primer

<400> SEQUENCE: 28
tgctggttgt tgagcacatt                                              20

<210> SEQ ID NO 29
```

```
<211> LENGTH: 20
<212> TYPE: DNA
<213> ORGANISM: Artificial sequence
<220> FEATURE:
<223> OTHER INFORMATION: Synthetic primer

<400> SEQUENCE: 29
aaaaccgtcg catgaagtgg                                          20

<210> SEQ ID NO 30
<211> LENGTH: 22
<212> TYPE: DNA
<213> ORGANISM: Artificial sequence
<220> FEATURE:
<223> OTHER INFORMATION: Synthetic primer

<400> SEQUENCE: 30
cccgctacta cgtttcttat ct                                       22

<210> SEQ ID NO 31
<211> LENGTH: 20
<212> TYPE: DNA
<213> ORGANISM: Artificial sequence
<220> FEATURE:
<223> OTHER INFORMATION: Synthetic primer

<400> SEQUENCE: 31
gtccctctgg atgttcaagc                                          20

<210> SEQ ID NO 32
<211> LENGTH: 20
<212> TYPE: DNA
<213> ORGANISM: Artificial sequence
<220> FEATURE:
<223> OTHER INFORMATION: Synthetic primer

<400> SEQUENCE: 32
gaaaaccaag cacatgctgc                                          20

<210> SEQ ID NO 33
<211> LENGTH: 21
<212> TYPE: DNA
<213> ORGANISM: Artificial sequence
<220> FEATURE:
<223> OTHER INFORMATION: Synthetic primer

<400> SEQUENCE: 33
gcgcttcctc aggagaaggc t                                        21

<210> SEQ ID NO 34
<211> LENGTH: 20
<212> TYPE: DNA
<213> ORGANISM: Artificial sequence
<220> FEATURE:
<223> OTHER INFORMATION: Synthetic primer

<400> SEQUENCE: 34
aacggcccca aggtcgagga                                          20

<210> SEQ ID NO 35
<211> LENGTH: 21
<212> TYPE: DNA
<213> ORGANISM: Artificial sequence
<220> FEATURE:
<223> OTHER INFORMATION: Synthetic primer

<400> SEQUENCE: 35
```
gttccgacca taaacgatgc c                                              21

<210> SEQ ID NO 36
<211> LENGTH: 21
<212> TYPE: DNA
<213> ORGANISM: Artificial sequence
<220> FEATURE:
<223> OTHER INFORMATION: Synthetic primer

<400> SEQUENCE: 36
tggtggtgcc cttccgtcaa t                                              21

<210> SEQ ID NO 37
<211> LENGTH: 18
<212> TYPE: DNA
<213> ORGANISM: Artificial sequence
<220> FEATURE:
<223> OTHER INFORMATION: Synthetic primer

<400> SEQUENCE: 37
ctgcccagca acaccagt                                                  18

<210> SEQ ID NO 38
<211> LENGTH: 20
<212> TYPE: DNA
<213> ORGANISM: Artificial sequence
<220> FEATURE:
<223> OTHER INFORMATION: Synthetic primer

<400> SEQUENCE: 38
cagtcggcag cctagagagt                                                20

<210> SEQ ID NO 39
<211> LENGTH: 18
<212> TYPE: DNA
<213> ORGANISM: Artificial sequence
<220> FEATURE:
<223> OTHER INFORMATION: Synthetic primer

<400> SEQUENCE: 39
tccaggcact ggagcttt                                                  18

<210> SEQ ID NO 40
<211> LENGTH: 18
<212> TYPE: DNA
<213> ORGANISM: Artificial sequence
<220> FEATURE:
<223> OTHER INFORMATION: Synthetic primer

<400> SEQUENCE: 40
ggctggtagc gcttcact                                                  18

<210> SEQ ID NO 41
<211> LENGTH: 19
<212> TYPE: DNA
<213> ORGANISM: Artificial sequence
<220> FEATURE:
<223> OTHER INFORMATION: Synthetic primer

<400> SEQUENCE: 41
aggccttccg gggtcagag                                                 19

<210> SEQ ID NO 42
<211> LENGTH: 20
<212> TYPE: DNA

```
<213> ORGANISM: Artificial sequence
<220> FEATURE:
<223> OTHER INFORMATION: Synthetic primer

<400> SEQUENCE: 42
tggagctggc acttctcgct                                              20

<210> SEQ ID NO 43
<211> LENGTH: 18
<212> TYPE: DNA
<213> ORGANISM: Artificial sequence
<220> FEATURE:
<223> OTHER INFORMATION: Synthetic primer

<400> SEQUENCE: 43
tcagagccca cgtcgatt                                                18

<210> SEQ ID NO 44
<211> LENGTH: 20
<212> TYPE: DNA
<213> ORGANISM: Artificial sequence
<220> FEATURE:
<223> OTHER INFORMATION: Synthetic primer

<400> SEQUENCE: 44
tagtcagggt ttgcctggaa                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic primer

<400> SEQUENCE: 45
gttccgtgtc cgaggtgtaa                                              20

<210> SEQ ID NO 46
<211> LENGTH: 19
<212> TYPE: DNA
<213> ORGANISM: Artificial sequence
<220> FEATURE:
<223> OTHER INFORMATION: Synthetic primer

<400> SEQUENCE: 46
aactgggtgt ccactgtgc                                               19

<210> SEQ ID NO 47
<211> LENGTH: 21
<212> TYPE: DNA
<213> ORGANISM: Artificial sequence
<220> FEATURE:
<223> OTHER INFORMATION: Synthetic primer

<400> SEQUENCE: 47
cttaacctag gcgtcgcaca a                                            21

<210> SEQ ID NO 48
<211> LENGTH: 21
<212> TYPE: DNA
<213> ORGANISM: Artificial sequence
<220> FEATURE:
<223> OTHER INFORMATION: Synthetic primer

<400> SEQUENCE: 48
gaagctcagg gctgtttttc c                                            21
```

<210> SEQ ID NO 49
<211> LENGTH: 27
<212> TYPE: DNA
<213> ORGANISM: Artificial sequence
<220> FEATURE:
<223> OTHER INFORMATION: Synthetic primer

<400> SEQUENCE: 49
tctgatctat ggaaatgaaa ataacag                               27

<210> SEQ ID NO 50
<211> LENGTH: 20
<212> TYPE: DNA
<213> ORGANISM: Artificial sequence
<220> FEATURE:
<223> OTHER INFORMATION: Synthetic primer

<400> SEQUENCE: 50
ggtttcaggg gctttatggt                                       20

<210> SEQ ID NO 51
<211> LENGTH: 22
<212> TYPE: DNA
<213> ORGANISM: Artificial sequence
<220> FEATURE:
<223> OTHER INFORMATION: Synthetic primer

<400> SEQUENCE: 51
agaaaatgaa gcggacactc tt                                    22

<210> SEQ ID NO 52
<211> LENGTH: 18
<212> TYPE: DNA
<213> ORGANISM: Artificial sequence
<220> FEATURE:
<223> OTHER INFORMATION: Synthetic primer

<400> SEQUENCE: 52
ttgccagttt tgggcttc                                         18

<210> SEQ ID NO 53
<211> LENGTH: 21
<212> TYPE: DNA
<213> ORGANISM: Artificial sequence
<220> FEATURE:
<223> OTHER INFORMATION: Synthetic primer

<400> SEQUENCE: 53
gttccgacca taaacgatgc c                                     21

<210> SEQ ID NO 54
<211> LENGTH: 21
<212> TYPE: DNA
<213> ORGANISM: Artificial sequence
<220> FEATURE:
<223> OTHER INFORMATION: Synthetic primer

<400> SEQUENCE: 54
tggtggtgcc cttccgtcaa t                                     21

<210> SEQ ID NO 55
<211> LENGTH: 20
<212> TYPE: DNA
<213> ORGANISM: Artificial sequence
<220> FEATURE:

<223> OTHER INFORMATION: Synthetic primer

<400> SEQUENCE: 55
ttcttgtccc accacttgaa                                               20

<210> SEQ ID NO 56
<211> LENGTH: 21
<212> TYPE: DNA
<213> ORGANISM: Artificial sequence
<220> FEATURE:
<223> OTHER INFORMATION: Synthetic primer

<400> SEQUENCE: 56
ctgacatgtg acatcctggt g                                             21

<210> SEQ ID NO 57
<211> LENGTH: 19
<212> TYPE: DNA
<213> ORGANISM: Artificial sequence
<220> FEATURE:
<223> OTHER INFORMATION: Synthetic primer

<400> SEQUENCE: 57
agcgagaagt gccaactcc                                                19

<210> SEQ ID NO 58
<211> LENGTH: 20
<212> TYPE: DNA
<213> ORGANISM: Artificial sequence
<220> FEATURE:
<223> OTHER INFORMATION: Synthetic primer

<400> SEQUENCE: 58
ttgtacaggt cccgctcttt                                               20

<210> SEQ ID NO 59
<211> LENGTH: 20
<212> TYPE: DNA
<213> ORGANISM: Artificial sequence
<220> FEATURE:
<223> OTHER INFORMATION: Artificial sequence

<400> SEQUENCE: 59
aactgcactt cggcagagtt                                               20

<210> SEQ ID NO 60
<211> LENGTH: 19
<212> TYPE: DNA
<213> ORGANISM: Artificial sequence
<220> FEATURE:
<223> OTHER INFORMATION: Synthetic primer

<400> SEQUENCE: 60
aaaagcaatg gggagtcca                                                19

<210> SEQ ID NO 61
<211> LENGTH: 23
<212> TYPE: DNA
<213> ORGANISM: Artificial sequence
<220> FEATURE:
<223> OTHER INFORMATION: Synthetic primer

<400> SEQUENCE: 61
ggctggagtc atgctatact gaa                                           23

<210> SEQ ID NO 62
<211> LENGTH: 24
<212> TYPE: DNA
<213> ORGANISM: Artificial sequence
<220> FEATURE:
<223> OTHER INFORMATION: Synthetic primer

<400> SEQUENCE: 62
atgaatctgt cctcatagca acat                                              24

<210> SEQ ID NO 63
<211> LENGTH: 22
<212> TYPE: DNA
<213> ORGANISM: Artificial sequence
<220> FEATURE:
<223> OTHER INFORMATION: Synthetic primer

<400> SEQUENCE: 63
caaacagcaa gctttcatca ag                                                22

<210> SEQ ID NO 64
<211> LENGTH: 18
<212> TYPE: DNA
<213> ORGANISM: Artificial sequence
<220> FEATURE:
<223> OTHER INFORMATION: Synthetic primer

<400> SEQUENCE: 64
agccctgaat gcagcaag                                                     18

<210> SEQ ID NO 65
<211> LENGTH: 24
<212> TYPE: DNA
<213> ORGANISM: Artificial sequence
<220> FEATURE:
<223> OTHER INFORMATION: Synthetic primer

<400> SEQUENCE: 65
cggtctggat ctggaattct ggga                                              24

<210> SEQ ID NO 66
<211> LENGTH: 22
<212> TYPE: DNA
<213> ORGANISM: Artificial sequence
<220> FEATURE:
<223> OTHER INFORMATION: Synthetic primer

<400> SEQUENCE: 66
gccacaagga gaacacggag gg                                                22

<210> SEQ ID NO 67
<211> LENGTH: 20
<212> TYPE: DNA
<213> ORGANISM: Artificial sequence
<220> FEATURE:
<223> OTHER INFORMATION: Synthetic primer

<400> SEQUENCE: 67
cccatctcca caacgtcaca                                                   20

<210> SEQ ID NO 68
<211> LENGTH: 20
<212> TYPE: DNA
<213> ORGANISM: Artificial sequence
<220> FEATURE:
<223> OTHER INFORMATION: Synthetic primer

<400> SEQUENCE: 68
cggaaaggcg agaaagaagc                                               20

<210> SEQ ID NO 69
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 69
gaggaucugu avuggauga                                                19

<210> SEQ ID NO 70
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 70
ucauccagua cagauccuc                                                19

<210> SEQ ID NO 71
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 71
gcaagcugac ccugaaguuc                                               20

<210> SEQ ID NO 72
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 72
gaacuucagg gucagcuugc                                               20

<210> SEQ ID NO 73
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 73
catctcgaga tgaggacaga ttc                                           23

<210> SEQ ID NO 74
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 74
catggtacct tatttgtctt cgtctag                                       27

<210> SEQ ID NO 75
<211> LENGTH: 29

```
<212> TYPE: DNA
<213> ORGANISM: Artificial sequence
<220> FEATURE:
<223> OTHER INFORMATION: Synthetic oligonucleotide

<400> SEQUENCE: 75
cataccggta tgaggacaga ttcatcaga                                    29

<210> SEQ ID NO 76
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 76
catgcggccg ctcattttcc ttcatttag                                    29

<210> SEQ ID NO 77
<211> LENGTH: 27
<212> TYPE: DNA
<213> ORGANISM: Mus musculus

<400> SEQUENCE: 77
caagtgtgac ggtggcaatc tgcttgc                                      27

<210> SEQ ID NO 78
<211> LENGTH: 27
<212> TYPE: DNA
<213> ORGANISM: Rattus norvegicus

<400> SEQUENCE: 78
acatctcgtc acccaccctc cgtgttc                                      27

<210> SEQ ID NO 79
<211> LENGTH: 27
<212> TYPE: DNA
<213> ORGANISM: Homo sapiens

<400> SEQUENCE: 79
gcccatcgtc acctcctttg ccccgtg                                      27
```